United States Patent
Lee et al.

(10) Patent No.: US 11,597,700 B1
(45) Date of Patent: Mar. 7, 2023

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Bum Sung Lee, Cheonan-si (KR); Jong Gwang Park, Cheonan-si (KR); Jae Duk Yoo, Cheonan-si (KR); Jae Wan Jang, Cheonan-si (KR); Yun Suk Lee, Cheonan-si (KR); Soung Yun Mun, Cheonan-si (KR); In Goo Lee, Cheonan-si (KR); Hyun Jung Baek, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 17/652,566

(22) Filed: Feb. 25, 2022

(30) Foreign Application Priority Data

Aug. 20, 2021 (KR) .................. 10-2021-0110230

(51) Int. Cl.
| | |
|---|---|
| *C07D 209/86* | (2006.01) |
| *C07D 487/04* | (2006.01) |
| *C07D 519/00* | (2006.01) |
| *C09K 11/06* | (2006.01) |
| *H01L 51/00* | (2006.01) |
| *H01L 51/50* | (2006.01) |

(52) U.S. Cl.
CPC ......... *C07D 209/86* (2013.01); *C07D 487/04* (2013.01); *C07D 519/00* (2013.01); *C09K 11/06* (2013.01); *H01L 51/0058* (2013.01); *H01L 51/0072* (2013.01); *H01L 51/0073* (2013.01); *H01L 51/0074* (2013.01); *H01L 51/5044* (2013.01); *H01L 51/5056* (2013.01); *H01L 51/5072* (2013.01); *C07B 2200/05* (2013.01); *H01L 51/5016* (2013.01)

(58) Field of Classification Search
CPC ........................... C07D 209/86; C07D 487/04
See application file for complete search history.

(56) References Cited

U.S. PATENT DOCUMENTS

2020/0212310 A1* 7/2020 Kim .................... H01L 51/0073

FOREIGN PATENT DOCUMENTS

| KR | 10-2015-0059202 A | 11/2015 | |
|---|---|---|---|
| KR | 10-2019-0034074 A | 4/2019 | |
| KR | 10-20190028057 A | 9/2019 | |
| KR | 10-2020-0026083 A | 3/2020 | |
| KR | 10-2021-0048735 A | 5/2021 | |
| WO | 2010/126234 A1 | 11/2010 | |
| WO | WO-2010126234 A1 * | 11/2010 | ............ C07F 7/0812 |

OTHER PUBLICATIONS https://spie.org/news/5197-transparent-organic-leds-for-new-lighting-applications?SSO=1 (Year: 2013).*
Notice of Allowance issued in corresponding Korean Patent Application, dated Dec. 22, 2021.

* cited by examiner

*Primary Examiner* — Vu A Nguyen
(74) *Attorney, Agent, or Firm* — Vorys, Sater, Seymour and Pease LLP; Mih Suhn Koh

(57) ABSTRACT

Provided are a novel compound capable of improving the luminous efficiency, stability and lifespan of a device, an organic electronic element using the same, and an electronic device thereof.

20 Claims, 3 Drawing Sheets

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like. A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and can be classified into a fluorescent material derived from a singlet excited state of an electron and a phosphorescent material derived from a triplet excited state of an electron according to the light emission mechanism. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, for this reason, power consumption greater than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

In other words, in order to fully exhibit the excellent characteristics of an organic electronic element, materials constituting the organic layer in the device, such as hole injection material, hole transport material, light emitting material, electron transport material, electron injection material, etc., should be supported by a stable and efficient material in advance, but the development of a stable and efficient organic material layer material for an organic electronic device has not yet been sufficiently made. Therefore, the development of new materials is continuously required, and in particular, the development of a host material for the emitting layer is urgently required.

Figure 1:
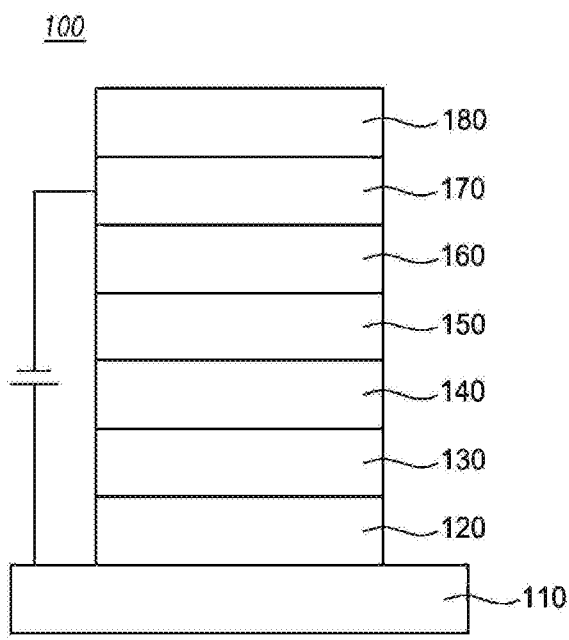
FIG. 1 to FIG. 3 are exemplary views of an organic electroluminescent device according to the present invention.

The numbers in the drawings indicate:
100, 200, 300: organic electronic element
110: the first electrode
120: hole injection layer
130: hole transport layer
140: emitting layer
150: electron transport layer
160: electron injection layer
170: second electrode
180: light efficiency enhancing Layer
210: buffer layer
220: emitting-auxiliary layer
320: first hole injection layer
330: first hole transport layer
340: first emitting layer
350: first electron transport layer
360: first charge generation layer
361: second charge generation layer
420: second hole injection layer
430: second hole transport layer
440: second emitting layer
450: second electron transport layer
CGL: charge generation layer
ST1: first stack
ST2: second stack

DETAILED DESCRIPTION OF THE INVENTION

Summary

In order to solve the problems of the above-mentioned background art, the present invention has revealed a compound having a novel structure, and when the compound is applied to an organic electronic element, it has been found that the driving voltage, efficiency, and lifespan of the device can be significantly improved.

Accordingly, an object of the present invention is to provide a novel compound, an organic electronic element using the same, and an electronic device thereof.

Technical Solution

The present invention provides a compound represented by Formula (1).

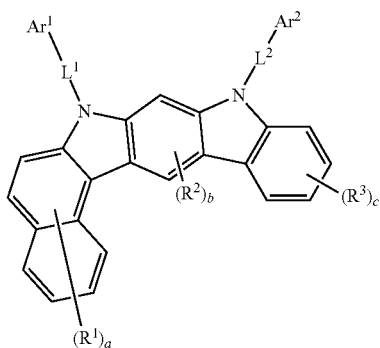

Formula (1)

In another aspect, the present invention provides an organic electronic element comprising the compound represented by Formula (1) and an electronic device thereof.

Effects of the Invention

By using the compound according to the present invention, high luminous efficiency, low driving voltage and high heat resistance of the device can be achieved, and color purity and lifespan of the device can be greatly improved.

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl. Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

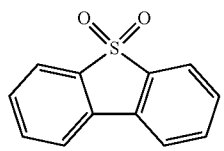 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

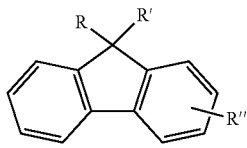

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

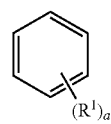

Here, when a is an integer of zero, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

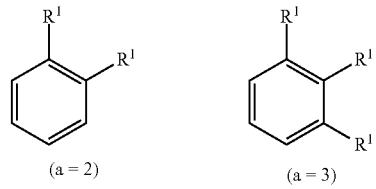

Hereinafter, a compound according to an aspect of the present invention and an organic electronic element including the same will be described.

The present invention provides a compound represented by Formula (1).

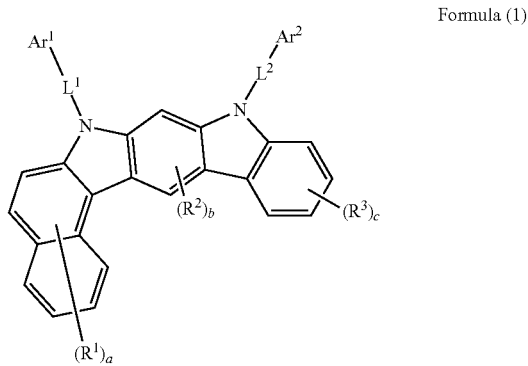

Formula (1)

Wherein, each symbol may be defined as follows.

1) $Ar^1$ and $Ar^2$ are each independently of a $C_6$-$C_{60}$ aryl group; or $C_2$-$C_{60}$ heteroaryl group;

When $Ar^1$ and $Ar^2$ are aryl groups, they may be preferably $C_6$-$C_{30}$ aryl groups, more preferably $C_6$-$C_{25}$ aryl groups, such as phenylene, biphenyl, naphthalene, terphenyl, and the like;

When $Ar^1$ and $Ar^2$ are heteroaryl group, they may be preferably $C_2$-$C_{30}$ heteroaryl groups, more preferably $C_2$-$C_{24}$ heteroaryl groups, exemplarily, it may be carbazole, dibenzofuran, dibenzothiophene, benzonaphthofuran, benzonaphthothiophene, benzoxazole, benzothiazole, benzothiophene, or the like.

2) $L^1$ and $L^2$ are each independently selected from the group consisting of a single bond; $C_6$-$C_{60}$ arylene group; and $C_2$-$C_{60}$ heteroarylene group;

When $L^1$ and $L^2$ are arylene groups, they may be preferably $C_6$-$C_{30}$ arylene groups, more preferably $C_6$-$C_{25}$ arylene groups, such as phenylene, biphenyl, naphthalene, terphenyl, and the like;

When $L^1$ and $L^2$ are heteroarylene group, they may be preferably $C_2$~$C_{30}$ heteroarylene groups, more preferably $C_2$~$C_{24}$ heteroarylene groups.

3) $R^1$, $R^2$ and $R^3$ are the same or different from each other, and independently of each other are hydrogen or deuterium;

4) a is an integer of 0 to 6, b is an integer of 0 to 2, c is an integer of 0 to 4.}
provided that at least one of $Ar^1$, $Ar^2$, $L^1$, $L^2$, $R^1$, $R^2$ and $R^3$ is necessarily substituted with deuterium;
wherein the aryl group, arylene group, heteroaryl group, heteroarylene group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

However, compounds represented by the following Formula (2) in Formula (1) are excluded:

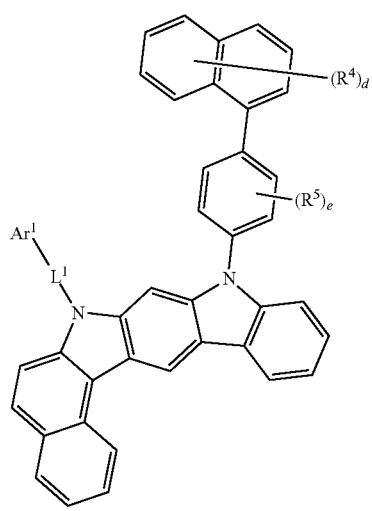

Formula (2)

Wherein,
1) $Ar^1$ and $L^1$ are the same as defined in Formula (1),
2) $R^4$ and $R^5$ are deuterium,
3) d is an integer from 0 to 7, and e is an integer from 0 to 4.

Also, the present invention provides a compound in which one of $L^1$ and $L^2$ is necessarily substituted with deuterium.

Also, the present invention provides a compound in which one of $L^1$ and $L^2$ is a $C_6$-$C_{60}$ arylene group substituted with deuterium.

Also, the present invention provides a compound in which one of $Ar^1$ and $Ar^2$ is necessarily substituted with deuterium.

Also, the present invention provides a compound in which one of $Ar^1$ and $Ar^2$ is a $C_6$-$C_{60}$ aryl group substituted with deuterium.

Also, the present invention provides a compound in which one of $R^1$ to $R^3$ is deuterium.

Also, the present invention provides a compound in which at least one of $Ar^1$ and $Ar^2$ is represented by the following Formula (3).

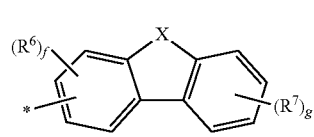

Formula (3)

Wherein, each symbol may be defined as follows.
1) $R^6$ and $R^7$ are the same or different from each other, and are each independently selected from the group consisting of a hydrogen; deuterium; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-$NR^aR^b$; or an adjacent plurality of $R^6$s, or a plurality of $R^7$s may be bonded to each other to form a ring.

When $R^6$ and $R^7$ are an aryl group, it may be preferably a $C_6$-$C_{30}$ aryl group, and more preferably a $C_6$-$C_{25}$ aryl group, for example, it may be phenylene, biphenyl, naphthalene, terphenyl, etc.

When $R^6$ and $R^7$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R^6$ and $R^7$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^6$ and $R^7$ are an alkyl group, it may be preferably a $C_1$-$C_{30}$ alkyl group, and more preferably a $C_1$-$C_{24}$ alkyl group.

When $R^6$ and $R^7$ are an alkoxy group, it may be preferably a $C_1$-$C_{24}$ alkoxy group.

When $R^6$ and $R^7$ are an aryloxy group, it may be preferably a $C_6$-$C_{24}$ aryloxy group.

(2) L' is selected from the group consisting of single bond; a $C_6$-$C_{60}$ arylene group; a $C_2$-$C_{60}$ heterocyclic group including at least one heteroatom of O, N, S, Si or P;

Wherein L' is an arylene group, it may be preferably a $C_6$-$C_{30}$ arylene group, more preferably a $C_6$-$C_{25}$ arylene group, for example, phenylene, biphenyl, naphthalene, terphenyl, etc.

Wherein L' is a heterocyclic group, it may be preferably a $C_2$~$C_{30}$ heterocyclic group, and more preferably a $C_2$~$C_{24}$ heterocyclic group.

(3) When $R^a$ and $R^b$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; an $C_2$~$C_{20}$ alkenyl group; a $C_2$-$C_{20}$ alkynyl group; a $C_1$-$C_{30}$ alkoxy group; and a $C_6$-$C_{30}$ aryloxy group;

When $R^a$ and $R^b$ are an aryl group, they may be preferably a $C_6$-$C_{30}$ aryl group, most preferably a $C_6$-$C_{25}$ aryl group, exemplarily, they may be phenylene, biphenyl, naphthalene, terphenyl, and the like.

When $R^a$ and $R^b$ are a heterocyclic group, they may be preferably a $C_2$-$C_{30}$ heterocyclic group, and more preferably a $C_2$-$C_{24}$ heterocyclic group, When $R^a$ and $R^b$ are a fused ring group, they may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, When $R^a$ and $R^b$ are an alkyl group, they may be preferably an $C_1$~$C_{30}$ alkyl group, more preferably an $C_1$~$C_{24}$ alkyl group.

When $R^a$ and $R^b$ are an alkoxy group, they may be preferably a $C_1$-$C_{24}$ alkoxy group.

When $R^a$ and $R^b$ are an aryloxy group, they may be preferably a $C_6$-$C_{24}$ aryloxy group.

(4) f is an integer from 0 to 3, g is an integer from 0 to 4, (5) * means the combined position, (6) X is NR', O or S, (7) Wherein R' is a $C_6$-$C_{60}$ aryl group; or $C_2$-$C_{60}$ heteroaryl group;

When R' is an aryl group, it may be preferably a $C_6$-$C_{30}$ aryl group, most preferably a $C_6$-$C_{25}$ aryl group, exemplarily, they may be phenylene, biphenyl, naphthalene, terphenyl, and the like.

When R' is a heteroaryl group, it may be preferably a $C_2$-$C_{30}$ heteroaryl group, and more preferably a $C_2$-$C_{24}$ heteroaryl group, exemplarily, it may be carbazole, dibenzofuran, dibenzothiophene, benzonaphthofuran, benzonaphthothiophene, benzoxazole, benzothiazole, benzothiophene, or the like.

However, one of $Ar^1$, $Ar^2$, $L^1$, $L^2$, $R^1$, $R^2$, $R^3$, $R^6$ and $R^7$ is always substituted with deuterium.

Also, in the present invention, $L^1$ and $L^2$ are each independently a $C_6$-$C_{30}$ arylene group, $Ar^1$ and $Ar^2$ are each independently a $C_6$-$C_{30}$ aryl group; and at least one of $L^1$, $L^2$, $Ar^1$ and $Ar^2$ is substituted with deuterium.

Also, in the present invention, $L^2$ is a $C_6$-$C_{30}$ arylene group necessarily containing deuterium, and $L^1$, $Ar^1$, $Ar^2$, $R^1$, $R^2$ and $R^3$ are not substituted with deuterium Also, the present invention, $Ar^2$ is a $C_6$-$C_{30}$ aryl group necessarily containing deuterium, and $L^1$, $L^2$, $Ar^1$, $R^1$, $R^2$ and $R^3$ are not substituted with deuterium Also, the present invention provides a compound wherein Formula (1) is represented by the following Formulas (1-a) to (1-q).

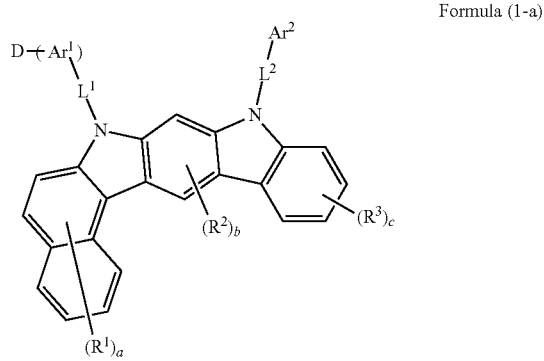

Formula (1-a)

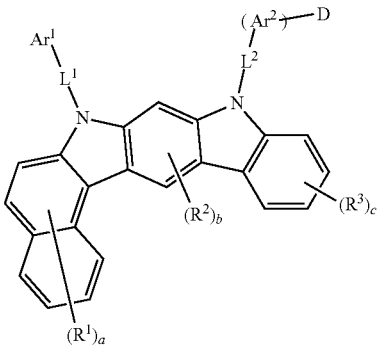

Formula (1-b)

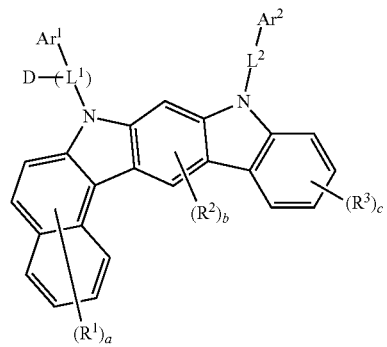

Formula (1-c)

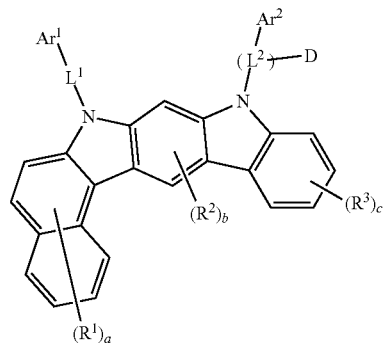

Formula (1-d)

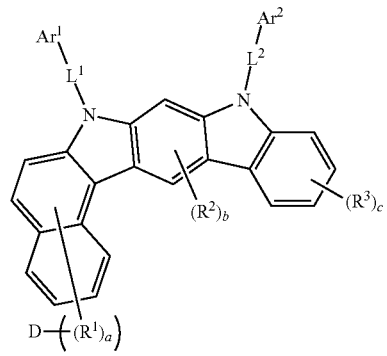

Formula (1-e)

Formula (1-f)
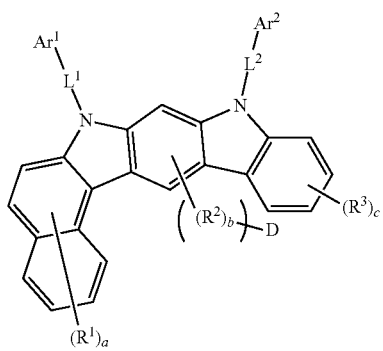
Formula (1-g)
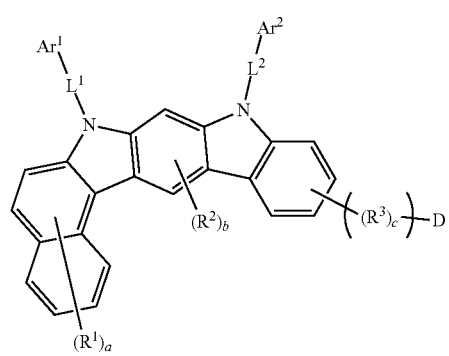
Formula (1-h)
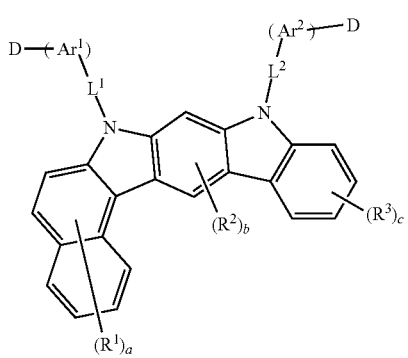
Formula (1-i)
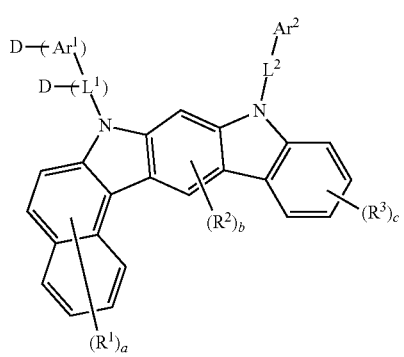
Formula (1-j)
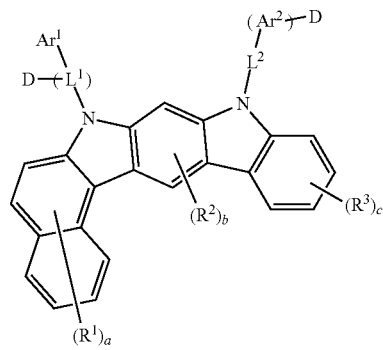
Formula (1-k)
Formula (1-l)
Formula (1-m)
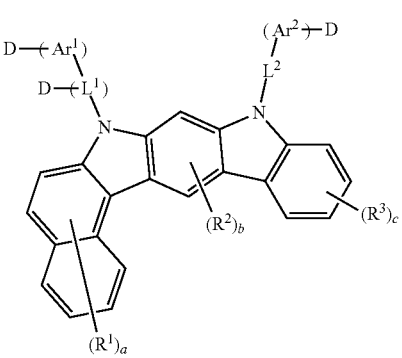

Formula (1-n)
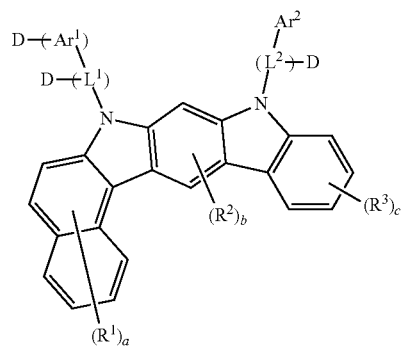
Formula (1-o)
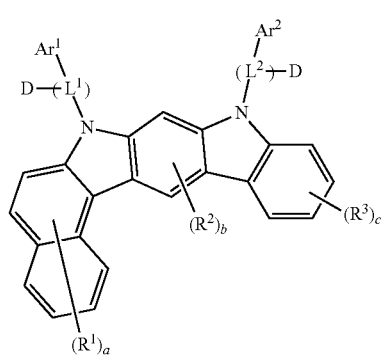
Formula (1-p)
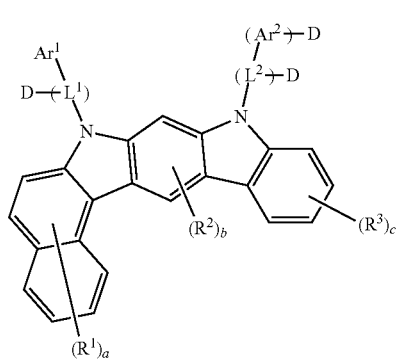
Formula (1-q)
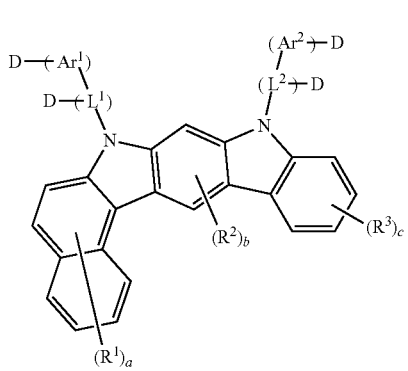
{Wherein, $Ar^1$, $Ar^2$, $L^1$, $L^2$, $R^1$, $R^2$, $R^3$, a, b and c are the same as defined above.}
Also, the compound represented by Formula (1) is represented by any of the following compounds P-1 to P-90
P-1
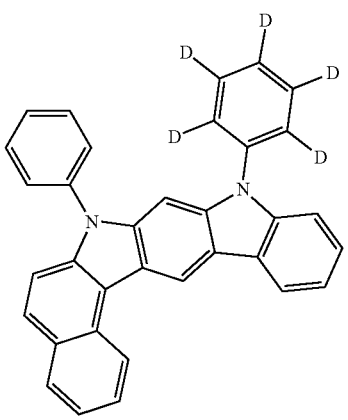
P-2
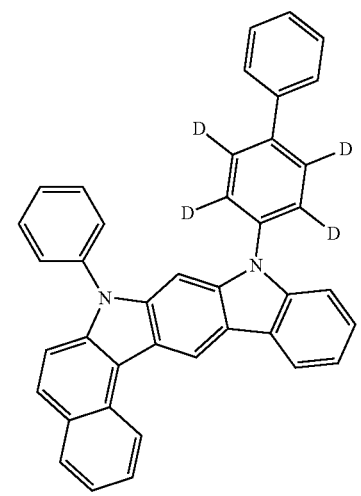
P-3
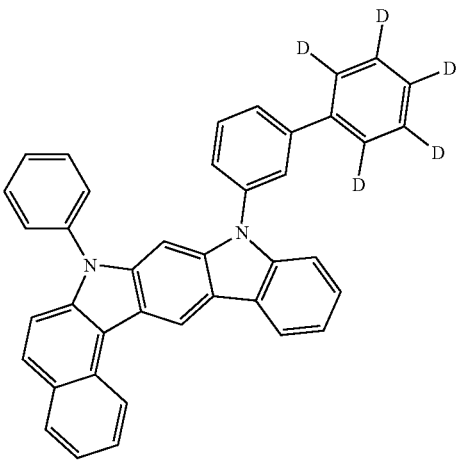

P-4
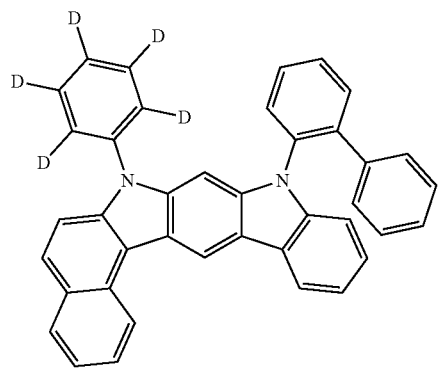
P-5
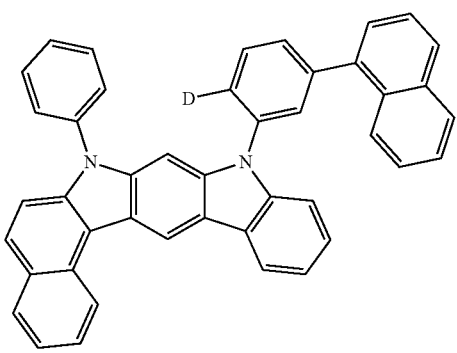
P-6
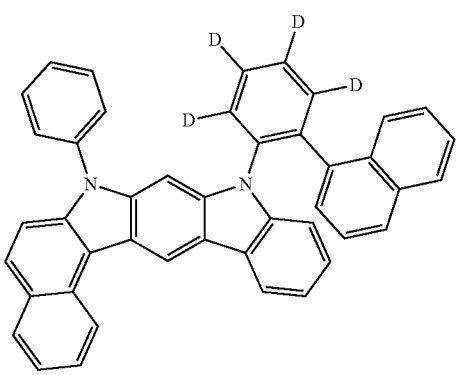
P-7
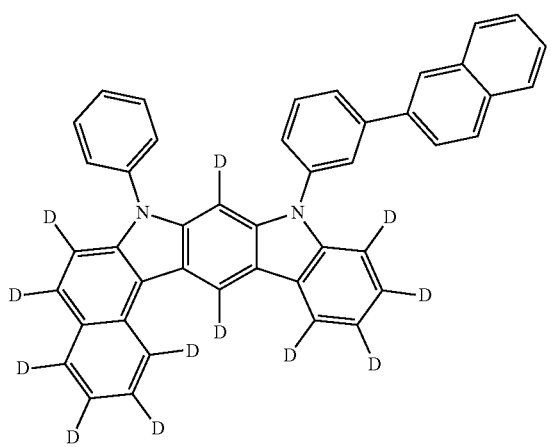
P-8
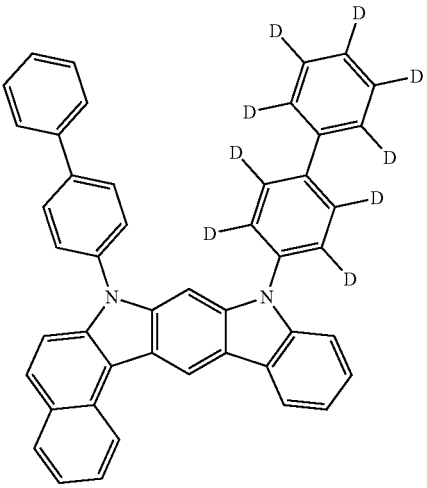
P-9
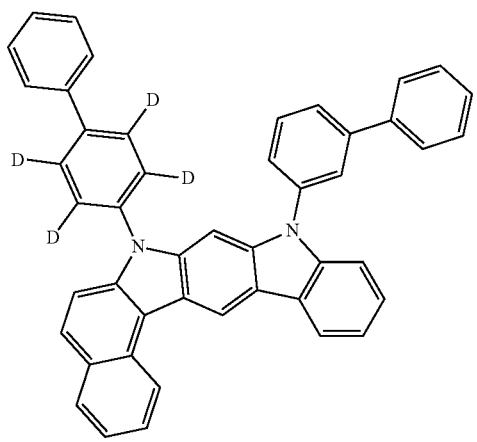
P-10
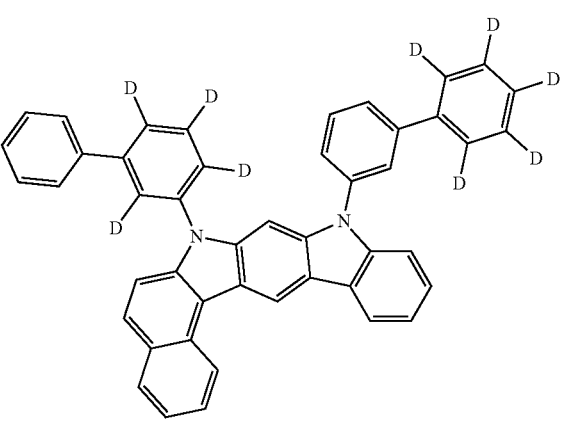

-continued
P-11
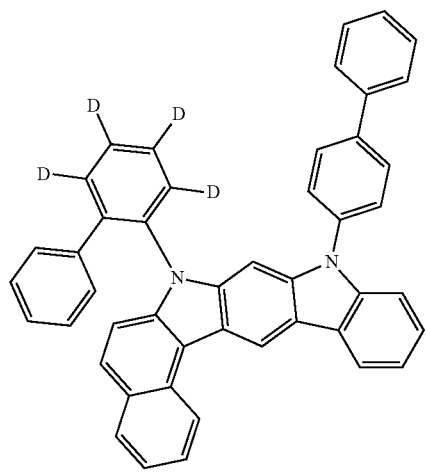
P-12
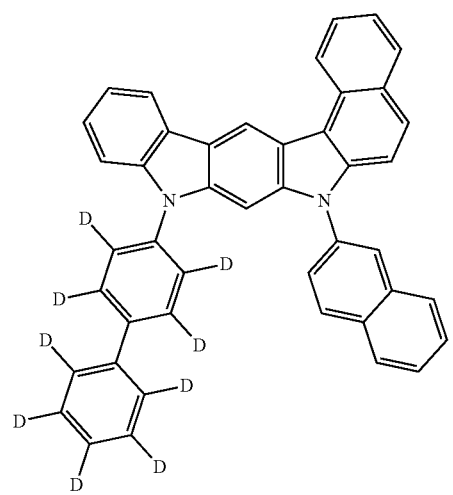
P-13
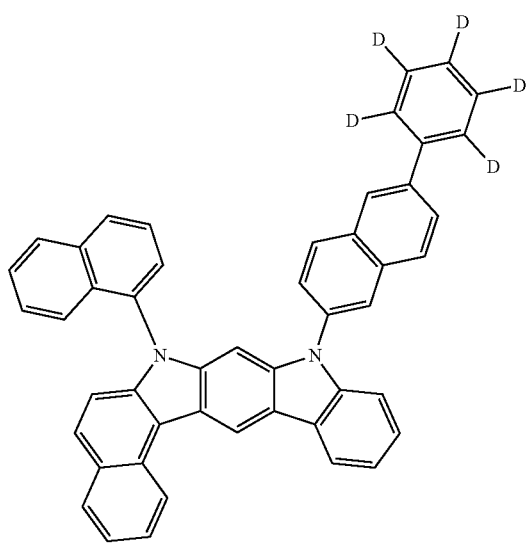
-continued
P-14
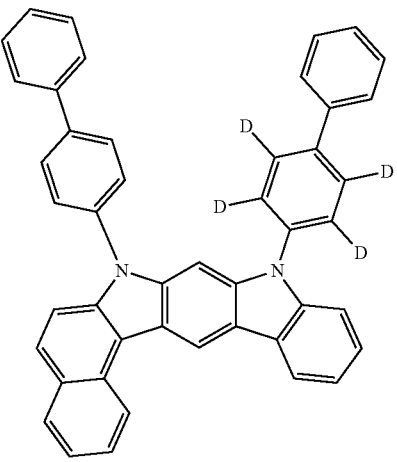
P-15
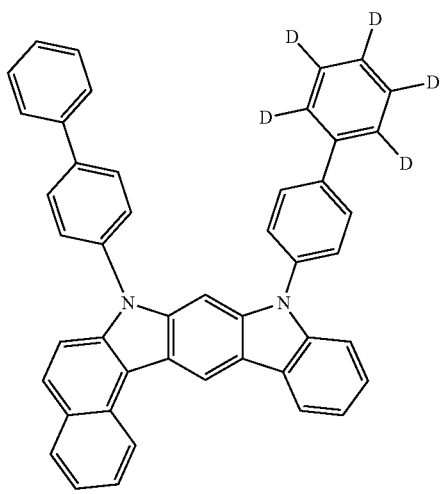
P-16
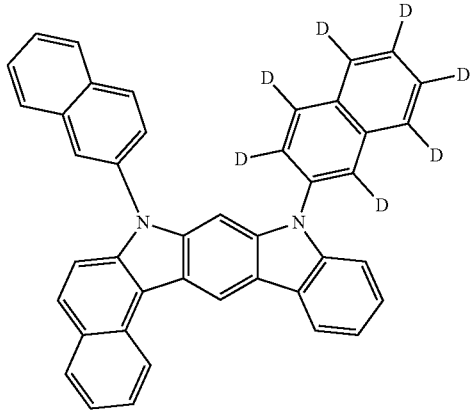

P-17
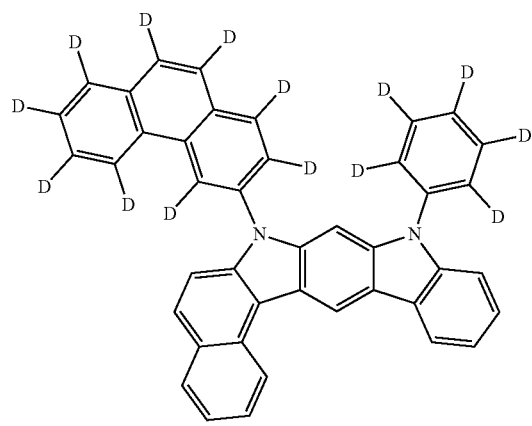
P-18
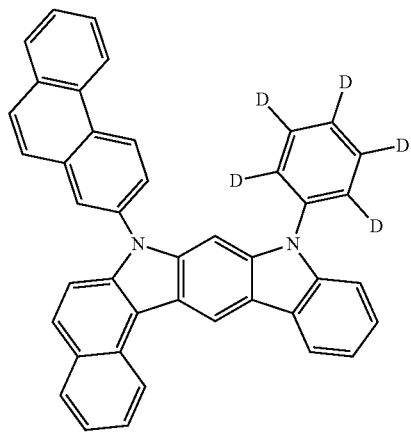
P-19
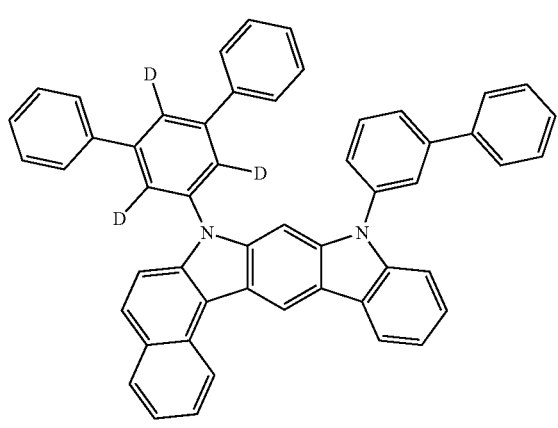
P-20
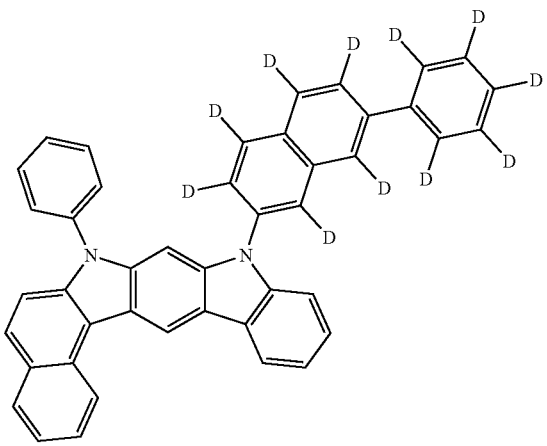
P-21
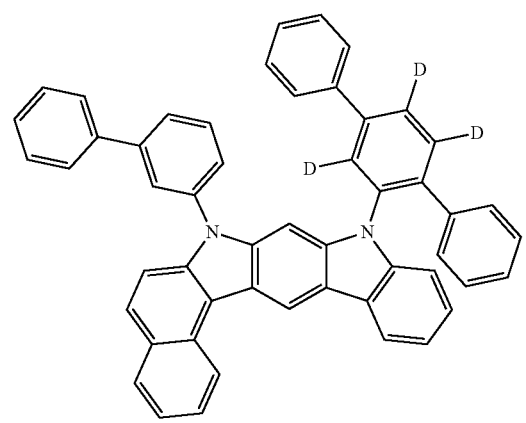
P-22
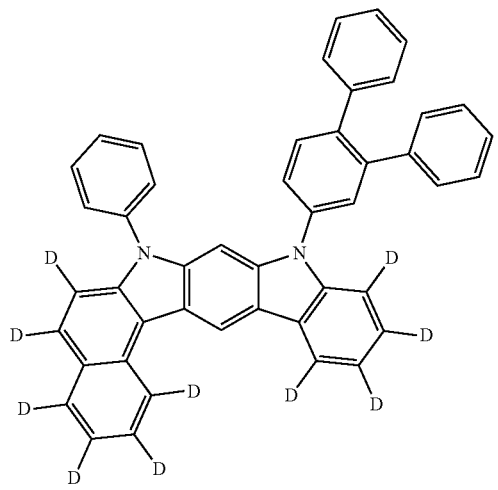

P-23
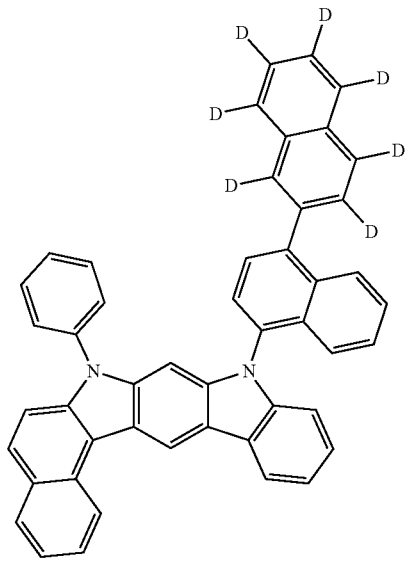
P-26
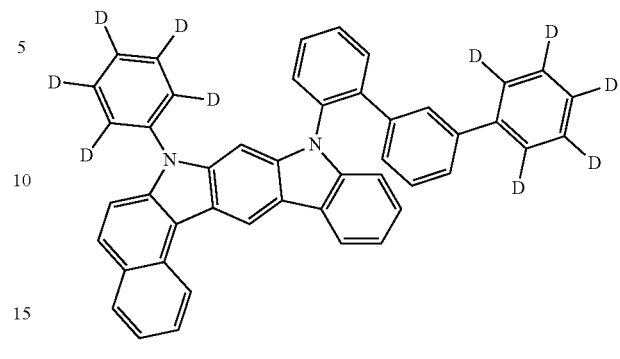
P-24
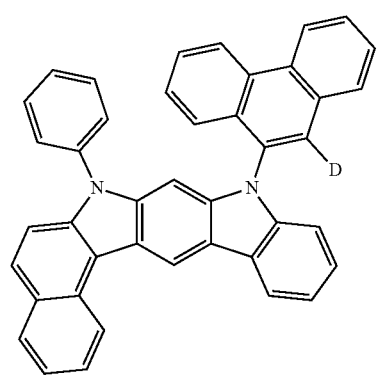
P-27
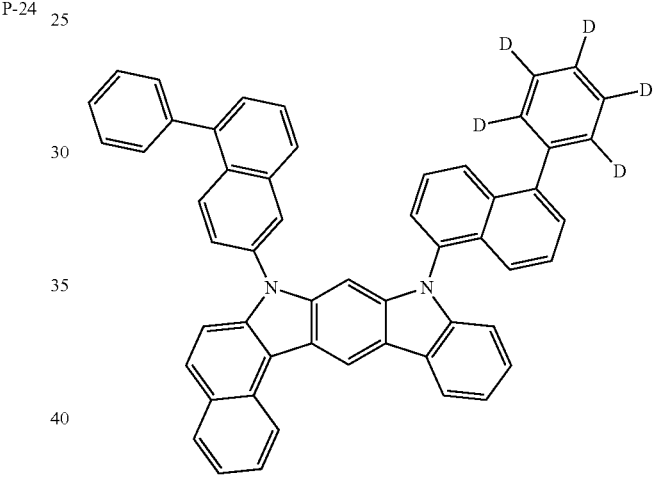
P-25
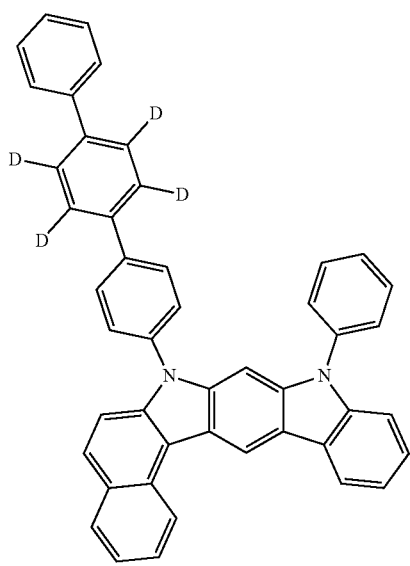
P-28
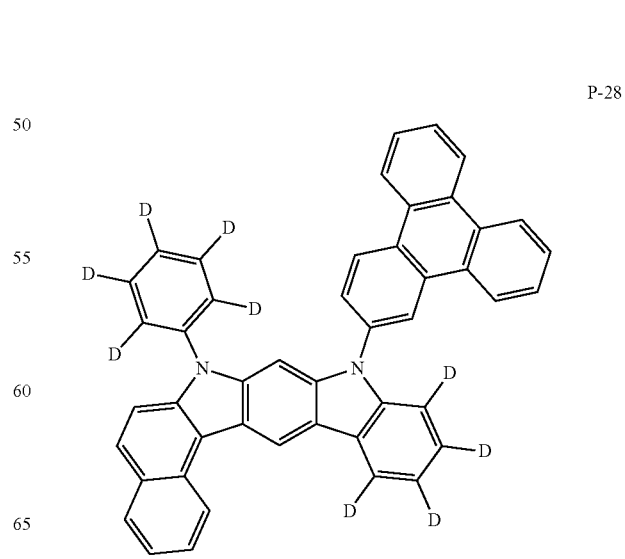

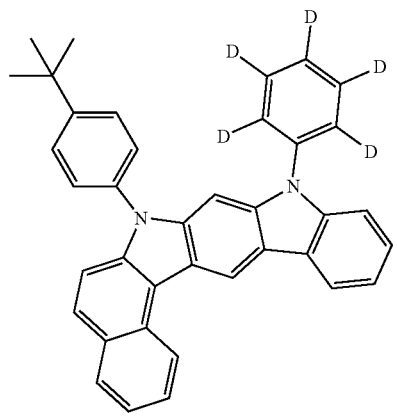
P-29
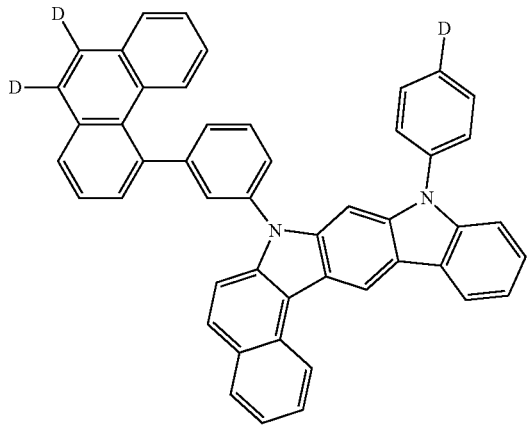
P-32
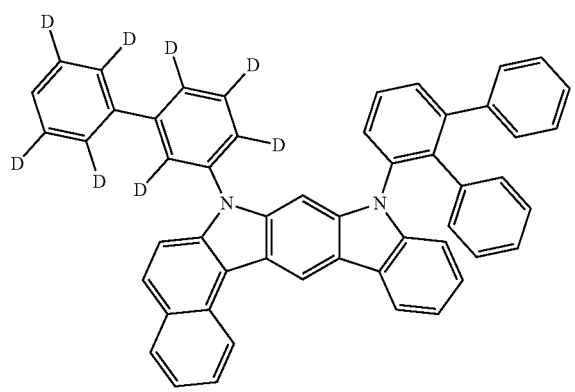
P-30
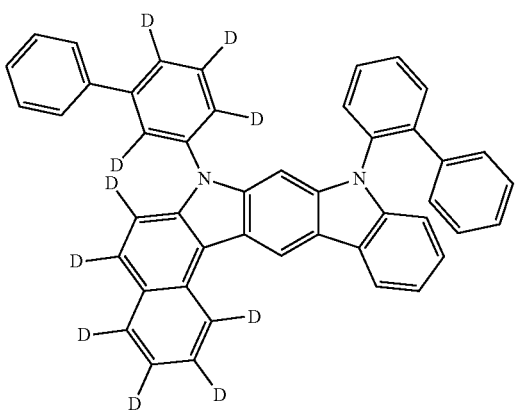
P-33
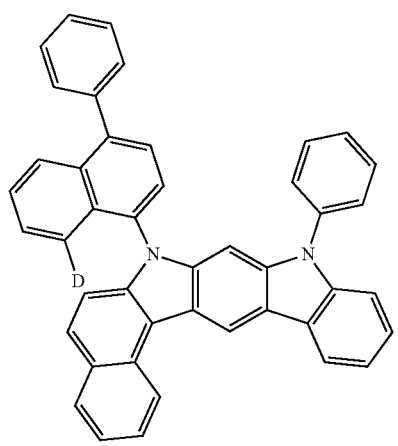
P-31
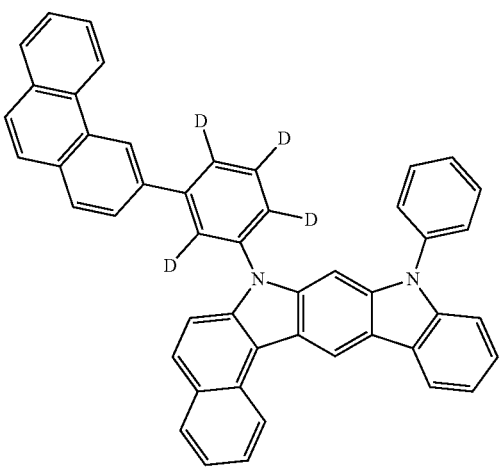
P-34

P-35
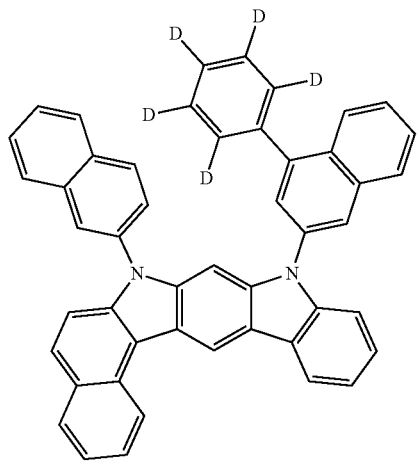
P-36
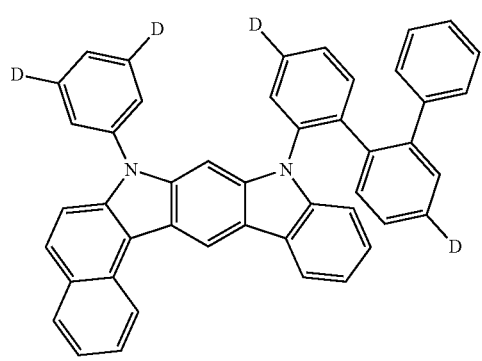
P-37
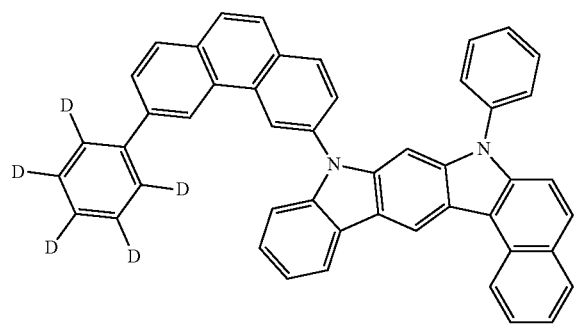
P-38
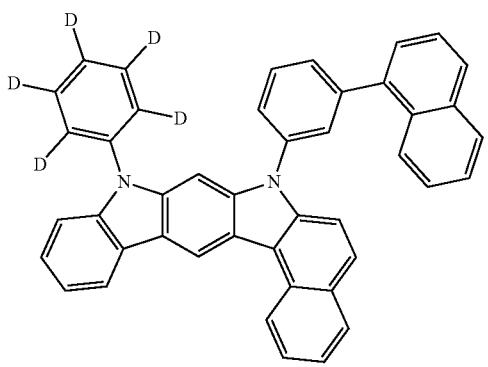
P-39
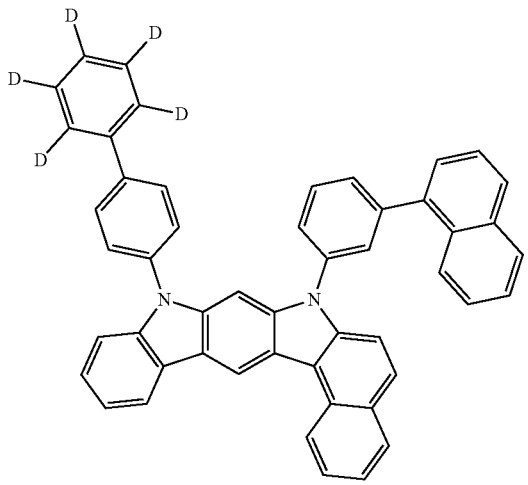
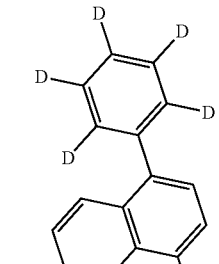
P-40
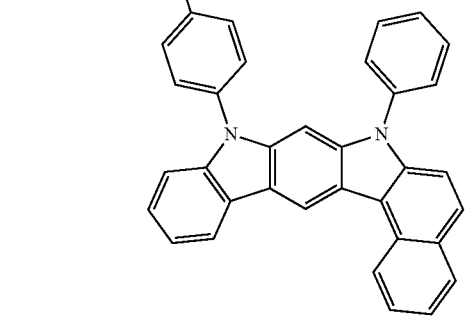
P-41
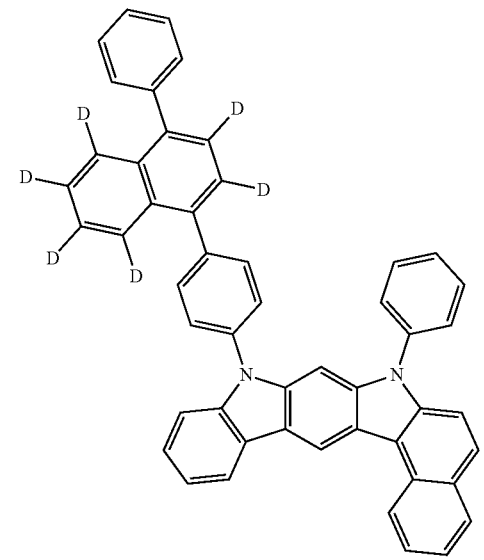

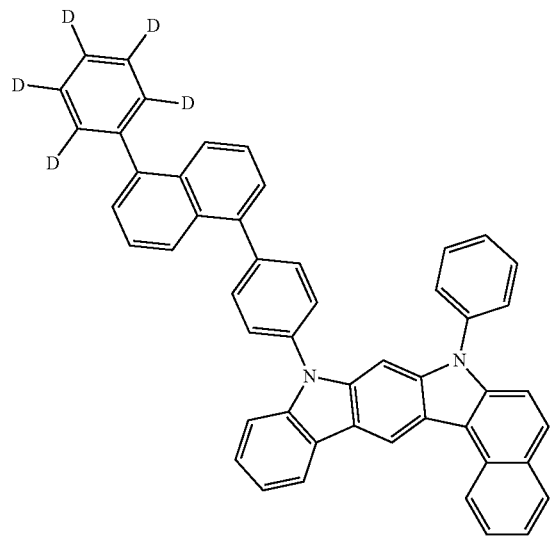
P-42
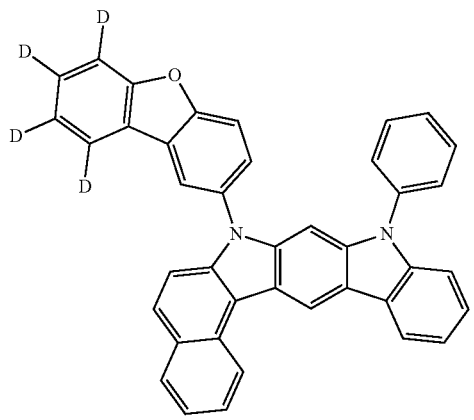
P-45
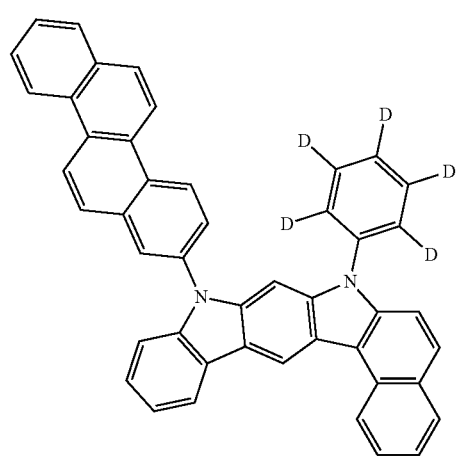
P-43
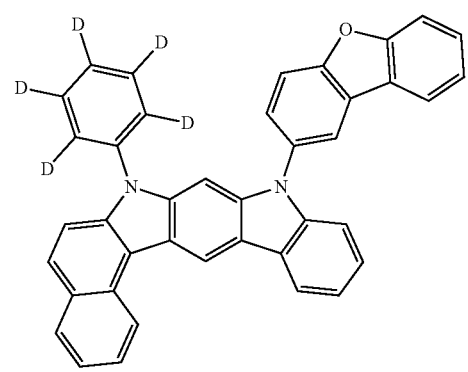
P-46
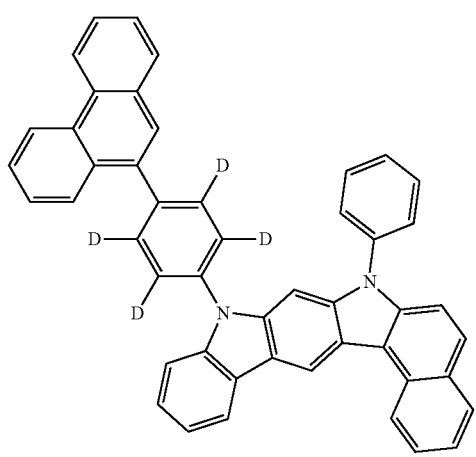
P-44
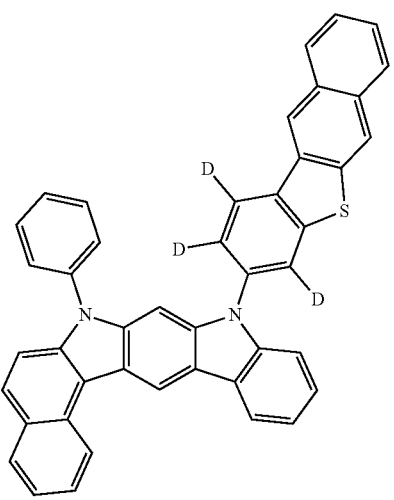
P-47

P-48
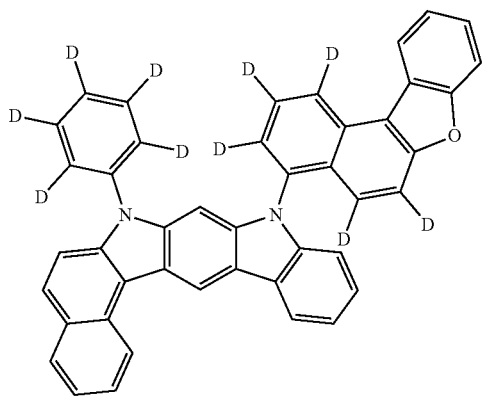
P-49
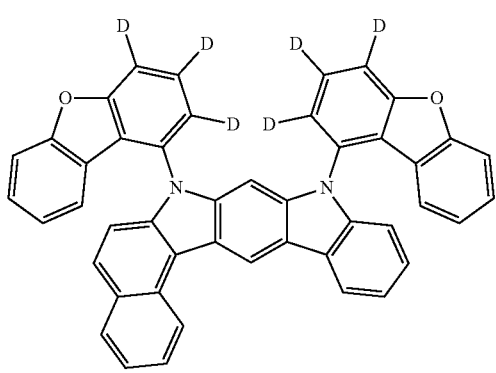
P-50
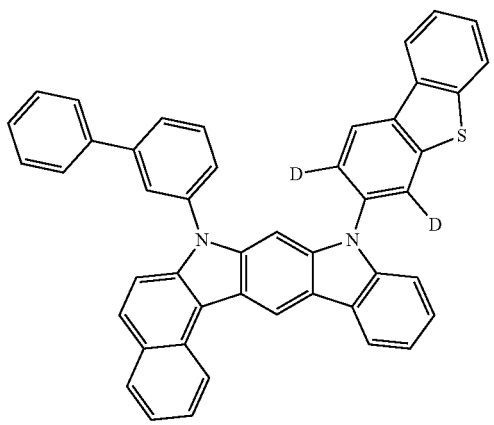
P-51
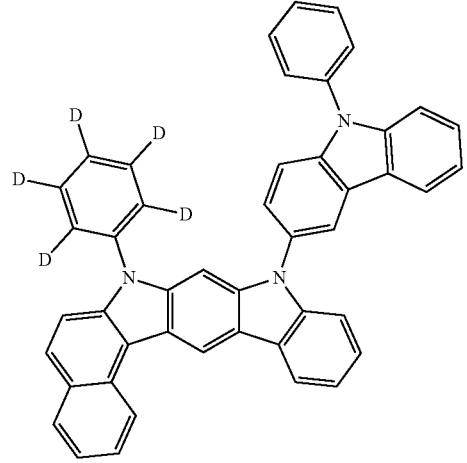
P-52
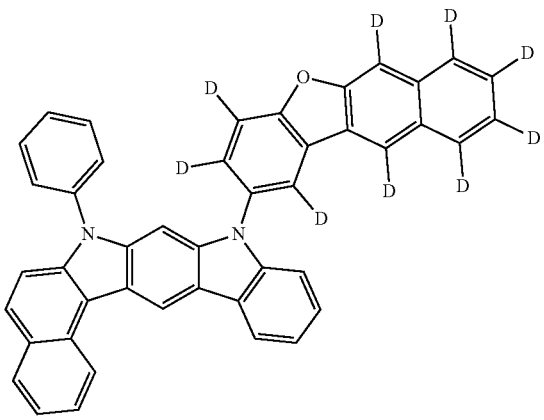
P-53
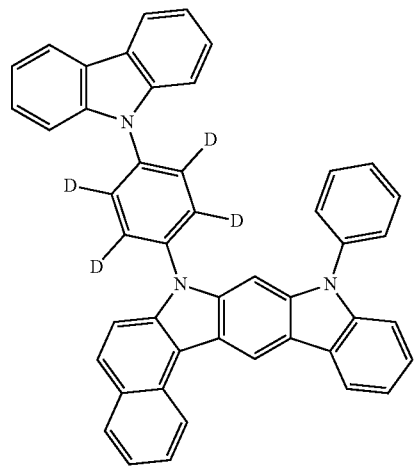
P-54
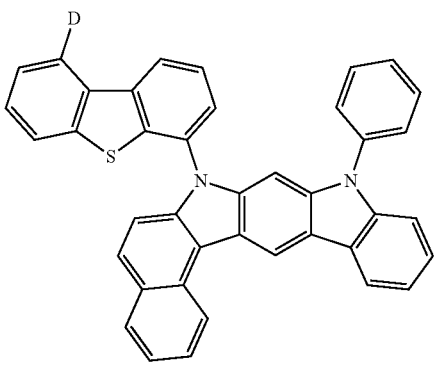

P-55
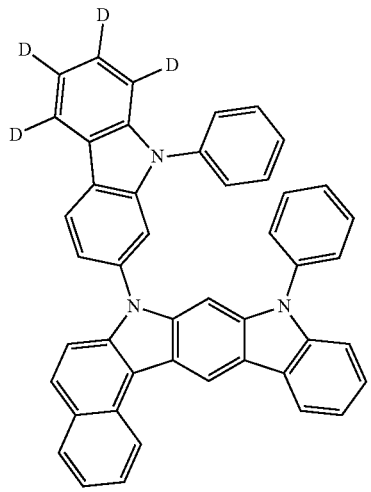
P-58
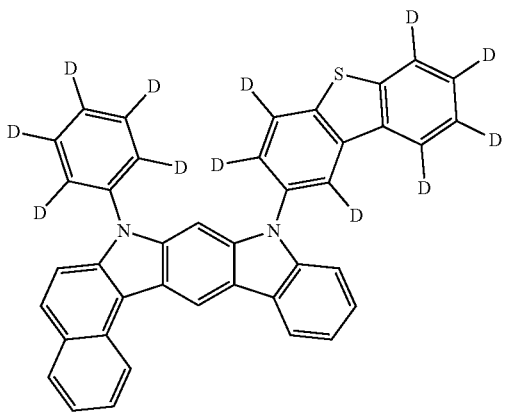
P-56
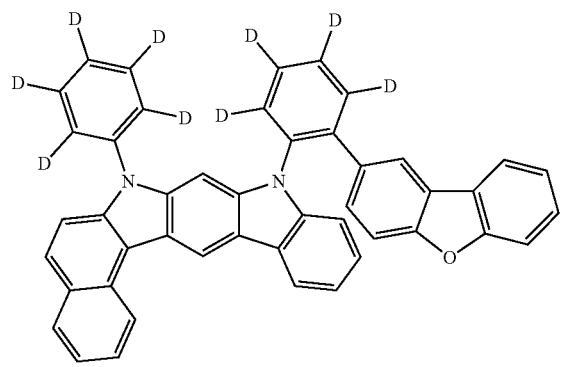
P-59
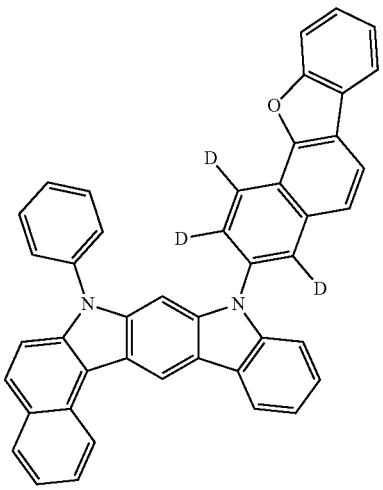
P-57
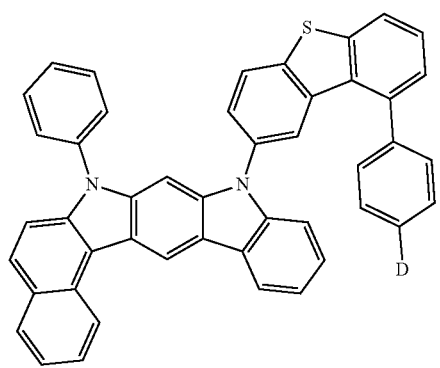
P-60
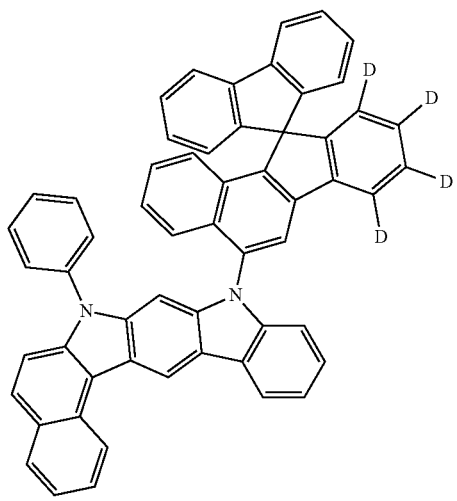

P-61
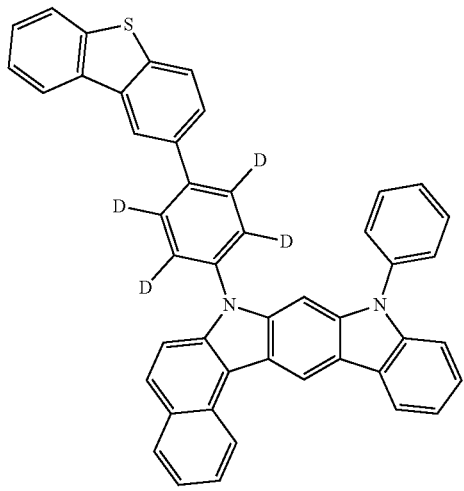
P-62
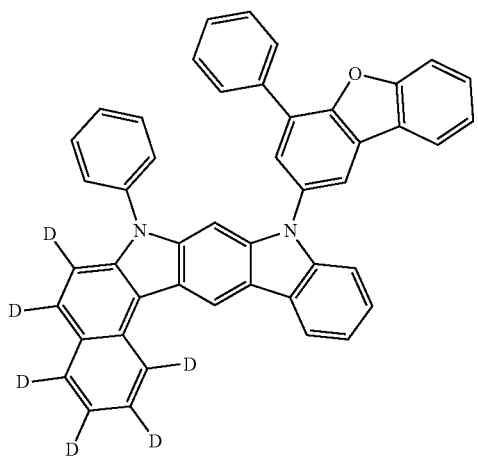
P-63
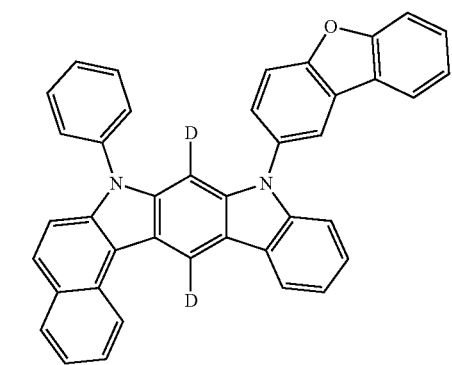
P-64
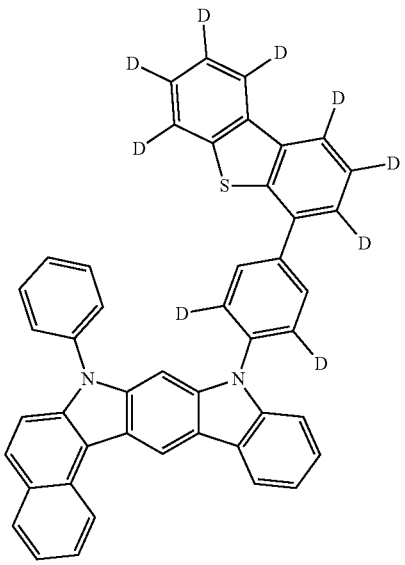
P-65
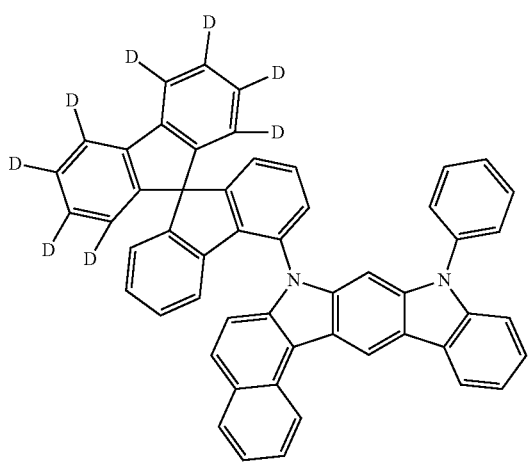
P-66
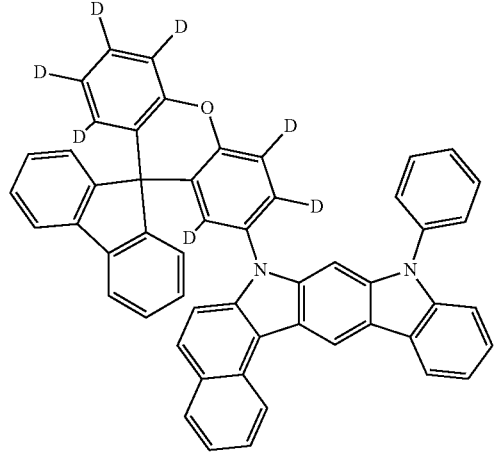

-continued
P-67
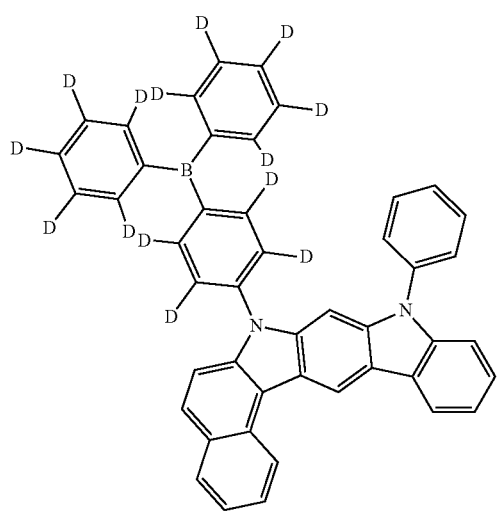
P-68
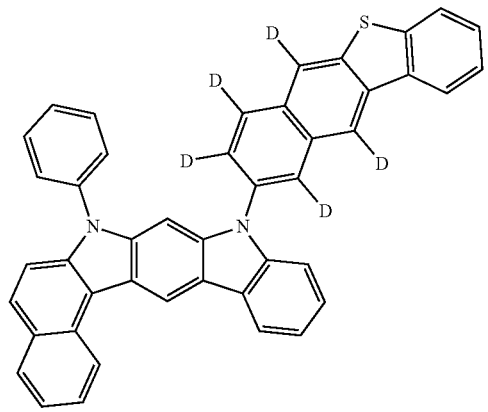
P-69
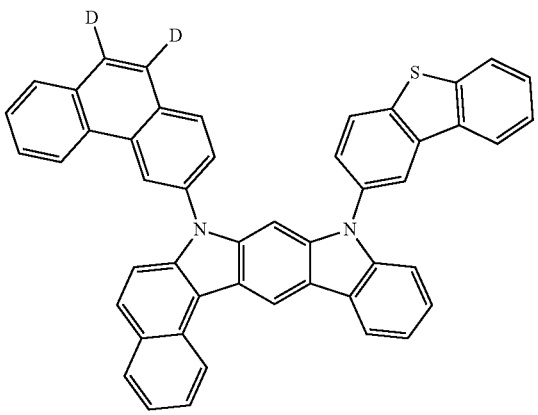
-continued
P-70
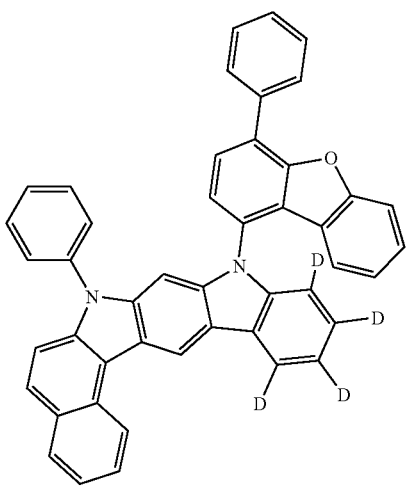
P-71
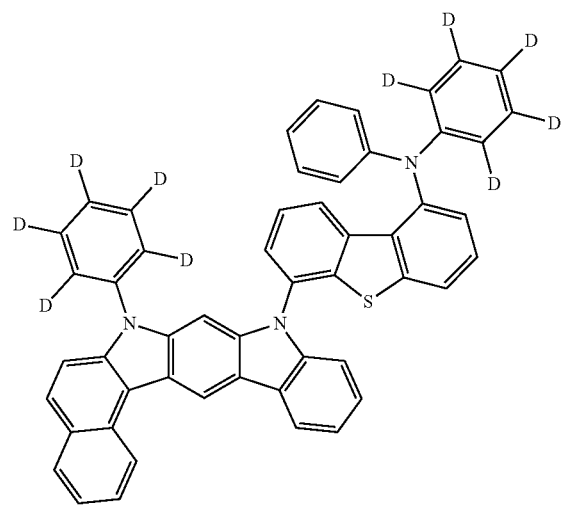
P-72
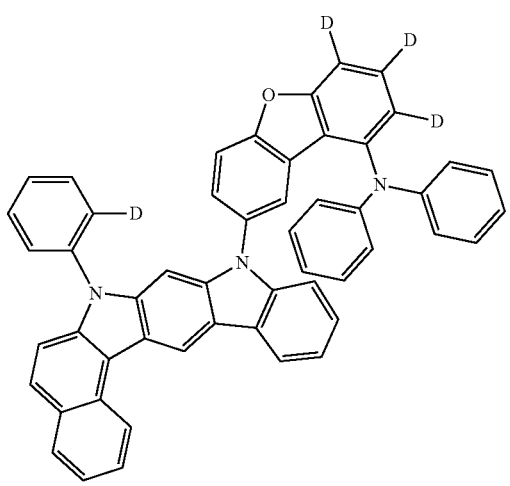

P-73
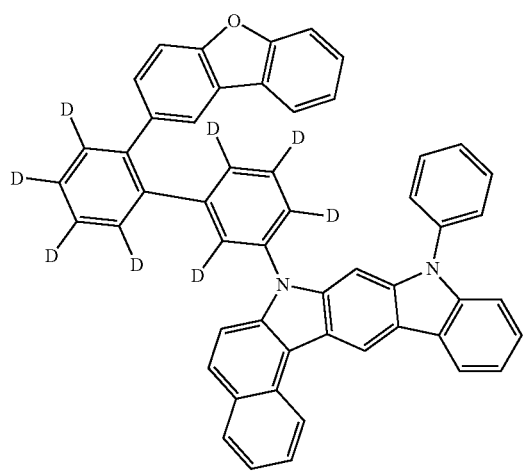
P-74
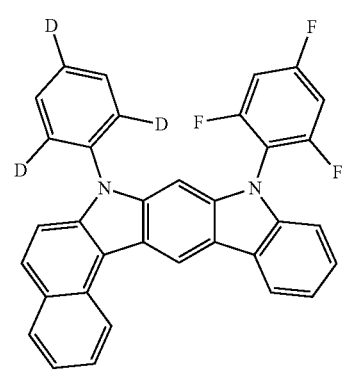
P-75
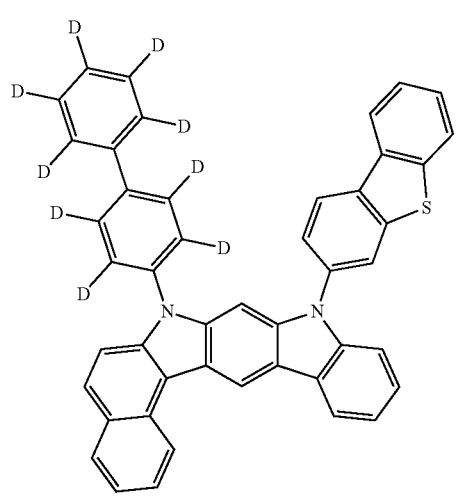
P-76
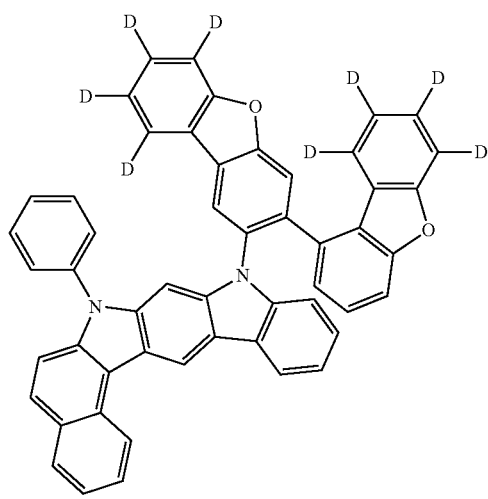
P-77
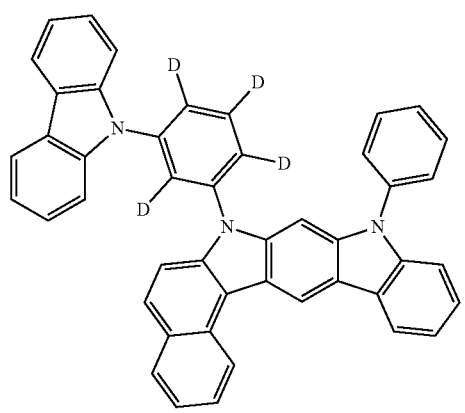
P-78
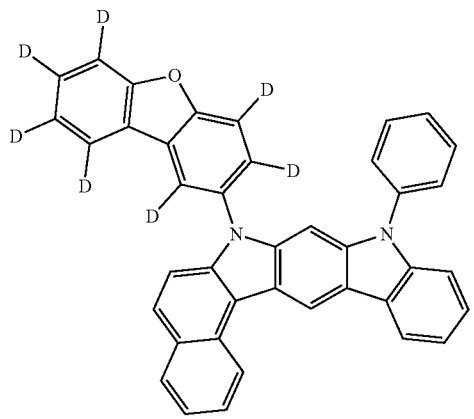

P-79 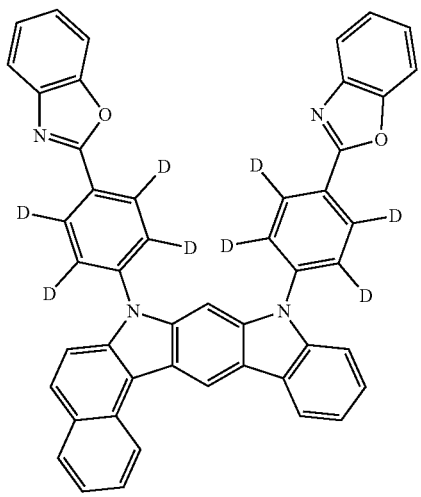
P-80 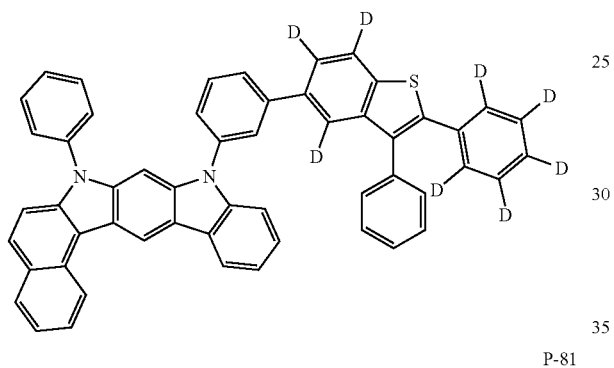
P-81 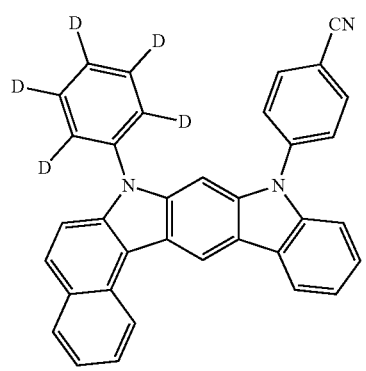
P-82 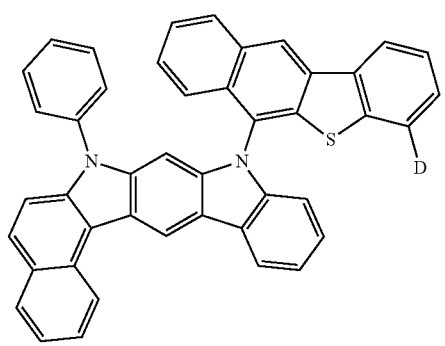
P-83 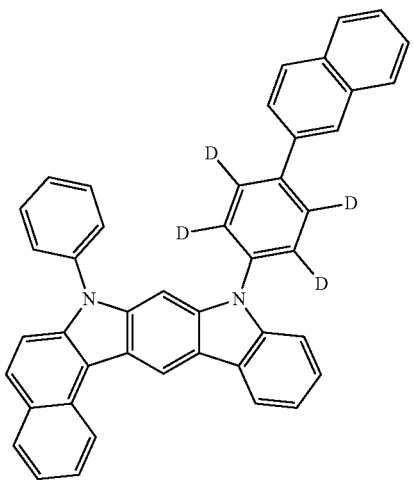
P-84 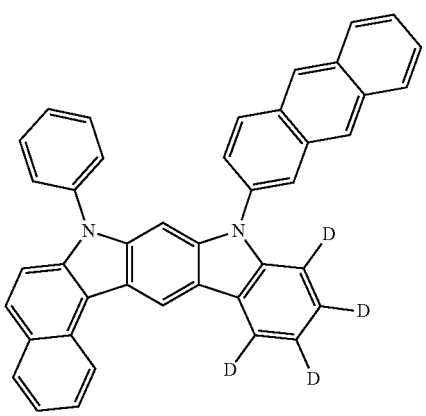
P-85 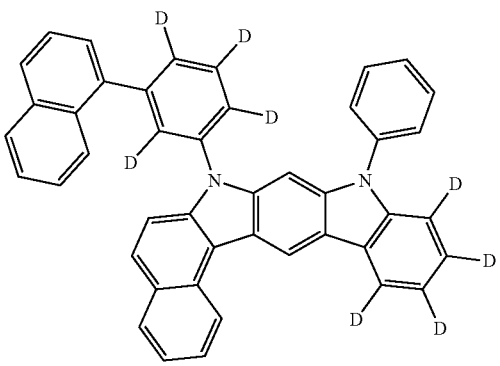

P-86
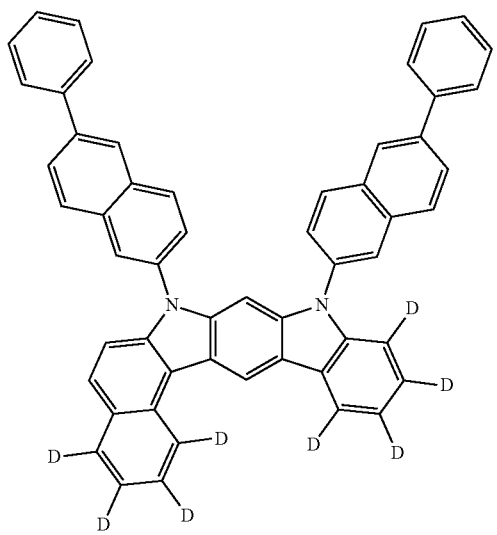

P-87
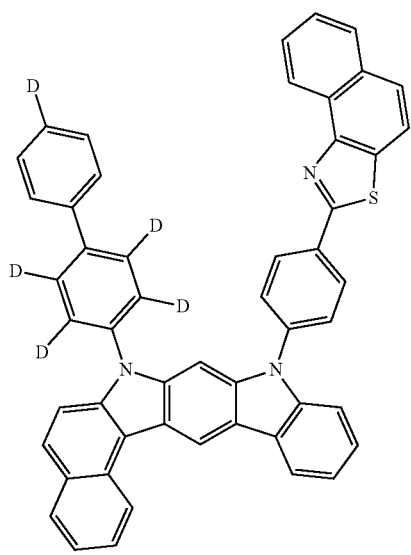

P-88
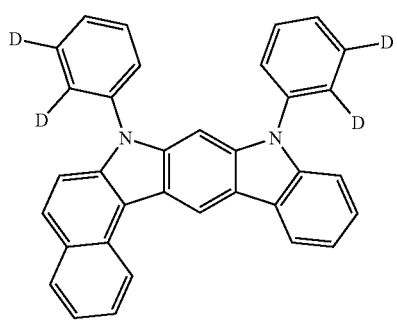

P-89
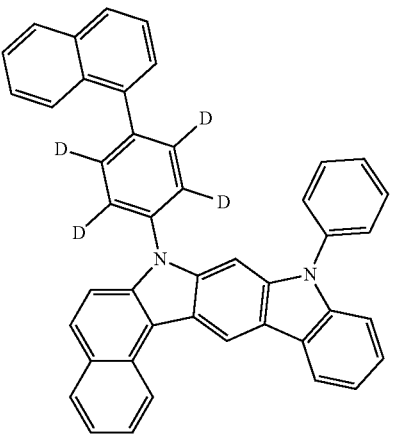

P-90
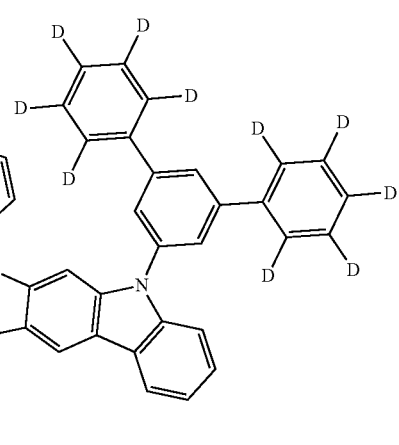

Referring to FIG. 1, the organic electronic element (100) according to the present invention includes a first electrode (110), a second electrode (170), and an organic material layer including a single compound or 2 or more compounds represented by Formula (1) between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
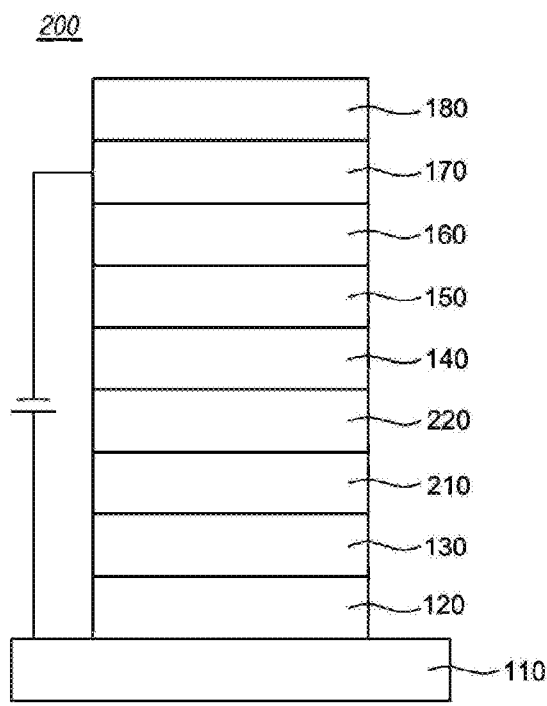

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting-auxiliary layer (220), a buffer layer (210), etc. and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting-auxiliary layer (220), electron transport auxiliary layer, the electron transport layer (150), and an electron injection layer (160), the emitting layer (140) or as a material for the light efficiency enhancing layer. Preferably, for example, the compound according to Formula (1) of the present invention may be used as a host material of the emitting layer.

Figure 3:
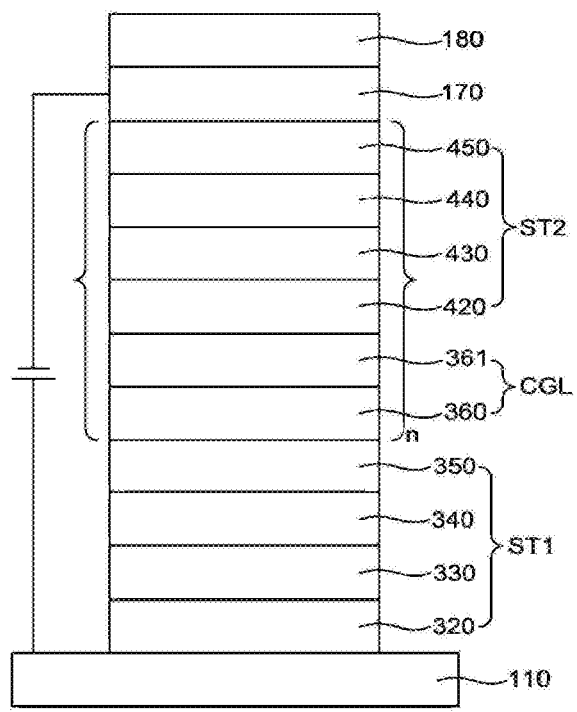
Figure 4:
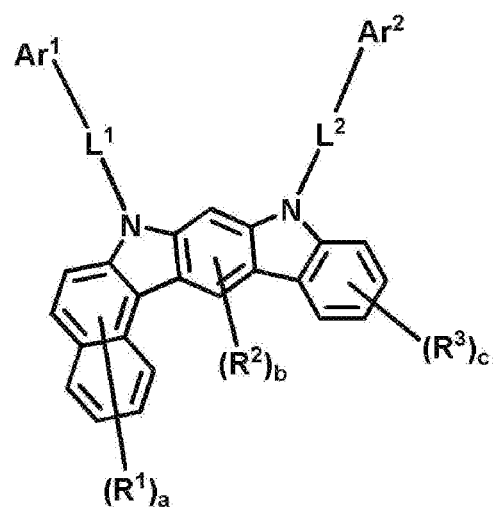
FIG. 4 shows a Formula according to an aspect of the present invention.

The organic material layer may include 2 or more stacks including a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer (120), the hole transport layer (130), the emitting layer (140), the electron transport layer (150) and the electron injection layer (160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electronic element comprising the compound as an emitting layer.

As another specific example, the same or different compounds of the compound represented by Formula (1) are mixed and used in the organic material layer.

Also, the present invention provides an emitting layer composition comprising the compound represented by Formula (1), and provides an organic electronic element including the emitting layer.

Also, the present invention provides an electronic device comprising a display device including the organic electronic element; and a control unit for driving the display device.

In another aspect, the organic electronic element is at least one of an organic electroluminescent device, an organic solar cell, an organic photoreceptor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, a synthesis example of the compound represented by Formula (1) of the present invention and a manufacturing example of an organic electronic element of the present invention will be described in detail with reference to Examples, but the present invention is not limited to the following Examples.

SYNTHESIS EXAMPLE

The compound (final products) represented by Formula (1) according to the present invention is synthesized by reacting Sub1 and Sub2 as follows, but is not limited thereto.

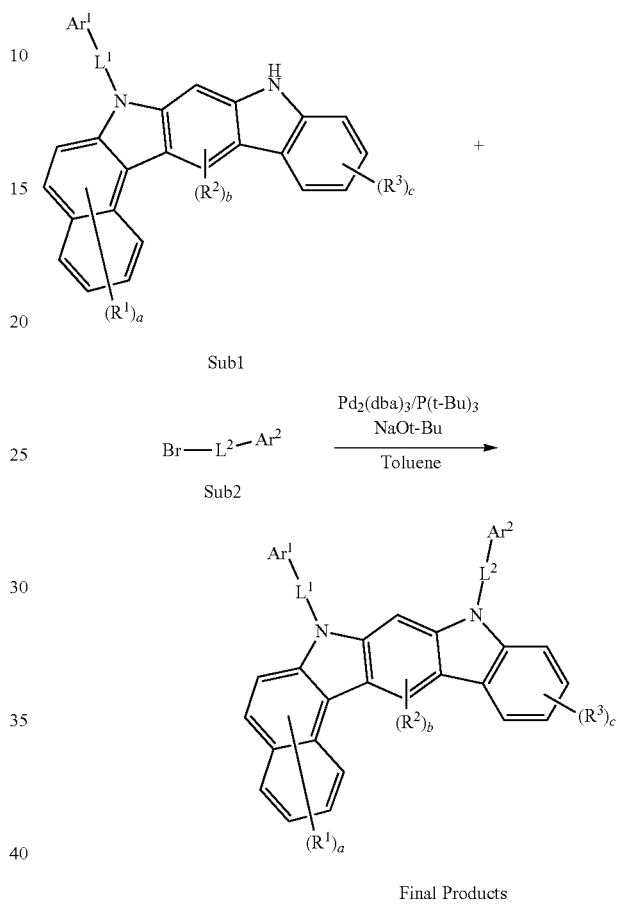

I. Synthesis of Sub1

1. Synthesis Example of Sub1-1

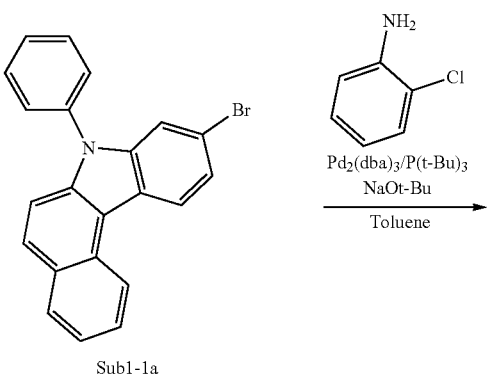

Sub1-1a

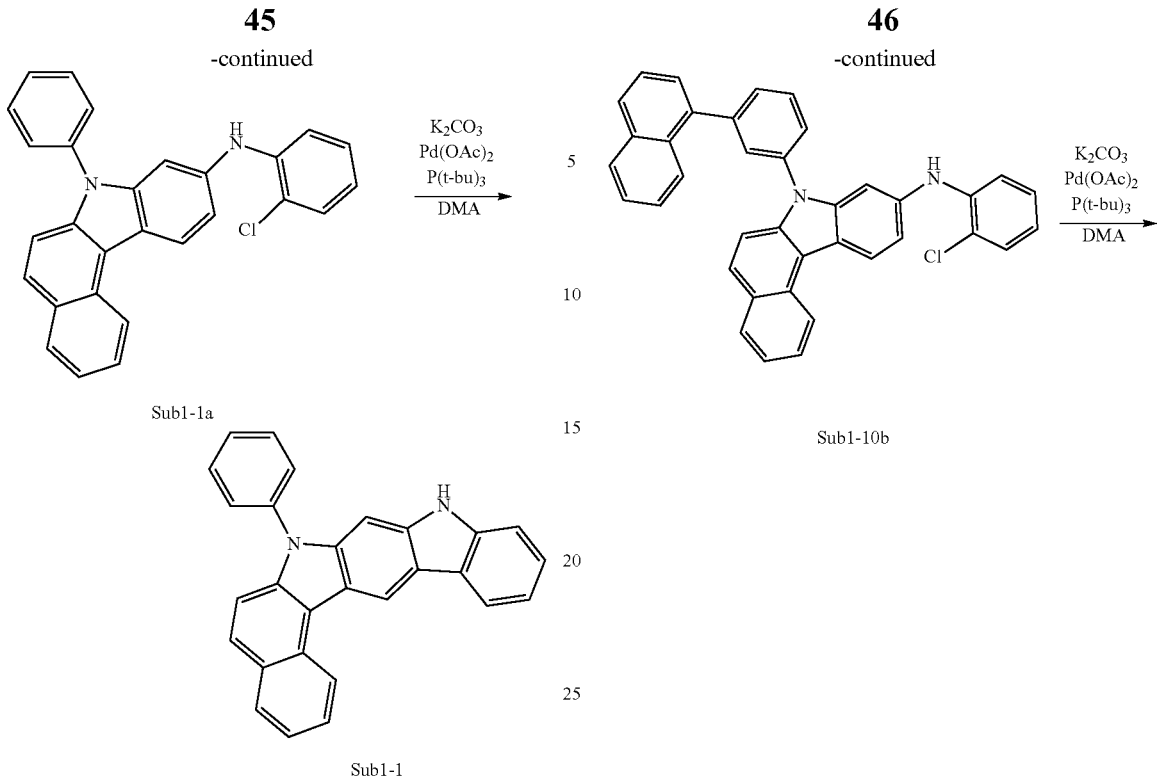

(1) Synthesis of Sub1-1b

Sub1-1a (50 g, 0.13 mol), 2-chloroaniline (17.1 g, 0.13 mol), Pd$_2$(dba)$_3$ (3.7 g, 0.004 mol), 50% P(t-Bu)$_3$ (3.3 g, 0.008 mol), NaOt-Bu (38.8 g, 0.40 mol) were added to toluene (270 ml) and stirred at 90° C. When the reaction was completed, the reaction solvent was removed, and the concentrated organic material was separated using a silica gel column or recrystallization method to obtain 42 g (74.8%) of Sub1-1 b.

(2) Synthesis of Sub1-1

Pd(OAc)$_2$ (0.64 g, 0.003 mol), P(t-Bu)$_3$ (2.3 g, 0.006 mol), K$_2$CO$_3$ (39.7 g, 0.29 mol), DMA (190 ml) were added to Sub1-1b (40 g, 0.10 mol) and stirred at 170° C. for 12 hours. When the reaction is complete, the reaction solvent is removed and put into ice water. Then, the precipitated solid was separated using a silica gel column or recrystallization method to obtain 25 g (68.4%) of the product Sub1-1.

2. Synthesis of Sub1-10

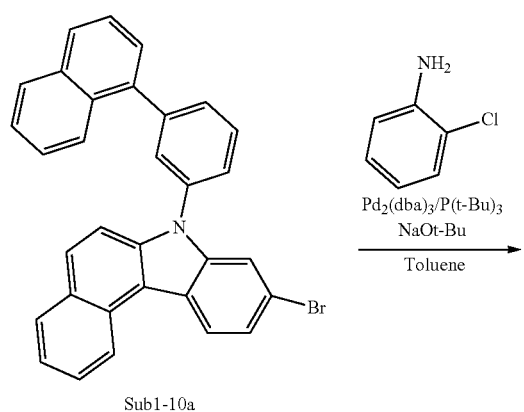

(1) Synthesis of Sub1-10b

Sub1-10a (50 g, 0.10 mol), 2-chloroaniline (12.8 g, 0.10 mol), Pd$_2$(dba)$_3$ (2.8 g, 0.003 mol), 50% P(t-Bu)$_3$ (2.8 g, 0.003 mol), NaOt-Bu (29 g, 0.30 mol) were added to toluene (200 ml) and stirred at 90° C. When the reaction was completed, 48 g (87.7%) of the product Sub1-10b was obtained by using the separation method for Sub1-1b described above.

(2) Synthesis of Sub1-10

Pd(OAc)$_2$ (0.37 g, 0.002 mol), P(t-Bu)$_3$ (1.3 g, 0.003 mol), K$_2$CO$_3$ (22.8 g, 0.17 mol), DMA (110 ml) were added to Sub1-10b (30 g, 0.06 mol) and stirred at 170° C. for 12 hours. When the reaction was completed, 21 g (75%) of the product Sub1-10 was obtained by using the separation method of Sub1-1 described above.

3. Synthesis of Sub1-20

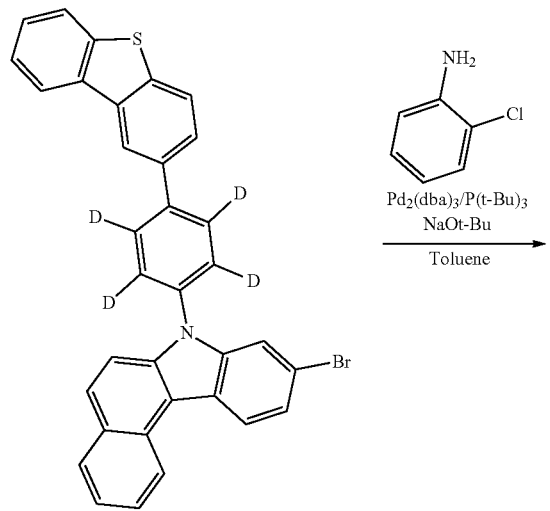

Sub1-20a

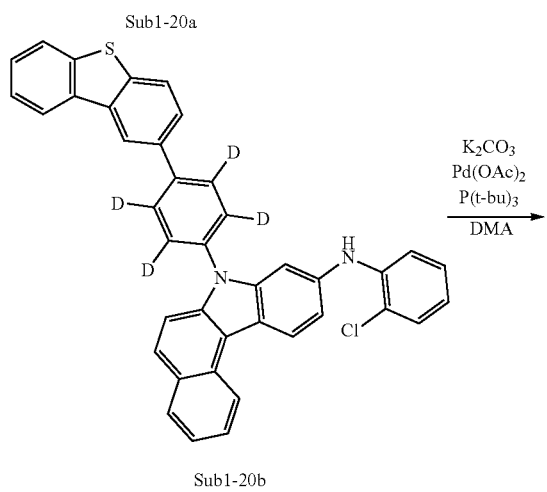

Sub1-20b

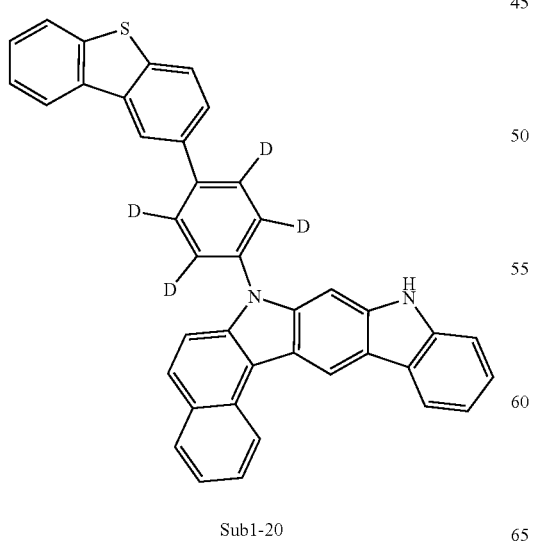

Sub1-20

(1) Synthesis of Sub1-20b

Sub1-20a (50 g, 0.09 mol), 2-chloroaniline (11.4 g, 0.09 mol), Pd$_2$(dba)$_3$ (2.5 g, 0.003 mol), 50% P(t-Bu)$_3$ (2.2 g, 0.005 mol), NaOt-Bu (25.9 g, 0.30 mol) were added to toluene (180 ml) and stirred at 90° C. When the reaction was completed, 50 g (92.2%) of the product Sub1-20b was obtained by using the separation method for Sub1-1b described above.

(2) Synthesis of Sub1-20

Pd(OAc)$_2$ (0.56 g, 0.002 mol), P(t-Bu)$_3$ (2.0 g, 0.005 mol), K$_2$CO$_3$ (34.3 g, 0.25 mol), DMA (165 ml) were added to Sub1-20b (50 g, 0.08 mol) and stirred at 170° C. for 12 hours. When the reaction was completed, 29 g (61.8%) of the product Sub1-20 was obtained by using the separation method of Sub1-1 described above.

4. Synthesis of Sub1-31

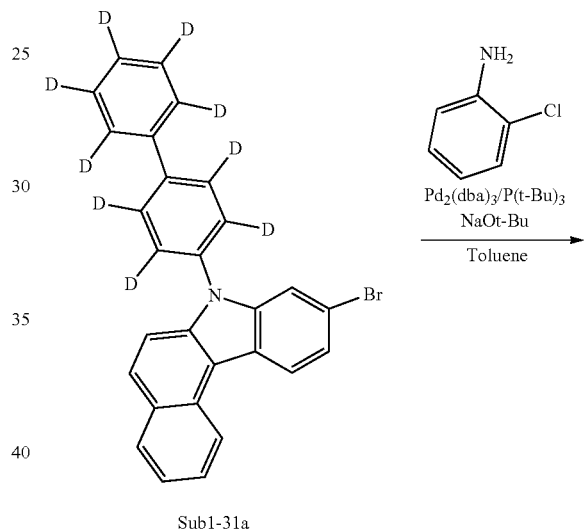

Sub1-31a

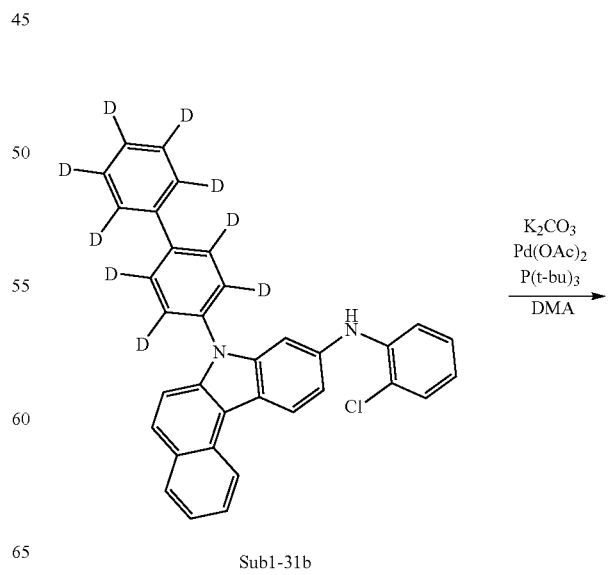

Sub1-31b

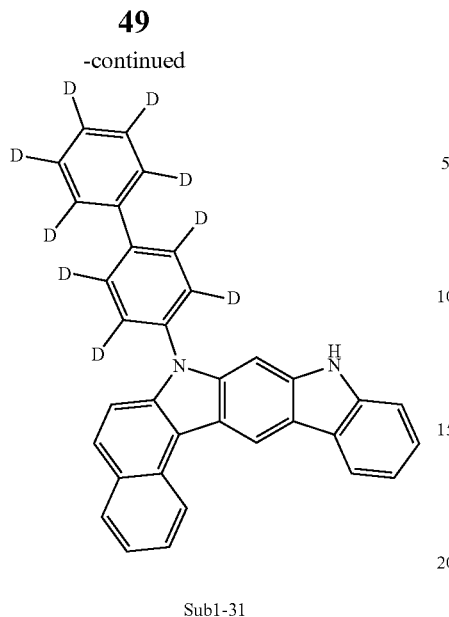

Sub1-31

(1) Synthesis of Sub1-31b

Sub1-31a (25 g, 0.05 mol), 2-chloroaniline (6.9 g, 0.05 mol), Pd₂(dba)₃ (1.5 g, 0.002 mol), 50% P(t-Bu)₃ (1.3 g, 0.003 mol), NaOt-Bu (15.8 g, 0.16 mol) were added to toluene (110 ml) and stirred at 90° C. When the reaction was completed, 23 g (83.4%) of the product Sub1-31 b was obtained by using the separation method for Sub1-1 b described above.

(2) Synthesis of Sub1-31

Sub1-31b (30 g, 0.06 mol)0-‖ Pd(OAc)₂ (0.40 g, 0.002 mol), P(t-Bu)₃ (1.4 g, 0.004 mol), K₂CO₃ (24.7 g, 0.18 mol), DMA (120 ml) were added and stirred at 170° C. for 12 hours. When the reaction was completed, 18 g (64.8%) of the product Sub1-31 was obtained by using the separation method for Sub1-1 described above.

5. Synthesis of Sub1-46

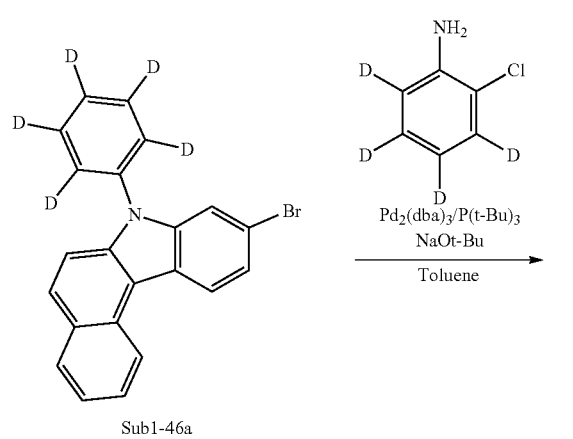

Sub1-46a

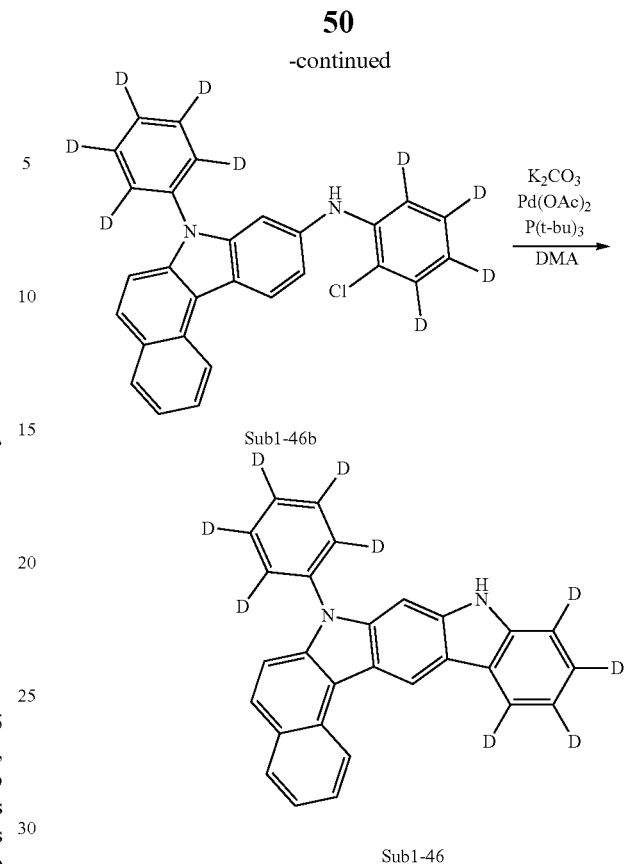

Sub1-46b

Sub1-46

(1) Synthesis of Sub1-46b

Sub1-46a (40 g, 0.11 mol), 2-chlorobenzen-3,4,5,6-d4-amine (13.9 g, 0.11 mol), Pd₂(dba)₃ (2.9 g, 0.003 mol), 50% P(t-Bu)₃ (2.6 g, 0.006 mol), NaOt-Bu (30.6 g, 0.32 mol) were added to toluene (220 ml) and stirred at 90° C. When the reaction was completed, 38 g (83.9%) of the product Sub1-46b was obtained by using the separation method for Sub1-1b described above.

(2) Synthesis of Sub1-46

Sub1-46b (35 g, 0.08 mol)0-‖ Pd(OAc)₂ (0.55 g, 0.002 mol), P(t-Bu)₃ (2.0 g, 0.005 mol), K₂CO₃ (34 g, 0.25 mol), DMA (160 ml) were added and stirred at 170° C. for 12 hours. When the reaction was completed, 22 g (68.8%) of the product Sub1-46 was obtained by using the separation method for Sub1-1 described above.

The compound belonging to Sub1 may be a compound as follows, but is not limited thereto, and Table 1 below shows FD-MS (Field Desorption-Mass Spectrometry) values of compounds belonging to Sub1-1 to Sub1-50.

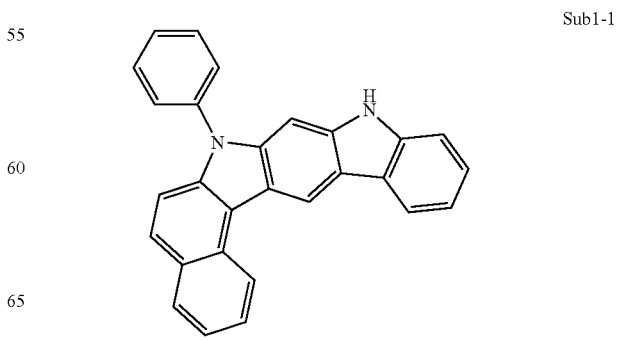

Sub1-1

Sub1-2
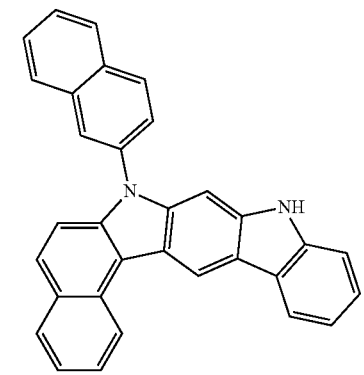
Sub1-3
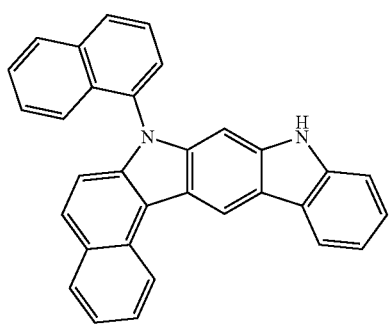
Sub1-4
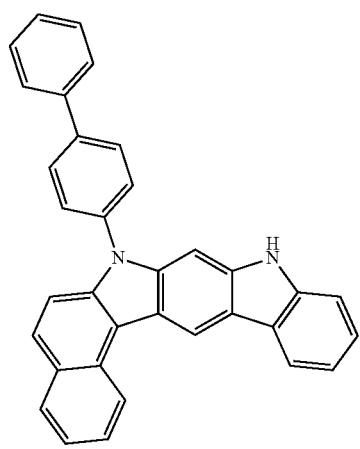
Sub1-5
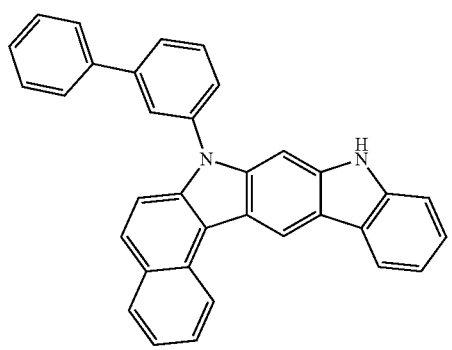
Sub1-6
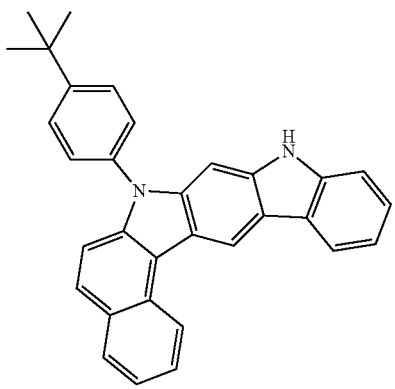
Sub1-7
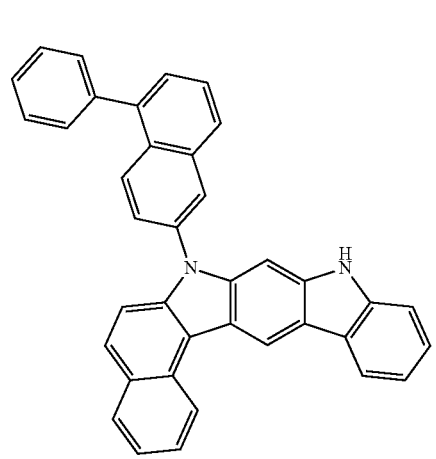
Sub1-8
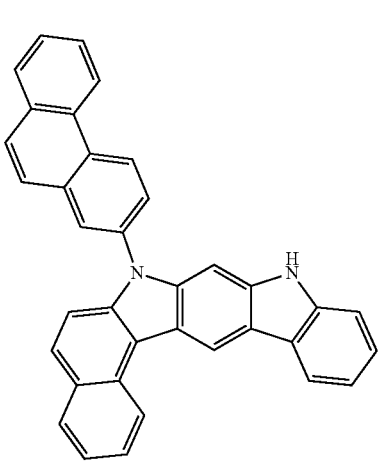

Sub1-9
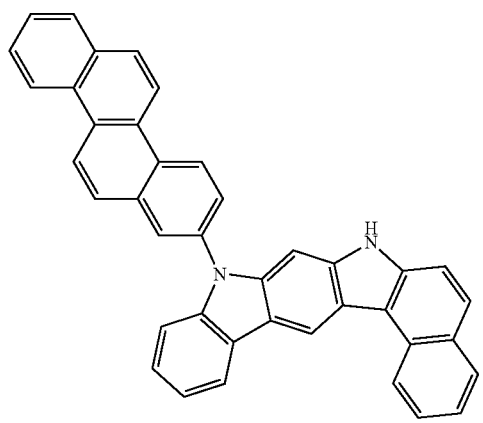
Sub1-10
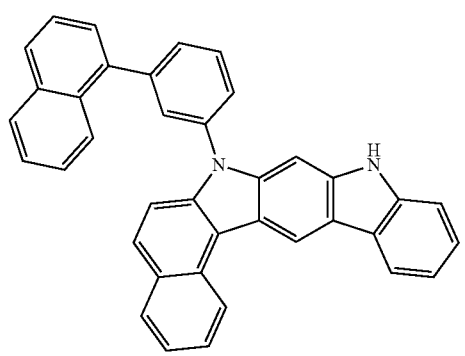
Sub1-11
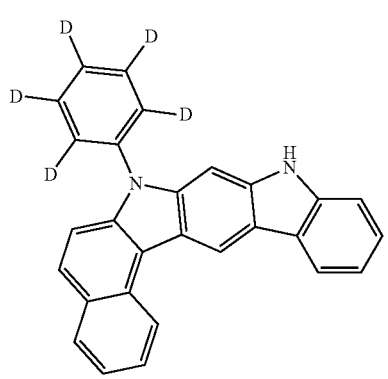
Sub1-12
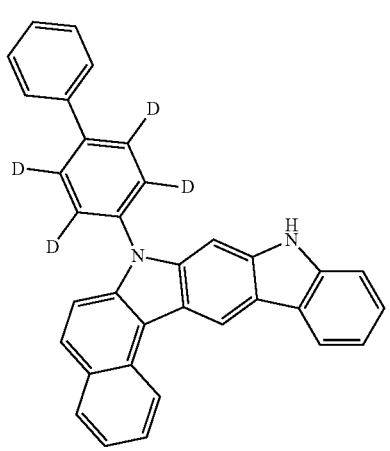
Sub1-13
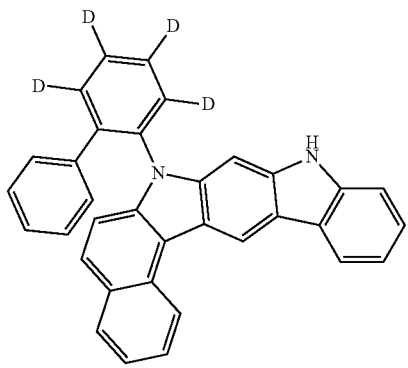
Sub1-14
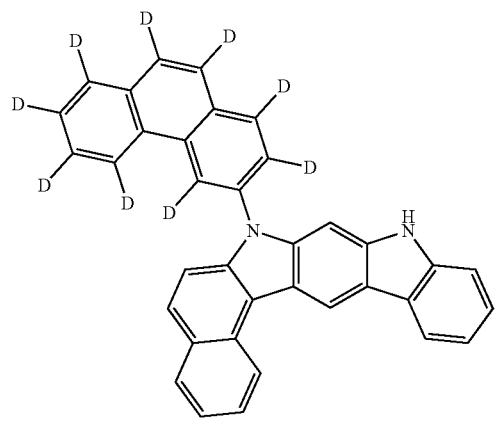
Sub1-15
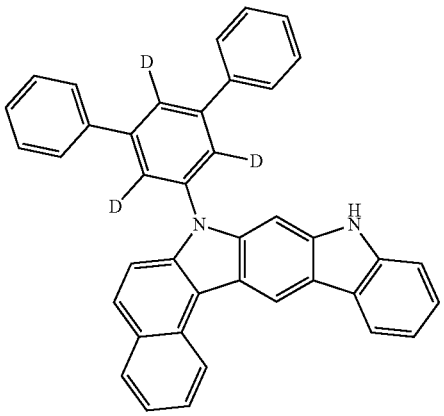
Sub1-16
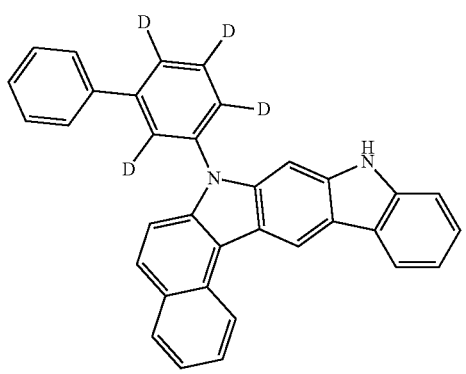

Sub1-17
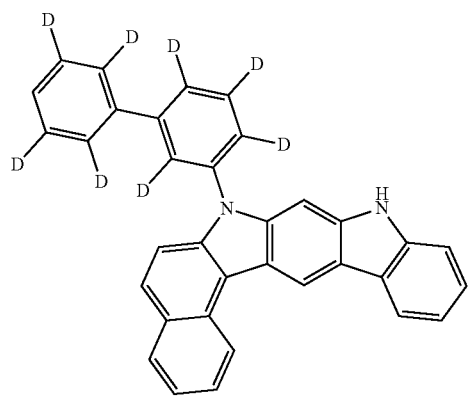
Sub1-18
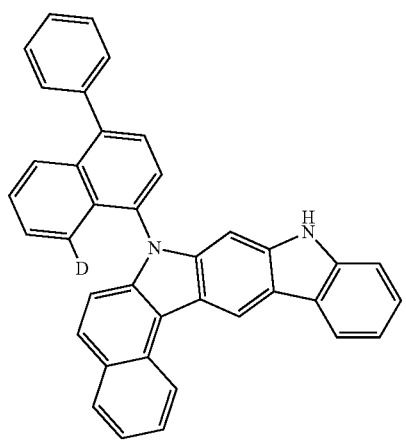
Sub1-19
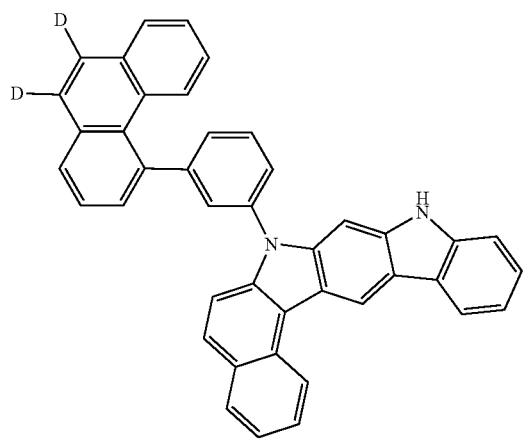
Sub1-20
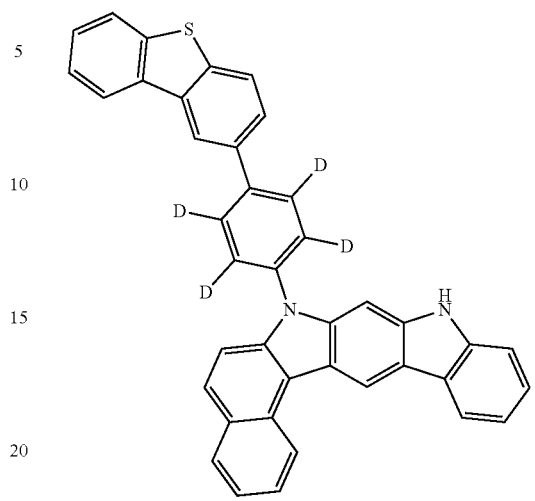
Sub1-21
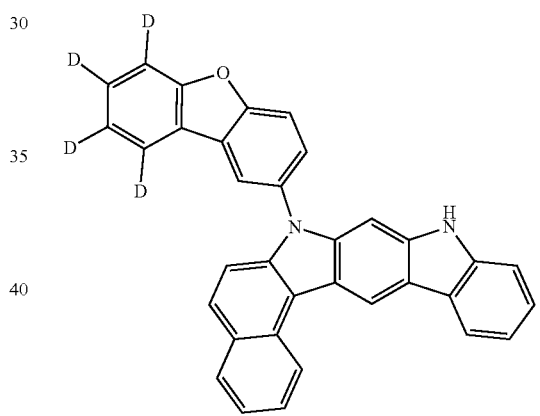
Sub1-22
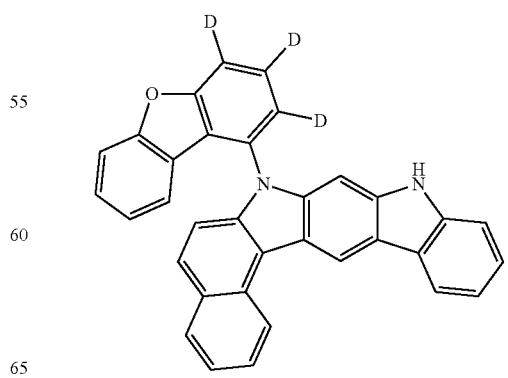

Sub1-23
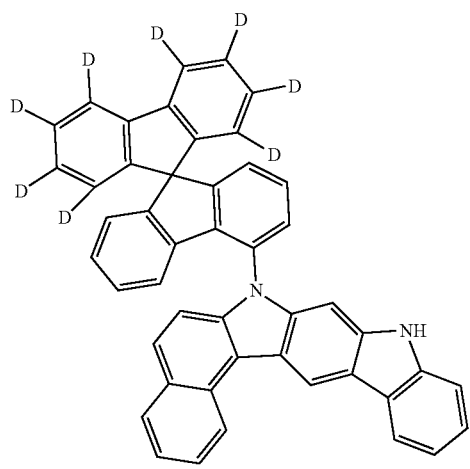
Sub1-24
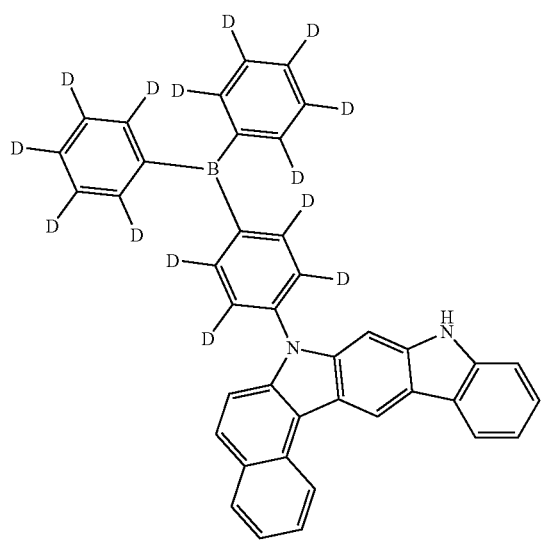
Sub1-25
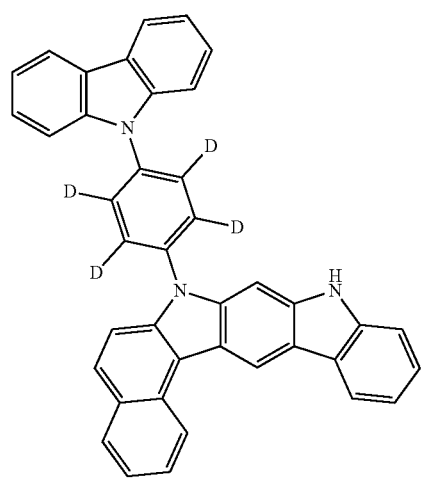
Sub1-26
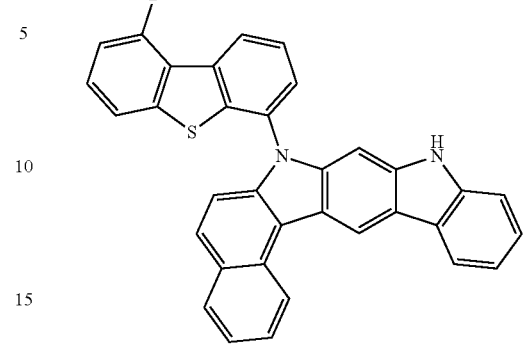
Sub1-27
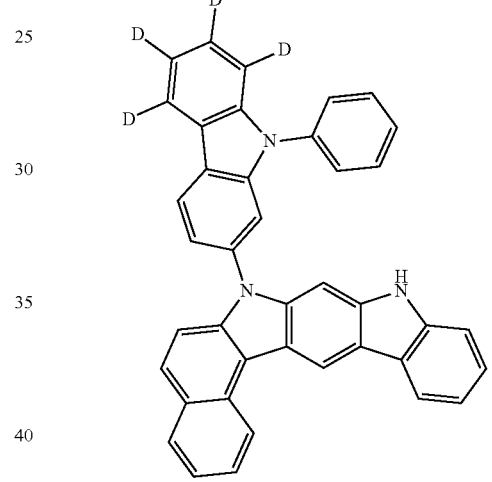
Sub1-28
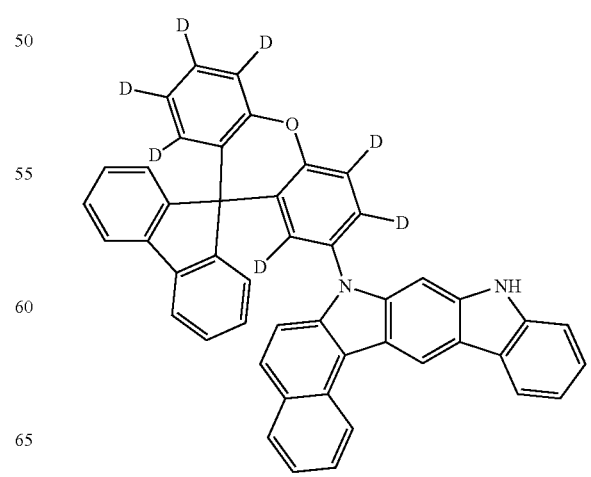

Sub1-29
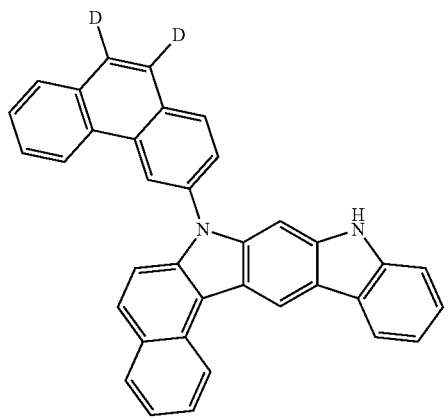
Sub1-30
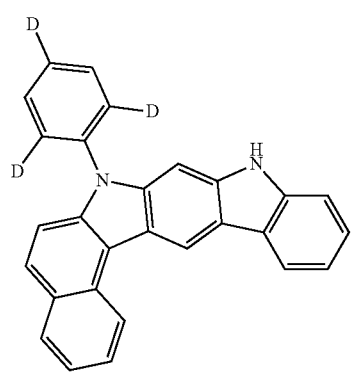
Sub1-31
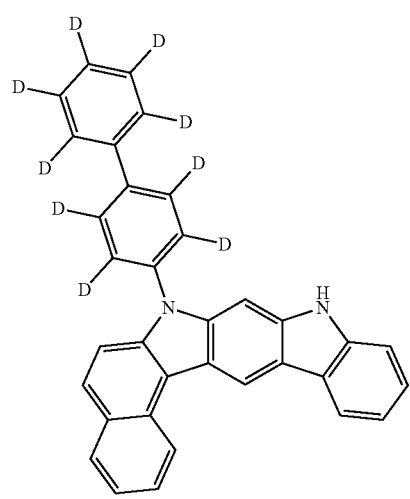
Sub1-32
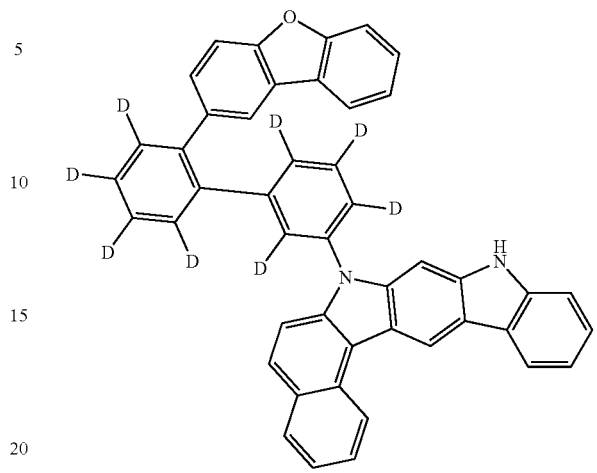
Sub1-33
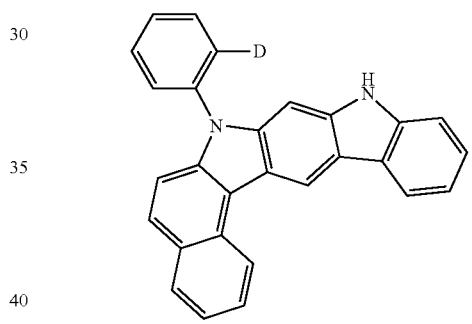
Sub1-34
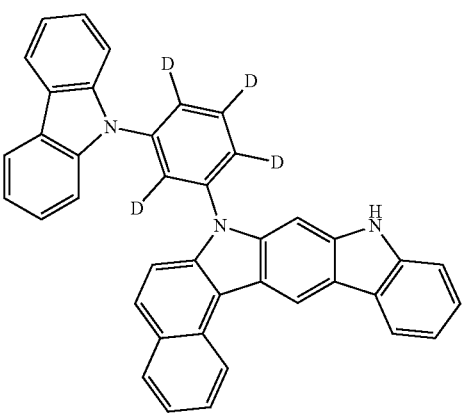

Sub1-35
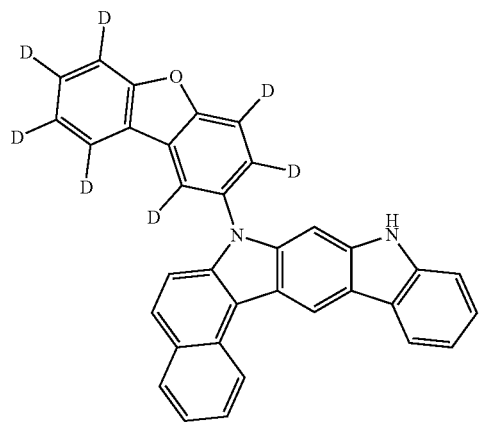
Sub1-38
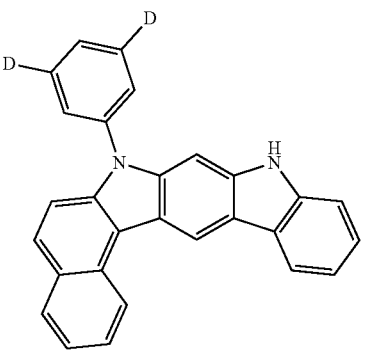
Sub1-36
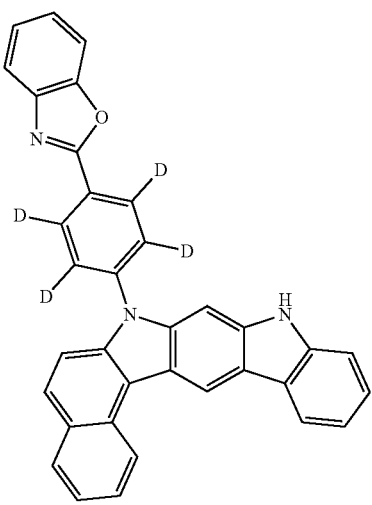
Sub1-39
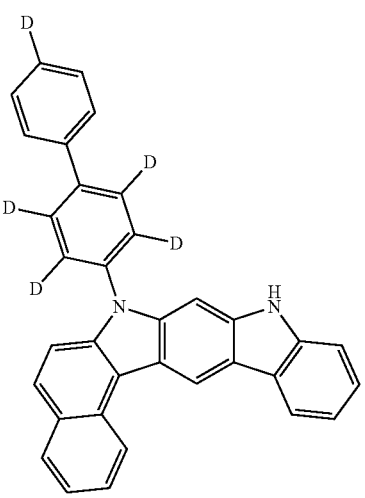
Sub1-37
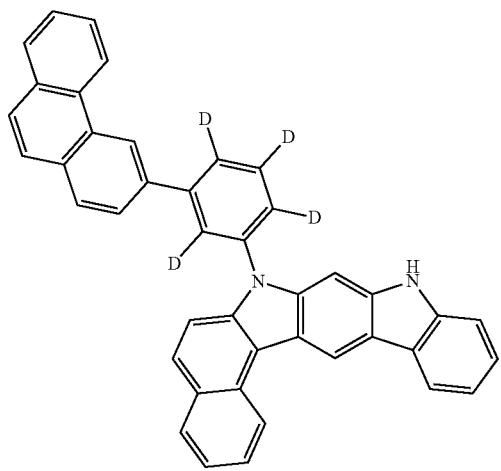
Sub1-40
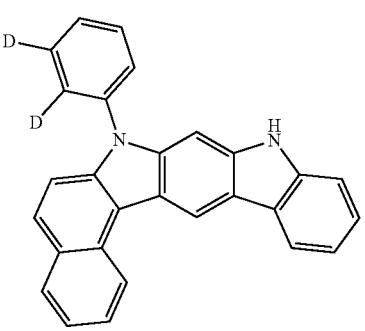

Sub1-41
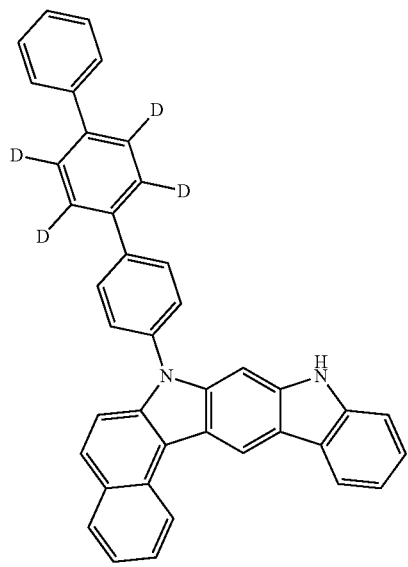
Sub1-42
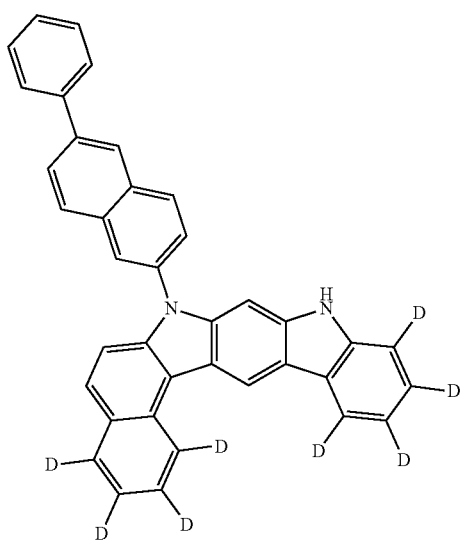
Sub1-43
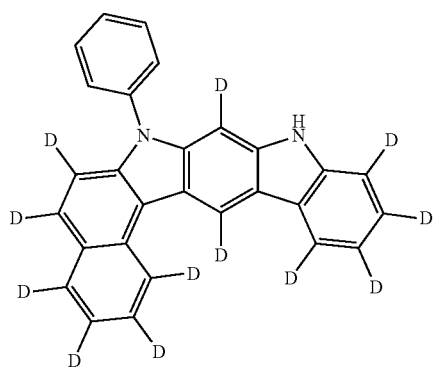
Sub1-44
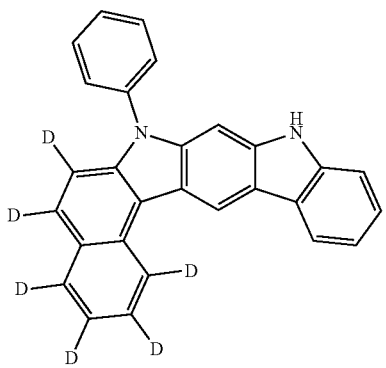
Sub1-45
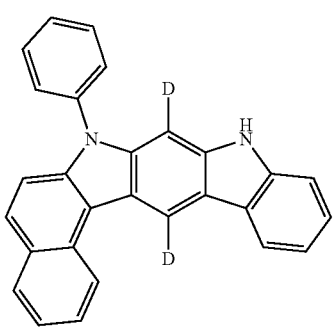
Sub1-46
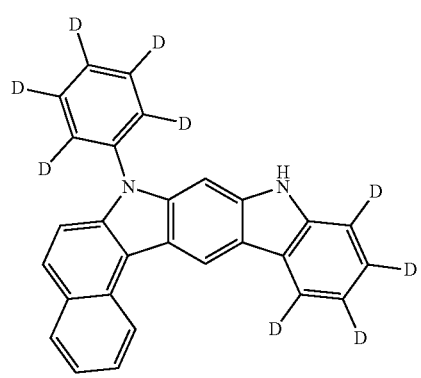

-continued

Sub1-47

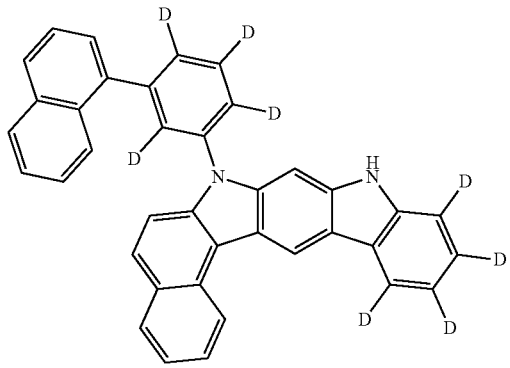

Sub1-48

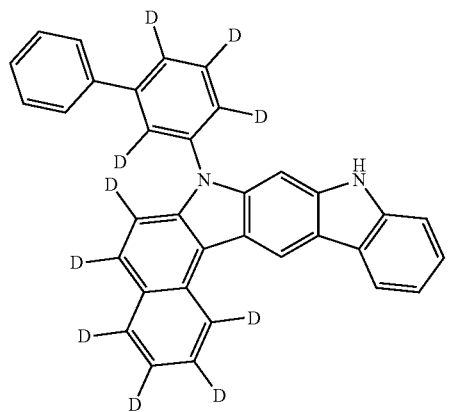

-continued

Sub1-49

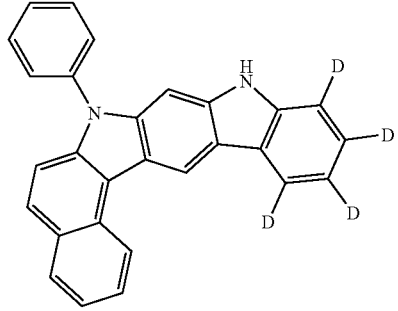

Sub1-50

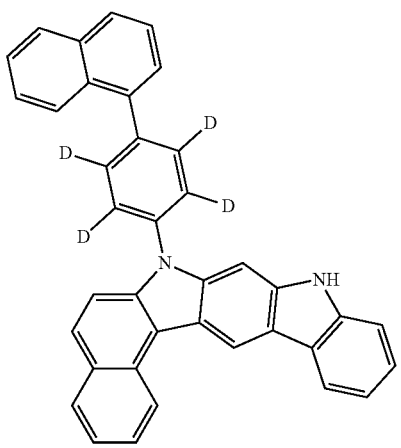

TABLE

| compound | FD-MS | compound | FD-MS |
| --- | --- | --- | --- |
| Sub1-1 | m/z = 382.15($C_{28}H_{18}N_2$ = 382.47) | Sub1-2 | m/z = 432.16($C_{32}H_{20}N_2$ = 432.53) |
| Sub1-3 | m/z = 432.16($C_{32}H_{20}N_2$ = 432.53) | Sub1-4 | m/z = 458.18($C_{34}H_{22}N_2$ = 458.56) |
| Sub1-5 | m/z = 458.18($C_{34}H_{22}N_2$ = 458.56) | Sub1-6 | m/z = 438.21($C_{32}H_{26}N_2$ = 438.57) |
| Sub1-7 | m/z = 508.19($C_{38}H_{24}N_2$ = 508.62) | Sub1-8 | m/z = 482.18($C_{36}H_{22}N_2$ = 482.59) |
| Sub1-9 | m/z = 532.19($C_{40}H_{24}N_2$ = 532.65) | Sub1-10 | m/z = 508.19($C_{38}H_{24}N_2$ = 508.62) |
| Sub1-11 | m/z = 387.18($C_{28}H_{13}D_5N_2$ = 387.5) | Sub1-12 | m/z = 462.2($C_{34}H_{18}D_4N_2$ = 462.59) |
| Sub1-13 | m/z = 462.2($C_{34}H_{18}D_4N_2$ = 462.59) | Sub1-14 | m/z = 491.23($C_{36}H_{13}D_9N_2$ = 491.64) |
| Sub1-15 | m/z = 537.23($C_{40}H_{23}D_3N_2$ = 537.68) | Sub1-16 | m/z = 462.2($C_{34}H_{18}D_4N_2$ = 462.59) |
| Sub1-17 | m/z = 466.23($C_{34}H_{14}D_8N_2$ = 466.61) | Sub1-18 | m/z = 509.2($C_{38}H_{23}DN_2$ = 509.63) |
| Sub1-19 | m/z = 560.22($C_{42}H_{24}D_2N_2$ = 560.7) | Sub1-20 | m/z = 568.19($C_{40}H_{20}D_4N_2S$ = 568.73) |
| Sub1-21 | m/z = 476.18($C_{34}H_{16}D_4N_2O$ = 476.57) | Sub1-22 | m/z = 475.18($C_{34}H_{17}D_3N_2O$ = 475.57) |
| Sub1-23 | m/z = 628.28($C_{47}H_{20}D_8N_2$ = 628.8) | Sub1-24 | m/z = 560.31 ($C_{40}H_{13}D_{14}BN_2$ = 560.57) |
| Sub1-25 | m/z = 551.23($C_{40}H_{21}D_4N_3$ = 551.69) | Sub1-26 | m/z = 489.14($C_{34}H_{19}DN_2S$ = 489.61) |
| Sub1-27 | m/z = 551.23($C_{40}H_{21}D_4N_3$ = 551.69) | Sub1-28 | m/z = 643.26($C_{47}H_{21}D_7N_2O$ = 643.8) |
| Sub1-29 | m/z = 484.19($C_{36}H_{20}D_2N_2$ = 484.6) | Sub1-30 | m/z = 385.17($C_{28}H_{15}D_3N_2$ = 385.48) |
| Sub1-31 | m/z = 467.23($C_{34}H_{13}D_9N_2$ = 467.62) | Sub1-32 | m/z = 632.27($C_{46}H_{20}D_8N_2O$ = 632.79) |
| Sub1-33 | m/z = 383.15($C_{28}H_{17}DN_2$ = 383.47) | Sub1-34 | m/z = 551.23($C_{40}H_{21}D_4N_3$ = 551.69) |
| Sub1-35 | m/z = 479.2($C_{34}H_{13}D_7N_2O$ = 479.59) | Sub1-36 | m/z = 503.19($C_{35}H_{17}D_4N_3O$ = 503.6) |
| Sub1-37 | m/z = 562.23($C_{42}H_{22}D_4N_2$ = 562.71) | Sub1-38 | m/z = 384.16($C_{28}H_{16}D_2N_2$ = 384.48) |
| Sub1-39 | m/z = 463.21 ($C_{34}H_{17}D_5N_2$ = 463.59) | Sub1-40 | m/z = 384.16($C_{28}H_{16}D_2N_2$ = 384.48) |
| Sub1-41 | m/z = 538.23($C_{40}H_{22}D_4N_2$ = 538.69) | Sub1-42 | m/z = 516.24($C_{38}H_{16}D_8N_2$ = 516.67) |
| Sub1-43 | m/z = 394.22($C_{28}H_6D_{12}N_2$ = 394.54) | Sub1-44 | m/z = 388.18($C_{28}H_{12}D_6N_2$ = 388.5) |
| Sub1-45 | m/z = 384.16($C_{28}H_{16}D_2N_2$ = 384.48) | Sub1-46 | m/z = 391.2($C_{28}H_9D_9N_2$ = 391.52) |
| Sub1-47 | m/z = 516.24($C_{38}H_{16}D_8N_2$ = 516.67) | Sub1-48 | m/z = 468.24($C_{34}H_{12}D_{10}N_2$ = 468.63) |
| Sub1-49 | m/z = 386.17($C_{28}H_{14}D_4N_2$ = 386.49) | Sub1-50 | m/z = 512.22($C_{38}H_{20}D_4N_2$ = 512.65) |

Otherwise, the compound belonging to Sub2 may be a compound as follows, but is not limited thereto, and Table 2 below shows FD-MS values of compounds belonging to Sub2-1 to Sub2-63.
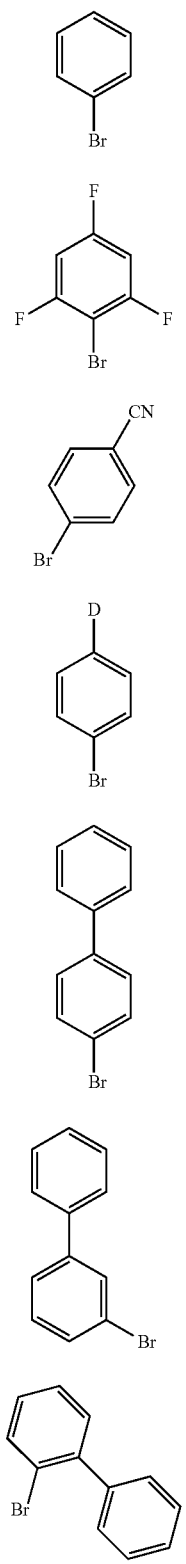
Sub2-1
Sub2-2
Sub2-3
Sub2-4
Sub2-5
Sub2-6
Sub2-7
-continued
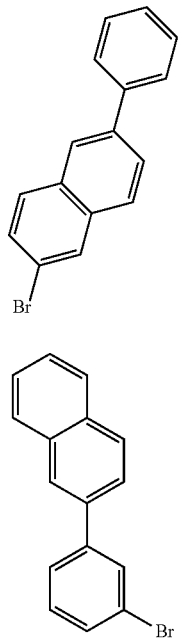
Sub2-8
Sub2-9
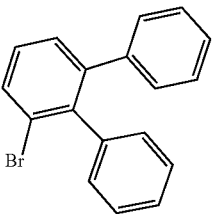
Sub2-10
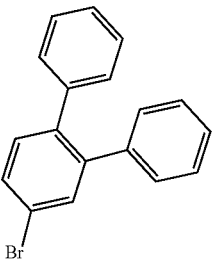
Sub2-11
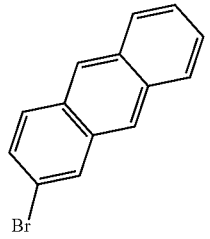
Sub2-12

Sub2-13
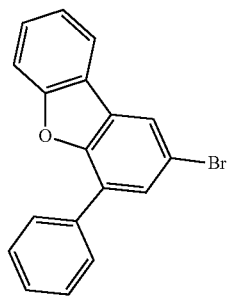
Sub2-14
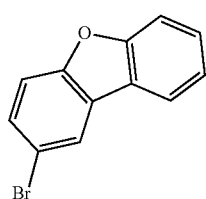
Sub2-15
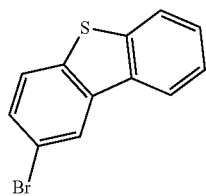
Sub2-16
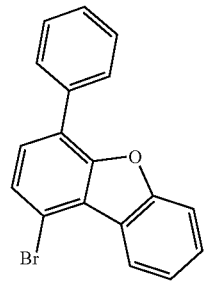
Sub2-17
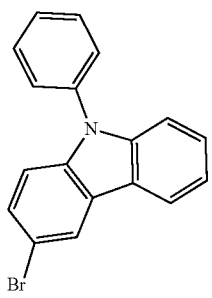
Sub2-18
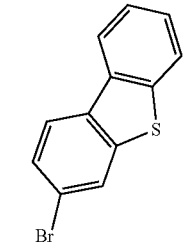
Sub2-19
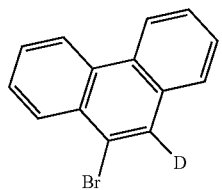
Sub2-20
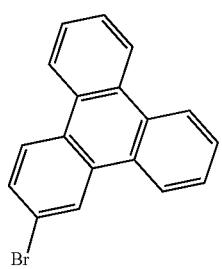
Sub2-21
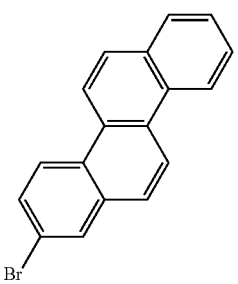
Sub2-22
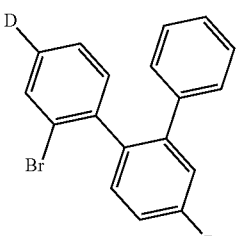
Sub-23
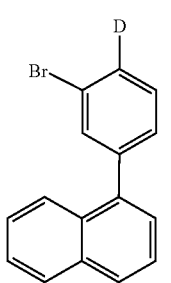

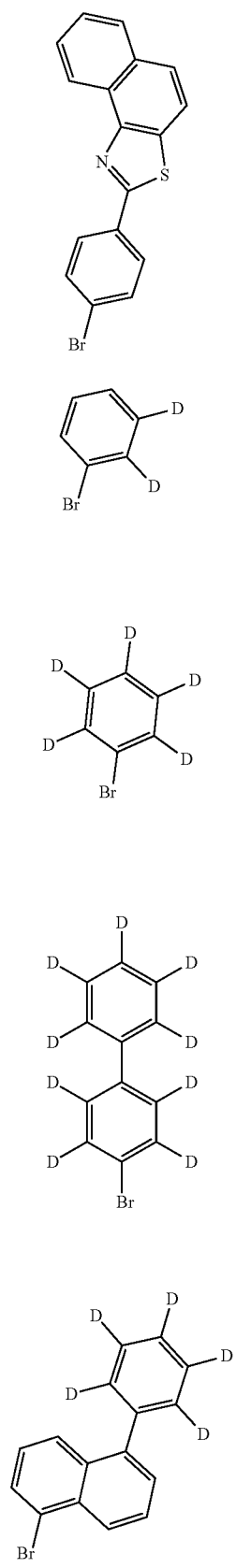

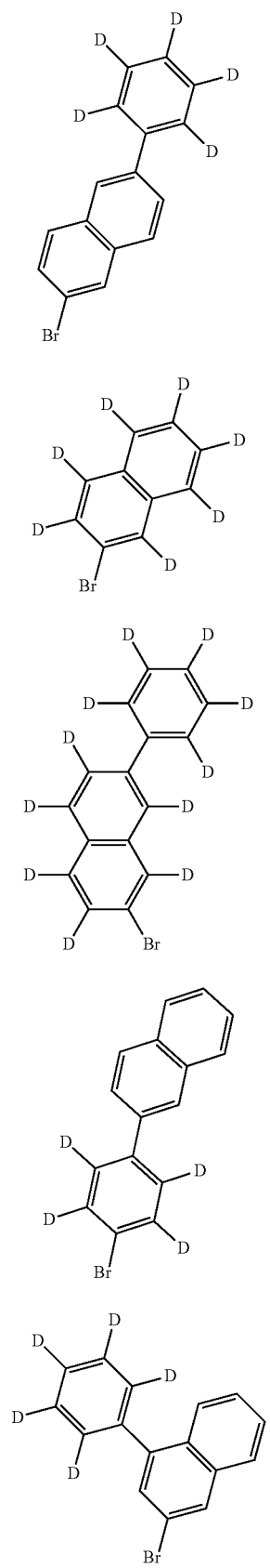
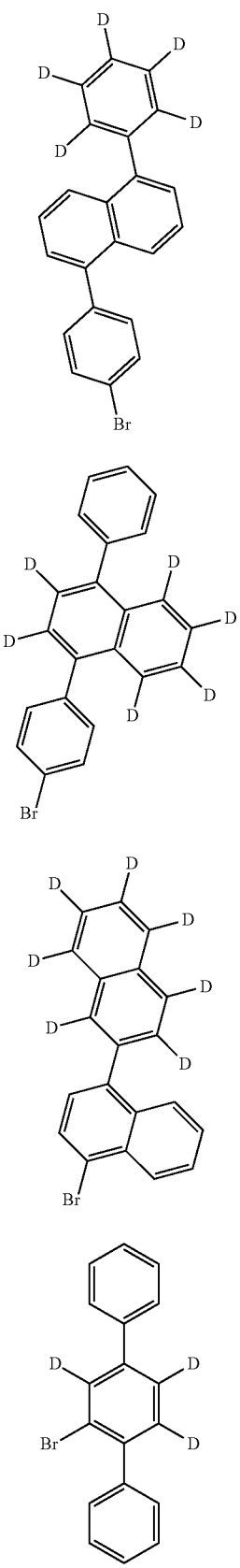

-continued
Sub2-43
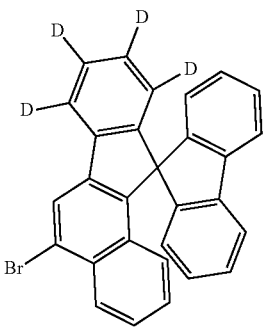
Sub2-44
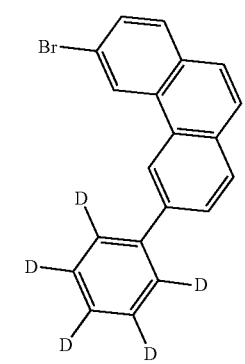
Sub2-45
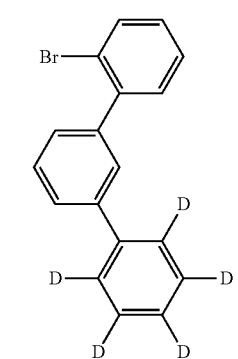
Sub2-46
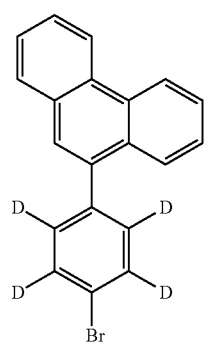
-continued
Sub2-47
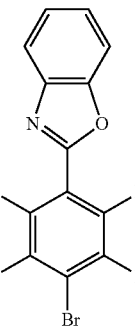
Sub2-48
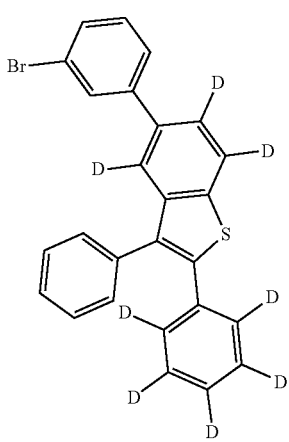
Sub2-49
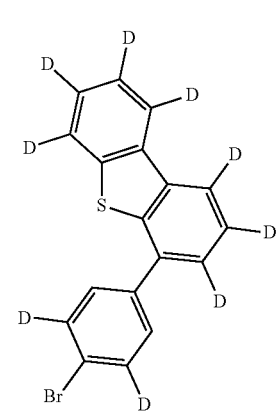
Sub2-50
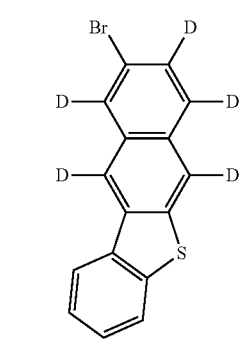

-continued
Sub2-51
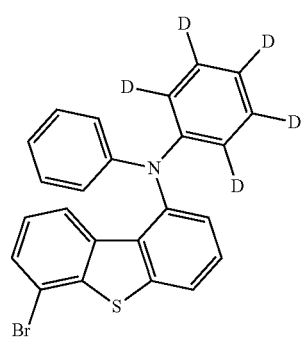
Sub2-52
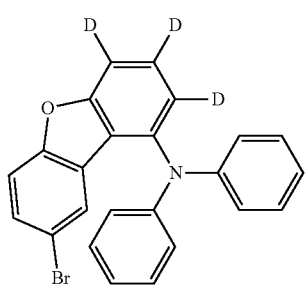
Sub2-53
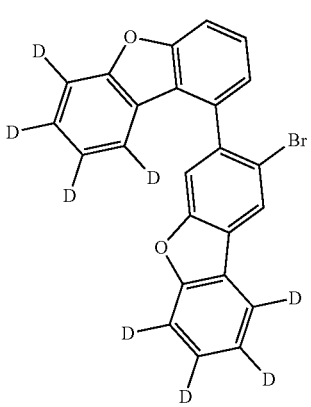
Sub2-54
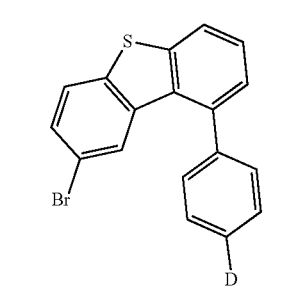
Sub2-55
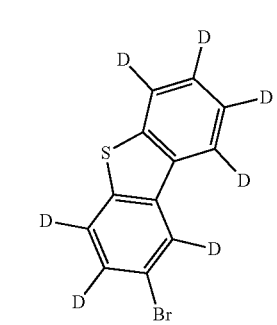
Sub2-56
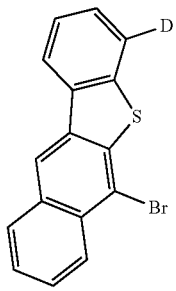
Sub2-57
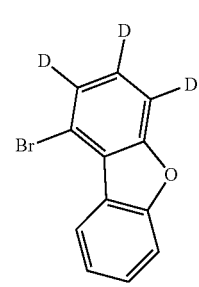
Sub2-58
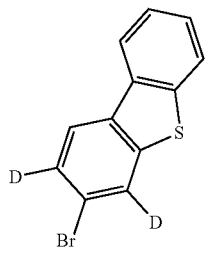
Sub2-59
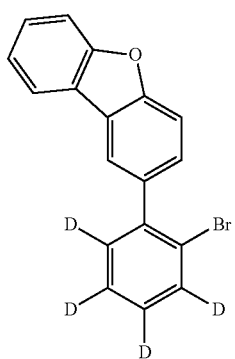

Sub2-60

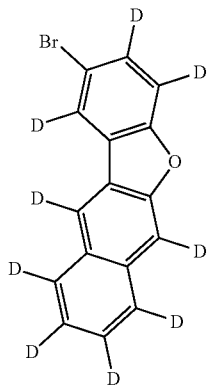

Sub2-61

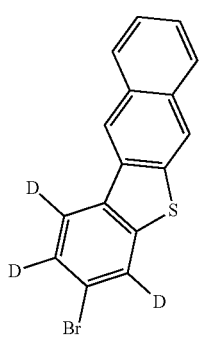

Sub2-62

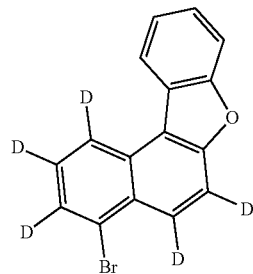

Sub2-63

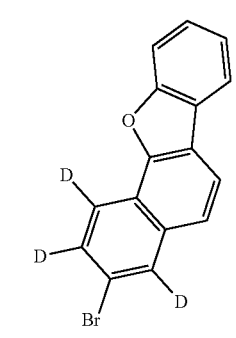

TABLE 2

| compound | FD-MS | compound | FD-MS |
| --- | --- | --- | --- |
| Sub2-1 | m/z = 155.96($C_6H_5Br$ = 157.01) | Sub2-2 | m/z = 209.93($C_6H_2BrF_3$ = 210.98) |
| Sub2-3 | m/z = 180.95($C_7H_4BrN$ = 182.02) | Sub2-4 | m/z = 156.96($C_6H_4DBr$ = 158.02) |
| Sub2-5 | m/z = 231.99($C_{12}H_9Br$ = 233.11) | Sub2-6 | m/z = 231.99($C_{12}H_9Br$ = 233.11) |
| Sub2-7 | m/z = 231.99($C_{12}H_9Br$ = 233.11) | Sub2-8 | m/z = 282($C_{16}H_{11}Br$ = 283.17) |
| Sub2-9 | m/z = 282($C_{16}H_{11}Br$ = 283.17) | Sub2-10 | m/z = 308.02($C_{18}H_{13}Br$ = 309.21) |
| Sub2-11 | m/z = 308.02($C_{18}H_{13}Br$ = 309.21) | Sub2-12 | m/z = 255.99($C_{14}H_9Br$ = 257.13) |
| Sub2-13 | m/z = 322($C_{18}H_{11}BrO$ = 323.19) | Sub2-14 | m/z = 245.97($C_{12}H_7BrO$ = 247.09) |
| Sub2-15 | m/z = 261.95($C_{12}H_7BrS$ = 263.15) | Sub2-16 | m/z = 322($C_{18}H_{11}BrO$ = 323.19) |
| Sub2-17 | m/z = 321.02($C_{18}H_{12}BrN$ = 322.21) | Sub2-18 | m/z = 261.95($C_{12}H_7BrS$ = 263.15) |
| Sub2-19 | m/z = 257($C_{14}H_8DBr$ = 258.14) | Sub2-20 | m/z = 306($C_{18}H_{11}Br$ = 307.19) |
| Sub2-21 | m/z = 306($C_{18}H_{11}Br$ = 307.19) | Sub2-22 | m/z = 310.03($C_{18}H_{11}D_2Br$ = 311.22) |
| Sub2-23 | m/z = 283.01($C_{16}H_{10}DBr$ = 284.17) | Sub2-24 | m/z = 338.97($C_{17}H_{10}BrNS$ = 340.24) |
| Sub2-25 | m/z = 157.97($C_6H_3D_2Br$ = 159.02) | Sub2-26 | m/z = 160.99($C_6D_5Br$ = 162.04) |
| Sub2-27 | m/z = 241.05($C_{12}D_9Br$ = 242.16) | Sub2-28 | m/z = 287.04($C_{16}H_6D_5Br$ = 288.2) |
| Sub2-29 | m/z = 363.07($C_{22}H_{10}D_5Br$ = 364.3) | Sub2-30 | m/z = 237.02($C_{12}H_4D_5Br$ = 238.14) |
| Sub2-31 | m/z = 236.01($C_{12}H_5D_4Br$ = 237.13) | Sub2-32 | m/z = 286.03($C_{16}H_7D_4Br$ = 287.19) |
| Sub2-33 | m/z = 237.02($C_{12}H_4D_5Br$ = 238.14) | Sub2-34 | m/z = 287.04($C_{16}H_6D_5Br$ = 288.2) |
| Sub2-35 | m/z = 213.02($C_{10}D_7Br$ = 214.11) | Sub2-36 | m/z = 293.07($C_{16}D_{11}Br$ = 294.24) |
| Sub2-37 | m/z = 286.03($C_{16}H_7D_4Br$ = 287.19) | Sub2-38 | m/z = 287.04($C_{16}H_6D_5Br$ = 288.2) |
| Sub2-39 | m/z = 363.07($C_{22}H_{10}D_5Br$ = 364.3) | Sub2-40 | m/z = 364.07($C_{22}H_9D_6Br$ = 365.3) |
| Sub2-41 | m/z = 339.06($C_{20}H_6D_7Br$ = 340.27) | Sub2-42 | m/z = 311.04($C_{18}H_{10}D_3Br$ = 312.22) |
| Sub2-43 | m/z = 448.08($C_{29}H_{13}D_4Br$ = 449.38) | Sub2-44 | m/z = 337.05($C_{20}H_8D_5Br$ = 338.26) |
| Sub2-45 | m/z = 313.05($C_{18}H_8D_5Br$ = 314.24) | Sub2-46 | m/z = 336.05($C_{20}H_9D_4Br$ = 337.25) |
| Sub2-47 | m/z = 277($C_{13}H_4D_4BrNO$ = 278.14) | Sub2-48 | m/z = 448.07($C_{26}H_9D_8BrS$ = 449.43) |
| Sub2-49 | m/z = 347.03($C_{18}H_2D_9BrS$ = 348.3) | Sub2-50 | m/z = 316.99($C_{16}H_4D_5BrS$ = 318.24) |
| Sub2-51 | m/z = 434.05($C_{24}H_{11}D_5BrNS$ = 435.39) | Sub2-52 | m/z = 416.06($C_{24}H_{13}D_3BrNO$ = 417.32) |
| Sub2-53 | m/z = 420.06($C_{24}H_5D_8BrO_2$ = 421.32) | Sub2-54 | m/z = 338.98($C_{18}H_{10}DBrS$ = 340.26) |
| Sub2-55 | m/z = 268.99($C_{12}D_7BrS$ = 270.19) | Sub2-56 | m/z = 312.97($C_{16}H_8DBrS$ = 314.22) |
| Sub2-57 | m/z = 248.99($C_{12}H_4D_3BrO$ = 250.11) | Sub2-58 | m/z = 263.96($C_{12}H_5D_2BrS$ = 265.16) |
| Sub2-59 | m/z = 326.02($C_{18}H_7D_4BrO$ = 327.21) | Sub2-60 | m/z = 305.04($C_{16}D_9BrO$ = 306.21) |
| Sub2-61 | m/z = 314.98($C_{16}H_6D_3BrS$ = 316.23) | Sub2-62 | m/z = 301.02($C_{16}H_4D_5BrO$ = 302.18) |
| Sub2-63 | m/z = 299($C_{16}H_6D_3BrO$ = 300.17) | | |

II. Synthesis of Final Product

1. Synthesis Example of P-2

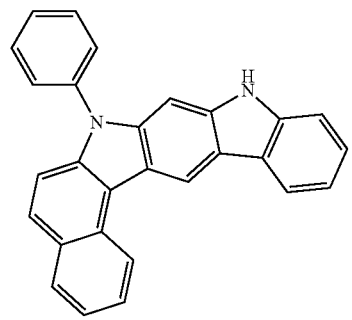

Sub1-1

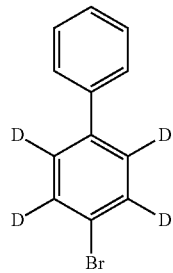

Sub2-31

$$\xrightarrow[\text{Toluene}]{\text{Pd}_2(\text{dba})_3/\text{P(t-Bu)}_3 \text{ NaOt-Bu}}$$

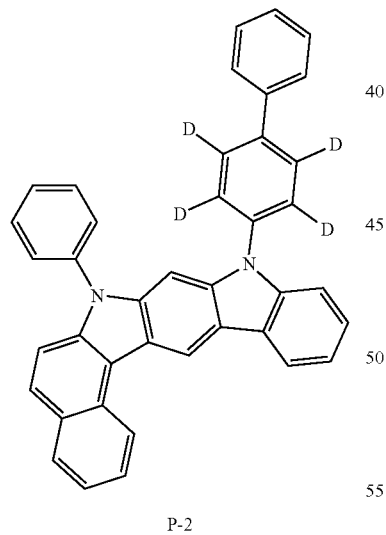

P-2

Sub1-1 (40 g, 0.10 mol), Sub2-31 (24.8 g, 0.10 mol), Pd$_2$(dba)$_3$ (2.9 g, 0.003 mol), NaOt-Bu (30.2 g, 0.31 mol), P(t-Bu)$_3$ (2.5 g, 0.006 mol), Toluene (210 mL) were added and reacted at 135° C. for 6 hours. When the reaction is completed, the temperature of the reactant is cooled to room temperature, and the reaction solvent is removed. Then, the concentrated reactant was separated using a silica gel column or recrystallization method to obtain 48 g (85.2%) of product P-2.

2. Synthesis Example of P-7

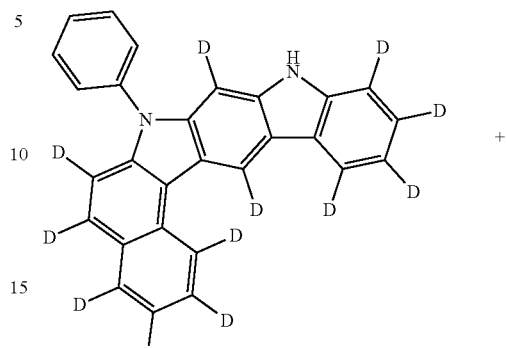

Sub1-43

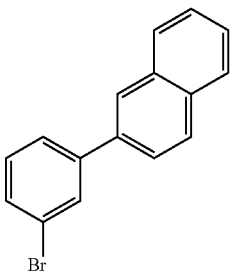

Sub2-9

$$\xrightarrow[\text{Toluene}]{\text{Pd}_2(\text{dba})_3/\text{P(t-Bu)}_3 \text{ NaOt-Bu}}$$

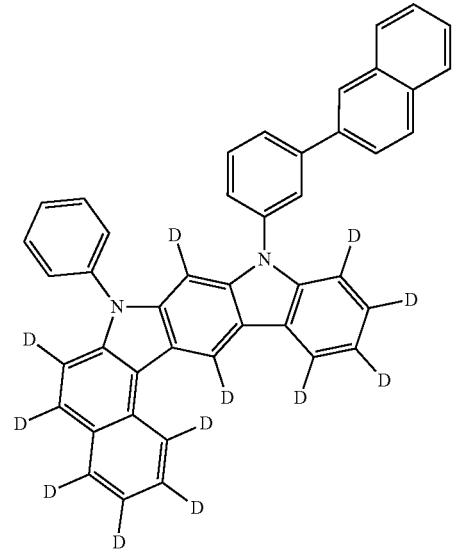

P-7

Sub1-43 (20 g, 0.05 mol), Sub2-9 (14.4 g, 0.05 mol), Pd$_2$(dba)$_3$ (1.4 g, 0.0015 mol), NaOt-Bu (14.6 g, 0.15 mol), P(t-Bu)$_3$ (1.2 g, 0.003 mol), Toluene (100 mL) were added and reacted at 135° C. for 6 hours. When the reaction is completed, 27 g (89.2%) of the product P-7 was obtained by using the separation method for P-2 described above.

3. Synthesis Example of P-17

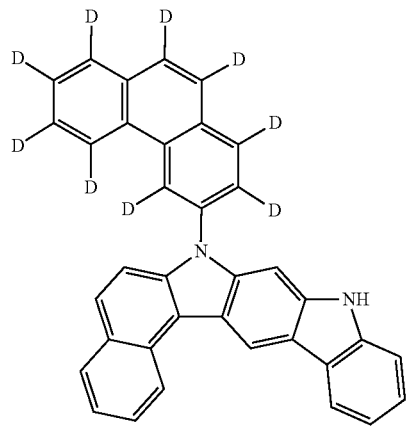

Sub1-14

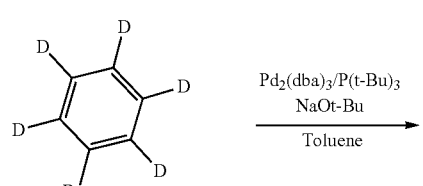

Sub2-26

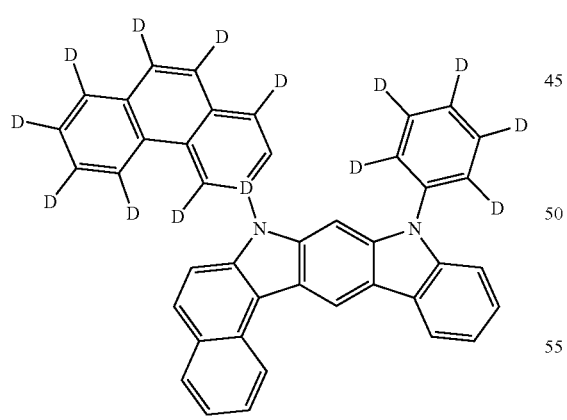

P-17

Sub1-14 (38 g, 0.08 mol), Sub2-26 (12.5 g, 0.08 mol), Pd₂(dba)₃ (2.1 g, 0.002 mol), NaOt-Bu (22.3 g, 0.23 mol), P(t-Bu)₃ (1.9 g, 0.0046 mol), Toluene (155 mL) were added and reacted at 135° C. for 6 hours. When the reaction was completed, 40 g (90.5%) of the product P-17 was obtained by using the separation method for P-2 described above.

4. Synthesis Example of P-28

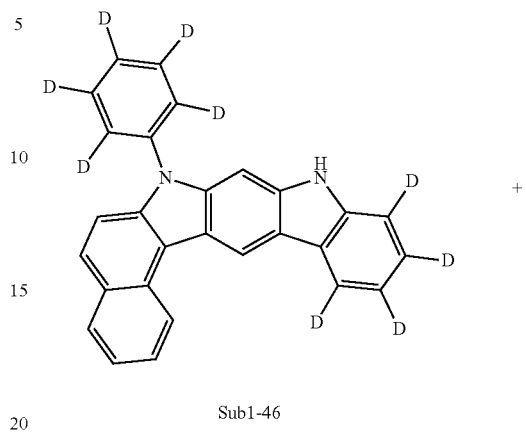

Sub1-46

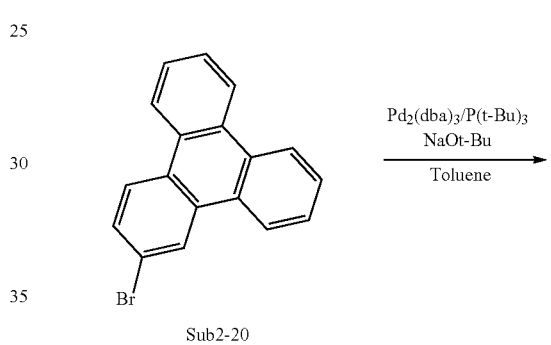

Sub2-20

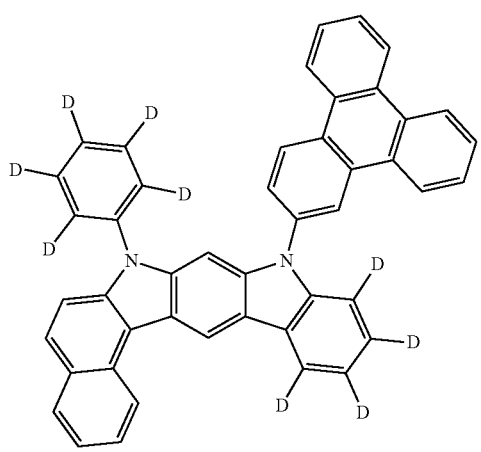

P-28

Sub1-46 (30 g, 0.08 mol), Sub2-20 (23.6 g, 0.08 mol), Pd₂(dba)₃ (2.1 g, 0.002 mol), NaOt-Bu (22.1 g, 0.23 mol), P(t-Bu)₃ (1.9 g, 0.0046 mol), Toluene (155 mL) were added and reacted at 135° C. for 6 hours. When the reaction was completed, 41 g (86.6%) of the product P-28 was obtained by using the separation method for P-2 described above.

5. Synthesis Example of P-37

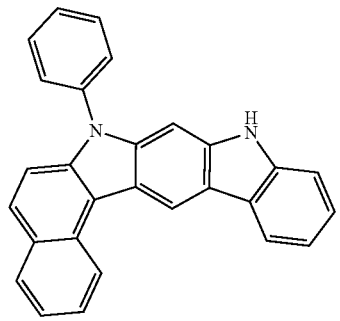
Sub1-1

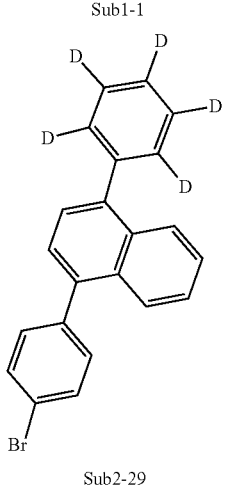
Sub2-29

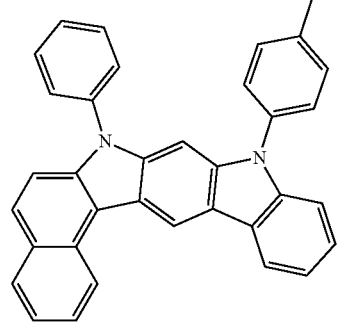
P-37

Sub1-1 (47 g, 0.12 mol), Sub2-29 (44.8 g, 0.12 mol), Pd₂(dba)₃ (3.4 g, 0.004 mol), NaOt-Bu (35.5 g, 0.37 mol), P(t-Bu)₃ (3 g, 0.007 mol), Toluene (250 mL) were added and reacted at 135° C. for 6 hours. When the reaction was completed, 69 g (84.3%) of the product P-37 was obtained by using the separation method for P-2 described above.

6. Synthesis Example of P-46

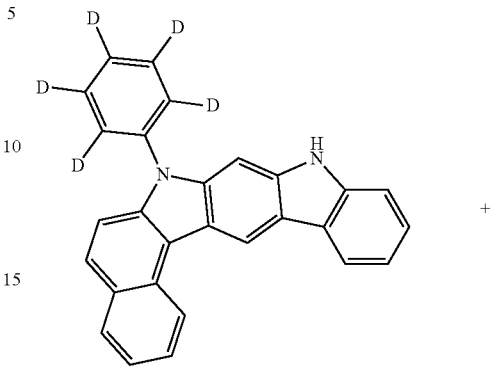
Sub1-11

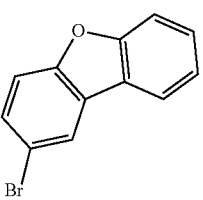
Sub2-14

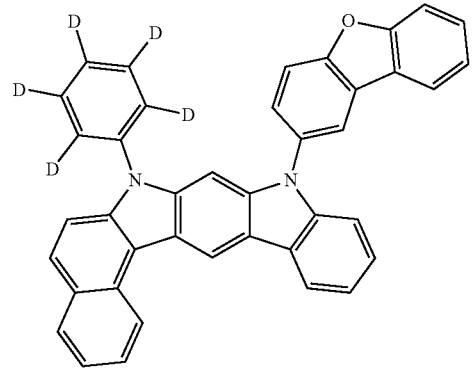
P-46

Sub1-11 (18 g, 0.05 mol), Sub2-14 (11.5 g, 0.05 mol), Pd₂(dba)₃ (1.3 g, 0.0014 mol), NaOt-Bu (13.4 g, 0.14 mol), P(t-Bu)₃ (1.1 g, 0.003 mol), Toluene (90 mL) were added and reacted at 135° C. for 6 hours. When the reaction was completed, 22 g (85.5%) of the product P-46 was obtained by using the separation method for P-2 described above.

7. Synthesis Example of P-53

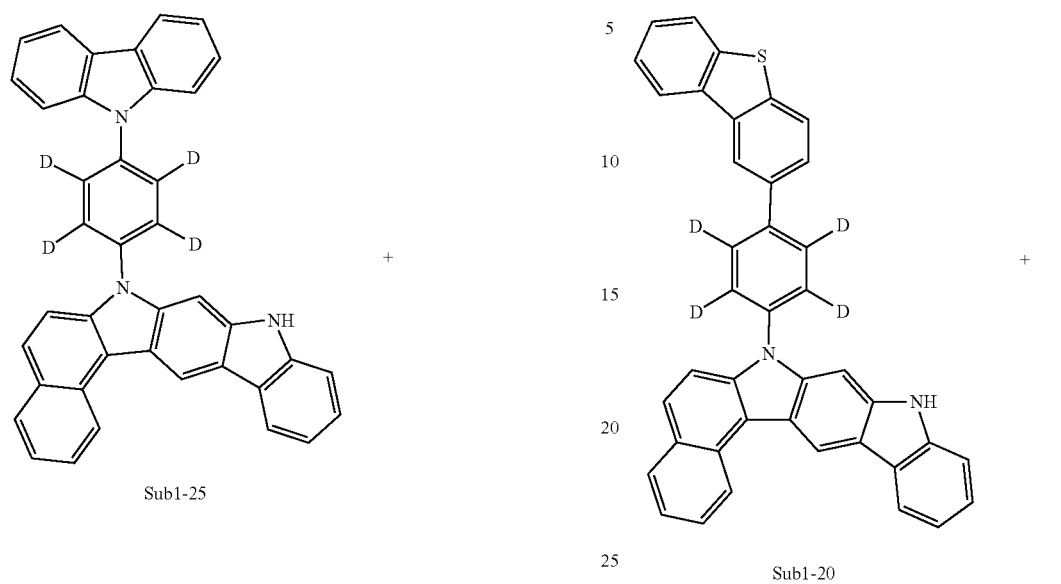

8. Synthesis Example of P-61

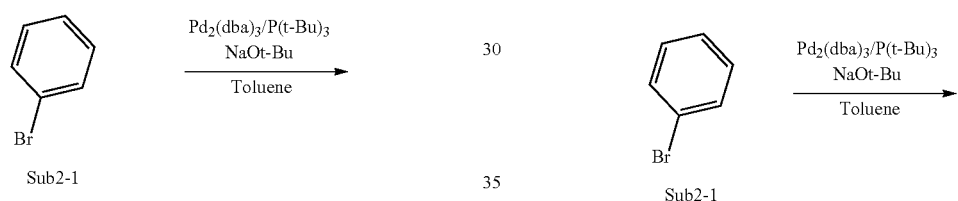

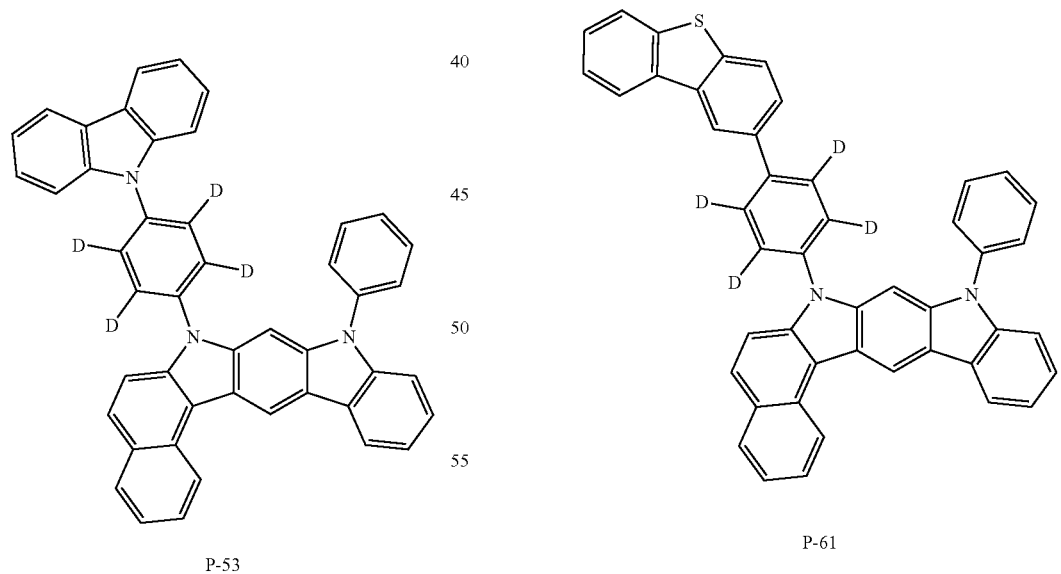

Sub1-25 (38 g, 0.07 mol), Sub2-1 (10.8 g, 0.07 mol), Pd$_2$(dba)$_3$ (1.9 g, 0.0021 mol), NaOt-Bu (19.9 g, 0.21 mol), P(t-Bu)$_3$ (1.7 g, 0.004 mol), Toluene (140 mL) were added, and the reaction was conducted at 135° C. for 6 hours. When the reaction was completed, 35 g (80.9%) of the product P-53 was obtained by using the separation method for P-2 described above.

Sub1-20 (40 g, 0.07 mol), Sub2-1 (11.1 g, 0.07 mol), Pd$_2$(dba)$_3$ (1.9 g, 0.0021 mol), NaOt-Bu (20.3 g, 0.21 mol), P(t-Bu)$_3$ (1.7 g, 0.0042 mol), Toluene (140 mL) were added, and the reaction was conducted at 135° C. for 6 hours. When the reaction was completed, 40 g (88.2%) of the product P-61 was obtained by using the separation method for P-2 described above.

9. Synthesis Example of P-71

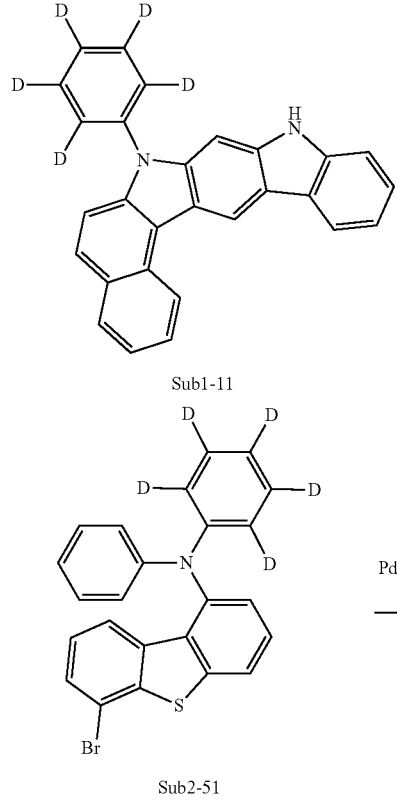

Sub1-11

Sub2-51

Pd$_2$(dba)$_3$/P(t-Bu)$_3$
NaOt-Bu
Toluene
⟶

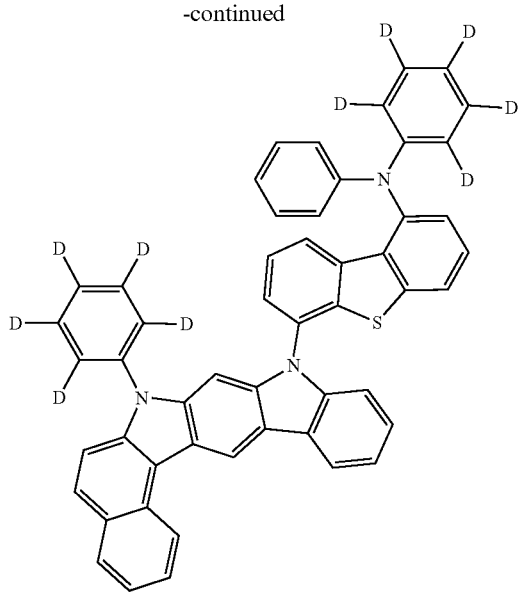

P-71

Sub1-11 (40 g, 0.10 mol), Sub2-51 (45 g, 0.10 mol), Pd$_2$(dba)$_3$ (2.8 g, 0.0031 mol), NaOt-Bu (29.8 g, 0.31 mol), P(t-Bu)$_3$ (2.5 g, 0.006 mol), Toluene (210 mL) were added, and the reaction was conducted at 135° C. for 6 hours. When the reaction was completed, 62 g (81%) of the product P-71 was obtained by using the separation method for P-2 described above.

Meanwhile, FD-MS values of compounds P-1 to P-90 of the present invention prepared according to the above synthesis examples are shown in Table 3 below.

TABLE 3

| compound | FD-MS | compound | FD-MS |
|---|---|---|---|
| P-1 | m/z = 463.21(C$_{34}$H$_{17}$D$_5$N$_2$ = 463.59) | P-2 | m/z = 538.23(C$_{40}$H$_{22}$D$_4$N$_2$ = 538.69) |
| P-3 | m/z = 539.24(C$_{40}$H$_{21}$D$_5$N$_2$ = 539.69) | P-4 | m/z = 539.24(C$_{40}$H$_{21}$D$_5$N$_2$ = 539.69) |
| P-5 | m/z = 585.23(C$_{44}$H$_{27}$D$_{N2}$ = 585.73) | P-6 | m/z = 588.25(C$_{44}$H$_{24}$D$_4$N$_2$ = 588.75) |
| P-7 | m/z = 596.3(C$_{44}$H$_{16}$D$_{12}$N$_2$ = 596.8) | P-8 | m/z = 619.3(C$_{46}$H$_{21}$D$_9$N$_2$ = 619.81) |
| P-9 | m/z = 614.27(C$_{46}$H$_{26}$D$_4$N$_2$ = 614.78) | P-10 | m/z = 619.3(C$_{46}$H$_{21}$D$_9$N$_2$ = 619.81) |
| P-11 | m/z = 614.27(C$_{46}$H$_{26}$D$_4$N$_2$ = 614.78) | P-12 | m/z = 593.28(C$_{44}$H$_{19}$D$_9$N$_2$ = 593.78) |
| P-13 | m/z = 639.27(C$_{48}$H$_{25}$D$_5$N$_2$ = 639.81) | P-14 | m/z = 614.27(C$_{46}$H$_{26}$D$_4$N$_2$ = 614.78) |
| P-15 | m/z = 615.27(C$_{46}$H$_{25}$D$_5$N$_2$ = 615.79) | P-16 | m/z = 565.25(C$_{42}$H$_{19}$D$_7$N$_2$ = 565.73) |
| P-17 | m/z = 572.3(C$_{42}$H$_{12}$D$_{14}$N$_2$ = 572.77) | P-18 | m/z = 563.24(C$_{42}$H$_{21}$D$_5$N$_2$ = 563.71) |
| P-19 | m/z = 689.29(C$_{52}$H$_{31}$D$_3$N$_2$ = 689.88) | P-20 | m/z = 595.29(C$_{44}$H$_{17}$D$_{11}$N$_2$ = 595.79) |
| P-21 | m/z = 689.29(C$_{52}$H$_{31}$D$_3$N$_2$ = 689.88) | P-22 | m/z = 622.32(C$_{46}$H$_{18}$D$_{12}$N$_2$ = 622.83) |
| P-23 | m/z = 641.28(C$_{48}$H$_{23}$D$_7$N$_2$ = 641.82) | P-24 | m/z = 559.22(C$_{42}$H$_{25}$DN$_2$ = 559.69) |
| P-25 | m/z = 614.27(C$_{46}$H$_{26}$D$_4$N$_2$ = 614.78) | P-26 | m/z = 620.3(C$_{46}$H$_{20}$D$_{10}$N$_2$ = 620.82) |
| P-27 | m/z = 715.3(C$_{54}$H$_{29}$D$_5$N$_2$ = 715.91) | P-28 | m/z = 617.28(C$_{46}$H$_{19}$D$_9$N$_2$ = 617.8) |
| P-29 | m/z = 519.27(C$_{38}$H$_{25}$D$_5$N$_2$ = 519.7) | P-30 | m/z = 694.32(C$_{52}$H$_{26}$D$_8$N$_2$ = 694.91) |
| P-31 | m/z = 585.23(C$_{44}$H$_{27}$DN$_2$ = 585.73) | P-32 | m/z = 637.26(C$_{48}$H$_{27}$D$_3$N$_2$ = 637.8) |
| P-33 | m/z = 620.3(C$_{46}$H$_{20}$D$_{10}$N$_2$ = 620.82) | P-34 | m/z = 638.27(C$_{48}$H$_{26}$D$_4$N$_2$ = 638.81) |
| P-35 | m/z = 639.27(C$_{48H25}$D$_5$N$_2$ = 639.81) | P-36 | m/z = 614.27(C$_{46}$H$_{26}$D$_4$N$_2$ = 614.78) |
| P-37 | m/z = 665.29(C$_{50}$H$_{27}$D$_5$N$_2$ = 665.85) | P-38 | m/z = 665.29(C$_{50}$H$_{27}$D$_5$N$_2$ = 665.85) |
| P-39 | m/z = 589.26(C$_{44}$H$_{23}$D$_5$N$_2$ = 589.75) | P-40 | m/z = 639.27(C$_{48}$H$_{25}$D$_5$N$_2$ = 639.81) |
| P-41 | m/z = 638.27(C$_{48}$H$_{26}$D$_4$N$_2$ = 638.81) | P-42 | m/z = 613.26(C$_{46}$H$_{23}$D$_5$N$_2$ = 613.77) |
| P-43 | m/z = 665.29(C$_{50}$H$_{27}$D$_5$N$_2$ = 665.85) | P-44 | m/z = 666.29(C$_{50}$H$_{26}$D$_6$N$_2$ = 666.86) |
| P-45 | m/z = 552.21 (C$_{40}$H$_{20}$D$_4$N$_2$O = 552.67) | P-46 | m/z = 553.22(C$_{40}$H$_{19}$D$_5$N$_2$O = 553.68) |
| P-47 | m/z = 617.2(C$_{44}$H$_{23}$D$_3$N$_2$S = 617.78) | P-48 | m/z = 608.27(C$_{44}$H$_{16}$D$_{10}$N$_2$O = 608.77) |
| P-49 | m/z = 644.24 (C$_{46}$H$_{20}$D$_6$N$_2$O$_2$ = 644.76) | P-50 | m/z = 642.21(C$_{46}$H$_{26}$D$_2$N$_2$S = 642.82) |
| P-51 | m/z = 628.27(C$_{46}$H$_{24}$D$_5$N$_3$ = 628.79) | P-52 | m/z = 607.26(C$_{44}$H$_{17}$D$_9$N$_2$O = 607.76) |
| P-53 | m/z = 627.26(C$_{46}$H$_{25}$D$_4$N$_3$ = 627.78) | P-54 | m/z = 565.17(C$_{40}$H$_{23}$DN$_2$S = 565.71) |
| P-55 | m/z = 627.26(C$_{46}$H$_{25}$D$_4$N$_3$ = 627.78) | P-56 | m/z = 633.28(C$_{46}$H$_{19}$D$_9$N$_2$O = 633.8) |
| P-57 | m/z = 641.2(C$_{46}$H$_{27}$DN$_2$S = 641.81) | P-58 | m/z = 576.24(C$_{40}$H$_{12}$D$_{12}$N$_2$S = 576.78) |
| P-59 | m/z = 601.22(C$_{44}$H$_{23}$D$_3$N$_2$O = 601.72) | P-60 | m/z = 750.3(C$_{57}$H$_{30}$D$_{4N2}$ = 750.94) |
| P-61 | m/z = 644.22(C$_{46}$H$_{24}$D$_4$N$_2$S = 644.83) | P-62 | m/z = 630.26(C$_{46}$H$_{22}$D$_6$N$_2$O = 630.78) |
| P-63 | m/z = 550.2(C$_{40}$H$_{22}$D$_2$N$_2$O = 550.66) | P-64 | m/z = 649.25(C$_{46}$H$_{19}$D$_9$N$_2$S = 649.86) |
| P-65 | m/z = 704.31(C$_{53}$H$_{24}$D$_8$N$_2$ = 704.9) | P-66 | m/z = 719.3(C$_{53}$H$_{25}$D$_7$N$_2$O = 719.89) |

TABLE 3-continued

| compound | FD-MS | compound | FD-MS |
|---|---|---|---|
| P-67 | m/z = 636.35($C_{46}H_{17}D_{14}BN_2$ = 636.66) | P-68 | m/z = 619.21 ($C_{44}H_{21}D_5N_2S$ = 619.8) |
| P-69 | m/z = 666.21($C_{48}H_{26}D_2N_2S$ = 666.84) | P-70 | m/z = 628.25($C_{46}H_{24}D_4N_2O$ = 628.77) |
| P-71 | m/z = 741.3($C_{52}H_{23}D_{10}N_3S$ = 741.98) | P-72 | m/z = 719.29($C_{52}H_{29}D_4N_3O$ = 719.88) |
| P-73 | m/z = 708.3($C_{52}H_{24}D_8N_2O$ = 708.89) | P-74 | m/z = 515.17($C_{34}H_{16}D_3F_3N_2$ = 51 5.55) |
| P-75 | m/z = 649.25($C_{46}H_{19}D_9N_2S$ = 649.86) | P-76 | m/z = 722.28($C_{52}H_{22}D_8N_2O_2$ = 722.87) |
| P-77 | m/z = 627.26($C_{46}H_{25}D_4N_3$ = 627.78) | P-78 | m/z = 555.23($C_{40}H_{17}D_7N_2O$ = 555.69) |
| P-79 | m/z = 700.27($C_{48}H_{20}D_8N_4O_2$ = 700.83) | P-80 | m/z = 750.29($C_{54}H_{26}D_8N_2S$ = 750.99) |
| P-81 | m/z = 488.2($C_{35}H_{16}D_5N_3$ = 488.6) | P-82 | m/z = 615.19($C_{44}H_{25}DN_2S$ = 615.77) |
| P-83 | m/z = 588.25($C_{44}H_{24}D_4N_2$ = 588.75) | P-84 | m/z = 562.23($C_{42}H_{22}D_4N_2$ = 562.71) |
| P-85 | m/z = 592.28($C_{44}H_{20}D_8N_2$ = 592.77) | P-86 | m/z = 718.32($C_{54}H_{26}D_8N_2$ = 71 8.93) |
| P-87 | m/z = 722.26($C_{51}H_{26}D_5N_3S$ = 722.92) | P-88 | m/z = 462.2($C_{34}H_{18}D_4N_2$ = 462.59) |
| P-89 | m/z = 588.25($C_{44}H_{24}D_4N_2$ = 588.75) | P-90 | m/z = 620.3($C_{46}H_{20}D_{10}N_2$ = 620.82) |

[Example 1] Red Organic Light Emitting Device (Phosphorescent Host)

An organic electroluminescent device was manufactured according to a conventional method by using the compound obtained through synthesis as a light emitting host material of the emitting layer. First, on the ITO layer (anode) formed on a glass substrate, after vacuum deposition of N1-(naphthalen-2-yl)-N4, N4-bis(4-(naphthalen-2-yl(phenyl)amino) phenyl)-N1-phenylbenzene-1,4-diamine (abbreviated as 2-TNATA) to form a hole injection layer with a thickness of 60 nm, on the hole injection layer, 4,4-bis[N-(1-naphthyl)-N-phenylamino]biphenyl (abbreviated as -NPD) as a hole transport compound was vacuum-deposited to a thickness of 60 nm to form a hole transport layer. As a host on the hole transport layer, the compound (P-2) of the present invention represented by Formula (1) and the compound DSNL1 below were used in a weight ratio (5:5), and (piq)$_2$Ir(acac) [bis-(1-phenylisoquinolyl)iridium(III)acetylacetonate] as a dopant material was doped at a weight ratio of 95:5 to deposit an emitting layer with a thickness of 30 nm. Subsequently, (1,1'-bisphenyl)-4-oleato)bis(2-methyl-8-quinolineoleato)aluminum (hereinafter abbreviated as BAlq) as a hole-blocking layer was vacuum-deposited to a thickness of 10 nm, and as an electron transport layer, tris(8-quinolinol) aluminum (hereinafter, abbreviated as Alq$_3$) was deposited to a thickness of 40 nm. Thereafter, LiF, which is an alkali metal halide, was deposited as an electron injection layer to a thickness of 0.2 nm, and then Al was deposited to a thickness of 150 nm to be used as a cathode, thereby manufacturing an organic electroluminescent device.

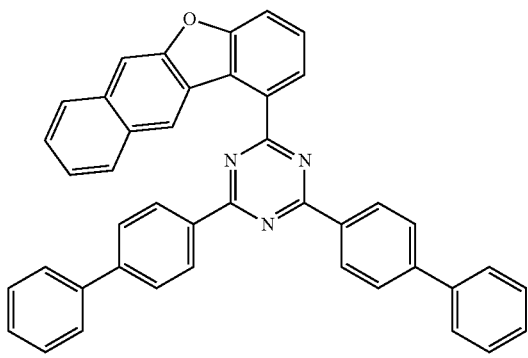

<DSNL1>

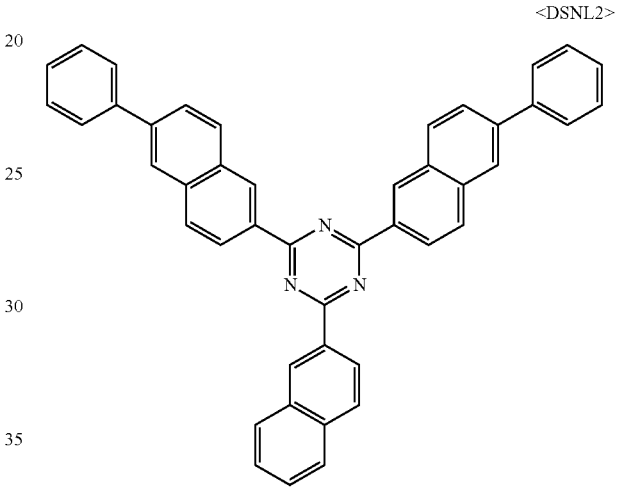

<DSNL2>

[Example 2] to [Example 28]

An organic electroluminescent device was manufactured in the same manner as in Example 1, except that the compound of the present invention described in Table 4 was used instead of the compound (P-2) of the present invention as the host material of the emitting layer.

[Comparative Example 1] to [Comparative Example 14]

An organic electroluminescent device was manufactured in the same manner as in Example 1, except that Comparative Compounds A to E were used as host materials for the emitting layer.

<Comparative Compound A>

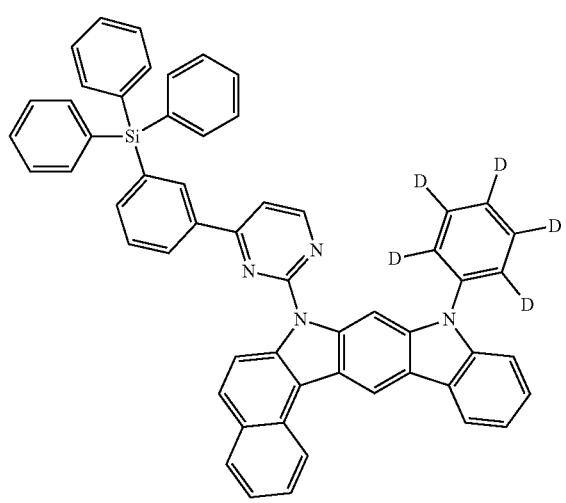

<Comparative Compound B>

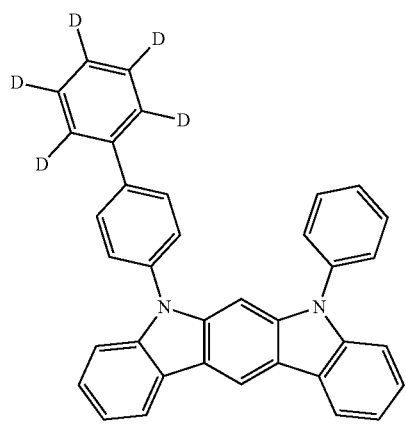

<Comparative Compound C>

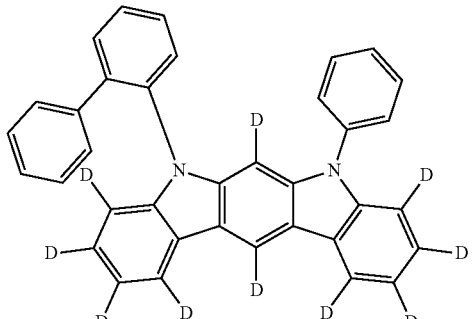

<Comparative Compound D>

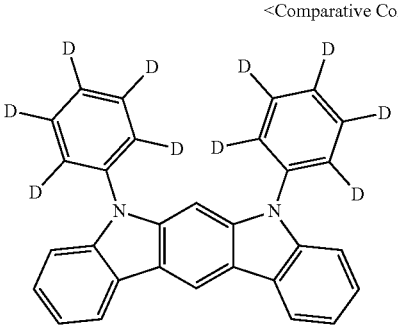

<Comparative Compound E>

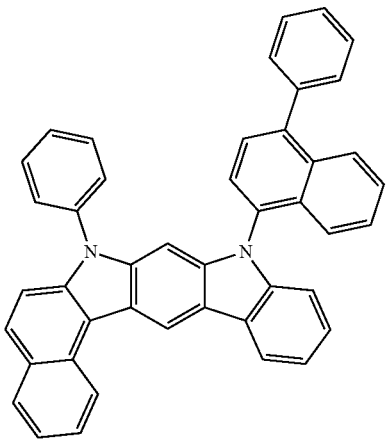

By applying a forward bias DC voltage to the organic electroluminescent devices prepared in Example 1 to Example 28 and Comparative Example 1 to Comparative Example 14 prepared in this way, Electroluminescence (EL) characteristics were measured with PR-650 from photo research, and as a result of the measurement, the T95 lifetime was measured using a lifetime measuring device manufactured by McScience at 2500 cd/m² standard luminance. Table 4 below shows the device fabrication and evaluation results.

TABLE 4

| | First compound | Second compound | Voltage | Current Density (mA/cm²) | Brightness (cd/A) | Efficiency (cd/m²) | T(95) |
|---|---|---|---|---|---|---|---|
| comparative example(1) | DSNL1 | comparative compound A | 5.4 | 11.7 | 2500 | 21.4 | 89.7 |
| comparative example(2) | | comparative compound B | 5.1 | 10.1 | 2500 | 24.8 | 110.7 |

TABLE 4-continued

| | First compound | Second compound | Voltage | Current Density (mA/cm$^2$) | Brightness (cd/A) | Efficiency (cd/m$^2$) | T(95) |
|---|---|---|---|---|---|---|---|
| comparative example(3) | | comparative compound C | 5.2 | 11.3 | 2500 | 22.1 | 105.6 |
| comparative example(4) | | comparative compound D | 5.3 | 11.4 | 2500 | 22.0 | 104.4 |
| comparative example(5) | | comparative compound E | 5.1 | 10.7 | 2500 | 23.3 | 99.2 |
| comparative example(6) | DSNL2 | comparative compound A | 5.5 | 11.2 | 2500 | 22.3 | 90.4 |
| comparative example(7) | | comparative compound B | 5.2 | 10.1 | 2500 | 24.8 | 112.8 |
| comparative example(8) | | comparative compound C | 5.3 | 11.8 | 2500 | 21.2 | 107.4 |
| comparative example(9) | | comparative compound D | 5.3 | 10.8 | 2500 | 23.2 | 105.1 |
| comparative example(10) | | comparative compound E | 5.2 | 10.4 | 2500 | 24.1 | 100.9 |
| example(1) | DSNL1 | P-2 | 4.5 | 7.6 | 2500 | 32.7 | 144.0 |
| example(2) | | P-3 | 4.7 | 7.5 | 2500 | 33.4 | 140.4 |
| example(3) | | P-8 | 4.5 | 7.9 | 2500 | 31.6 | 137.8 |
| example(4) | | P-17 | 4.4 | 8.0 | 2500 | 31.3 | 136.6 |
| example(5) | | P-22 | 4.6 | 8.1 | 2500 | 31.0 | 135.3 |
| example(6) | | P-37 | 4.4 | 7.6 | 2500 | 33.0 | 142.8 |
| example(7) | | P-39 | 4.6 | 7.4 | 2500 | 33.7 | 141.1 |
| example(8) | | P-45 | 4.3 | 8.2 | 2500 | 30.4 | 127.9 |
| example(9) | | P-52 | 4.3 | 8.4 | 2500 | 29.7 | 129.2 |
| example(10) | | P-56 | 4.5 | 8.5 | 2500 | 29.3 | 130.4 |
| example(11) | | P-61 | 4.4 | 8.3 | 2500 | 30.0 | 131.6 |
| example(12) | | P-70 | 4.4 | 8.2 | 2500 | 30.7 | 132.8 |
| example(13) | | P-77 | 4.7 | 7.7 | 2500 | 32.5 | 134.1 |
| example(14) | | P-85 | 4.6 | 7.8 | 2500 | 32.0 | 139.1 |
| example(15) | DSNL2 | P-2 | 4.7 | 7.6 | 2500 | 33.1 | 145.2 |
| example(16) | | P-3 | 4.8 | 7.4 | 2500 | 33.7 | 141.5 |
| example(17) | | P-8 | 4.6 | 7.8 | 2500 | 32.0 | 139.0 |
| example(18) | | P-17 | 4.6 | 7.9 | 2500 | 31.8 | 137.8 |
| example(19) | | P-22 | 4.6 | 8.0 | 2500 | 31.4 | 136.6 |
| example(20) | | P-37 | 4.6 | 7.5 | 2500 | 33.4 | 143.0 |
| example(21) | | P-39 | 4.7 | 7.3 | 2500 | 34.1 | 142.9 |
| example(22) | | P-45 | 4.5 | 7.9 | 2500 | 31.7 | 129.1 |
| example(23) | | P-52 | 4.4 | 8.3 | 2500 | 30.0 | 130.4 |
| example(24) | | P-56 | 4.6 | 8.4 | 2500 | 29.7 | 131.6 |
| example(25) | | P-61 | 4.5 | 8.2 | 2500 | 30.4 | 132.9 |
| example(26) | | P-70 | 4.5 | 8.1 | 2500 | 31.0 | 134.4 |
| example(27) | | P-77 | 4.9 | 7.6 | 2500 | 32.8 | 135.3 |
| example(28) | | P-85 | 4.8 | 7.7 | 2500 | 32.4 | 140.1 |

Referring to Table 4, when the compound of the present invention is used as a light emitting layer material, it can be seen that the driving voltage is lowered and the efficiency and lifespan are remarkably improved compared to the case of using Comparative Compounds A to E.

More specifically, in the case of Comparative Compound A, it includes a skeleton similar to that of the present invention. However, the type of the substituted substituent is different in that it contains azines among heterocyclic groups and contains silicon as a secondary substituent, all of which negatively affect the lifespan. The reason is that, in the present invention, two types of compounds having different properties are mixed and measured when used as a light emitting layer material. In the case of Comparative Compound A, it is amplified with the electrical properties of the mixed material as a compound with strong electrical properties, thereby deteriorating the electrical properties inside the light emitting layer. In the case of Comparative Compounds B to D, deuterium described in the present invention is substituted, but the additionally condensed portions in the backbone are different from each other. In the case of the structure with the added condensation described in the present invention, it can be seen that the hole injection characteristic is further improved and the HOD is faster than that of the non-condensed skeleton. Finally, in the case of Comparative Compound E, deuterium is not substituted. In the present invention, it can be seen that the device result is improved according to the position at which deuterium is substituted. The device performance related to such deuterium substitution shows the hole mobility difference characteristic of the compound due to the difference in the degree of distortion between the backbone and the substituent that becomes the core as deuterium is substituted. Also, compounds have different distances, and these distances show a positive effect by smooth interaction with adjacent layers. As a result of examining the characteristics of the present invention, it was confirmed that when the position of deuterium was present in the linking group, the effect of improvement in terms of driving, efficiency, and lifespan was the greatest, and the case where the deuterium was substituted at the terminal showed excellent performance. These results showed an excellent effect on hole movement by appropriately adjusting the distance between the same material and adjacent layers as deuterium was substituted at a specific position as described above.

In addition, even when all deuterium is substituted in one substituent or deuterium is substituted in the backbone that becomes the core, the device performance is improved

What is claimed is:

1. A compound represented by Formula (1):

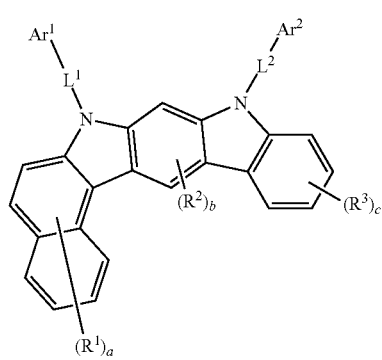

Formula (1)

wherein:
1) $Ar^1$ and $Ar^2$ are each independently of a $C_6$-$C_{60}$ aryl group; or $C_2$-$C_{60}$ heteroaryl group;
2) $L^1$ and $L^2$ are each independently selected from the group consisting of a single bond; $C_6$-$C_{60}$ arylene group; and $C_2$-$C_{60}$ heteroarylene group;
3) $R^1$, $R^2$ and $R^3$ are the same or different from each other, and independently of each other are hydrogen or deuterium;
4) a is an integer of 0 to 6, b is and integer of 0 to 2, c is an integer of 0 to 4,
wherein the aryl group, arylene group, heteroaryl group, heteroarylene group may be substituted with one or more substituents selected from the group consisting of deuterium; halogen; cyano group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof,
with the proviso that:
at least one of $Ar^1$, $Ar^2$, $L^1$, $L^2$, $R^1$, $R^2$ and $R^3$ is substituted with deuterium, and
a compound of Formula (2) is excluded from Formula (1):

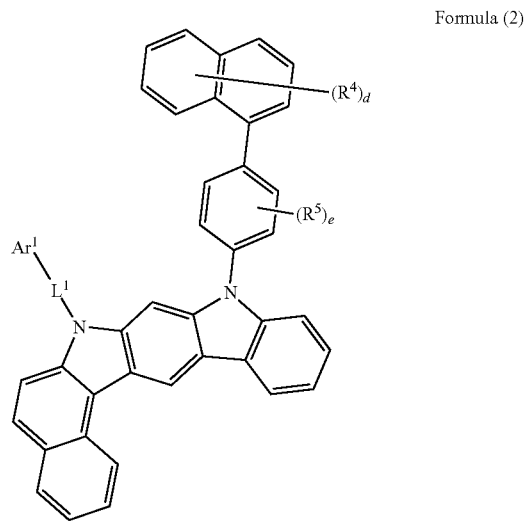

Formula (2)

wherein $Ar^1$ and $L^1$ are the same as defined above for Formula (1), $R^4$ and $R^5$ are each independently hydrogen or deuterium, d is an integer from 0 to 7, and e is an integer from 0 to 4.

2. The compound of claim 1, wherein one of $L^1$ and $L^2$ is substituted with deuterium.

3. The compound of claim 1, wherein one of $L^1$ and $L^2$ is a $C_6$-$C_{60}$ arylene group substituted with deuterium.

4. The compound of claim 1, wherein one of $Ar^1$ and $Ar^2$ is substituted with deuterium.

5. The compound of claim 1, wherein one of $Ar^1$ and $Ar^2$ is a $C_6$-$C_{60}$ aryl group substituted with deuterium.

6. The compound of claim 1, wherein one of $R^1$ to $R^3$ is deuterium.

7. The compound of claim 1, wherein at least one of $Ar^1$ and $Ar^2$ is represented by Formula (3):

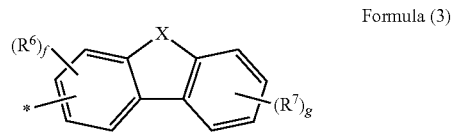

Formula (3)

wherein:
1) $R^6$ and $R^7$ are the same or different from each other, and are each independently selected from the group consisting of a hydrogen; deuterium; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-$NR^aR^b$; or an adjacent plurality of $R^6$s, or a plurality of $R^7$s may be bonded to each other to form a ring;
(2) L' is selected from the group consisting of single bond; a $C_6$-$C_{60}$ arylene group; a $C_2$-$C_{60}$ heterocyclic group including at least one heteroatom of O, N, S, Si or P;
(3) $R^a$ and $R^b$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; an $C_2$~$C_{20}$ alkenyl group; a $C_2$-$C_{20}$ alkynyl group; a $C_1$-$C_{30}$ alkoxy group; and a $C_6$-$C_{30}$ aryloxy group;

(4) f is an integer from 0 to 3, g is an integer from 0 to 4;

(5) * means the combined position;

(6) X is NR', O or S;

(7) R' is a $C_6$-$C_{60}$ aryl group; or $C_2$-$C_{60}$ heteroaryl group, with the proviso that one of $Ar^1$, $Ar^2$, $L^1$, $L^2$, $R^1$, $R^2$, $R^3$, $R^6$ and $R^7$ is substituted with deuterium.

8. The compound of claim 1, wherein $L^1$ and $L^2$ are each independently a $C_6$-$C_{30}$ arylene group, $Ar^1$ and $Ar^2$ are each independently a $C_6$-$C_{30}$ aryl group; and at least one of $L^1$, $L^2$, $Ar^1$ and $Ar^2$ is substituted with deuterium.

9. The compound of claim 1, wherein $L^2$ is a $C_6$-$C_{30}$ arylene group substituted with deuterium, and $L^1$, $Ar^1$, $Ar^2$, $R^1$, $R^2$ and $R^3$ are not substituted with deuterium.

10. The compound of claim 1, wherein $Ar^2$ is a $C_6$-$C_{30}$ aryl group substituted with deuterium, and $L^1$, $L^2$, $Ar^1$, $R^1$, $R^2$ and $R^3$ are not substituted with deuterium.

11. The compound of claim 1, wherein Formula (1) is represented by any of Formulas (1-a) to (1-d) and (1-h) to (1-q):

Formula (1-a)

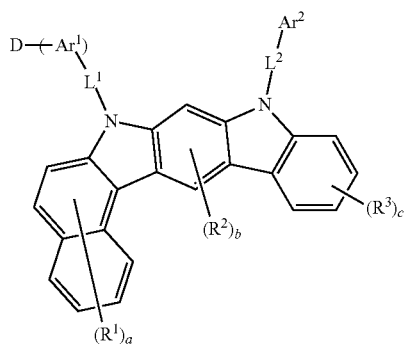

Formula (1-b)

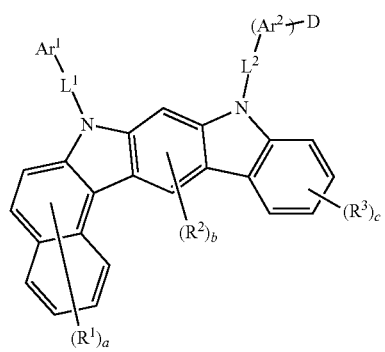

Formula (1-c)

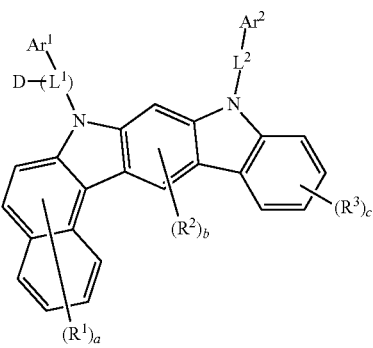

Formula (1-d)

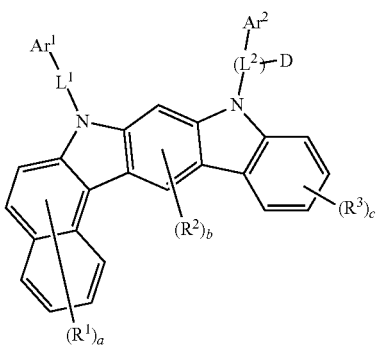

Formula (1-h)

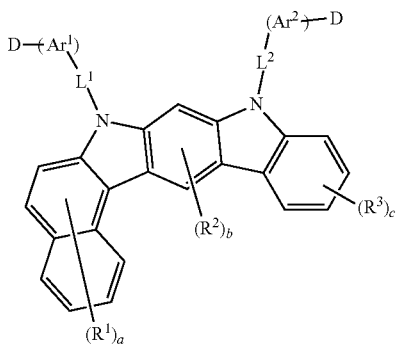

Formula (1-i)

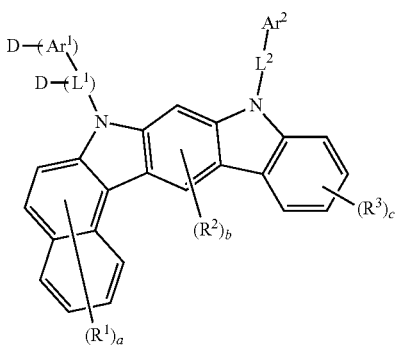

Formula (1-j)
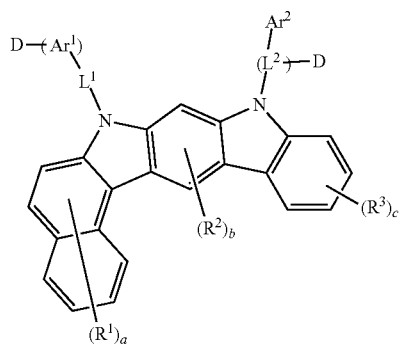
Formula (1-k)
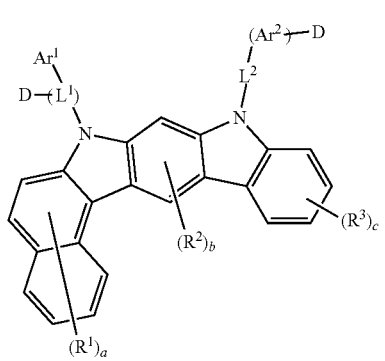
Formula (1-l)
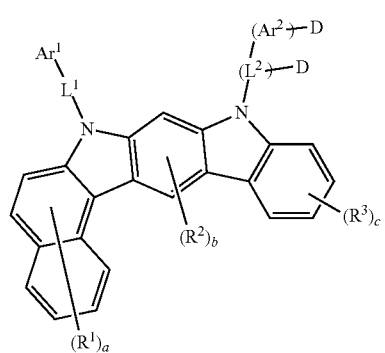
Formula (1-m)
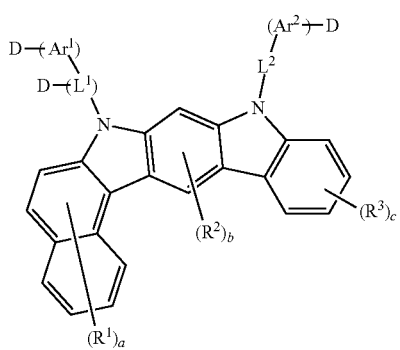
Formula (1-n)
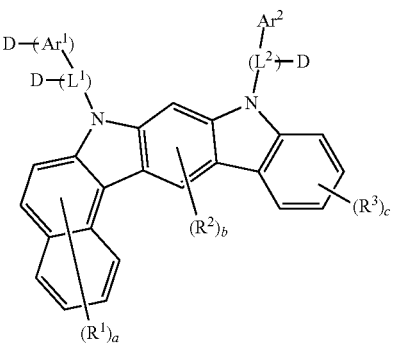
Formula (1-o)
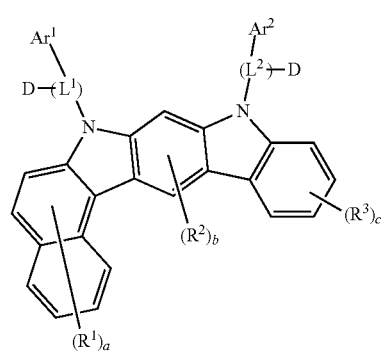
Formula (1-p)
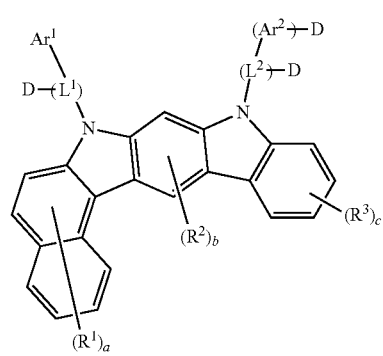
Formula (1-q)
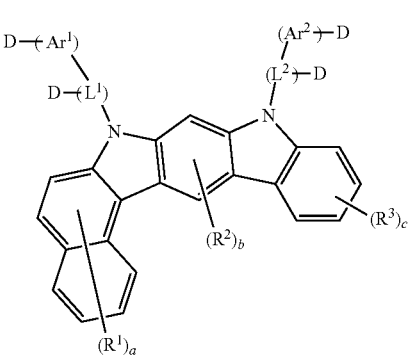
wherein, $Ar^1$, $Ar^2$, $L^1$, $L^2$, $R^1$, $R^2$, $R^3$, a, b and c are the same as defined in claim 1.

12. The compound of claim 1, wherein Formula (1) is represented by any of compounds P-1 to P-90:
P-1
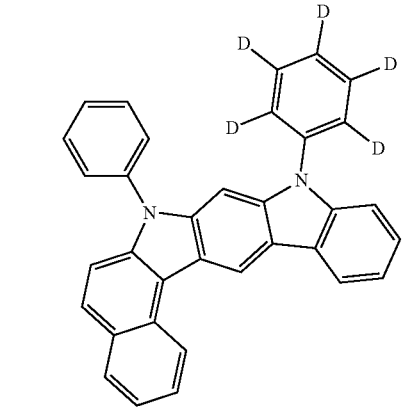
P-2
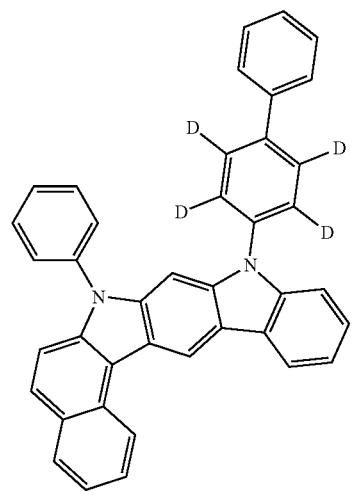
P-3
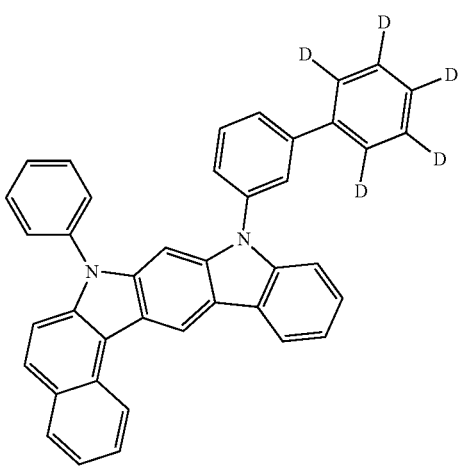
P-4
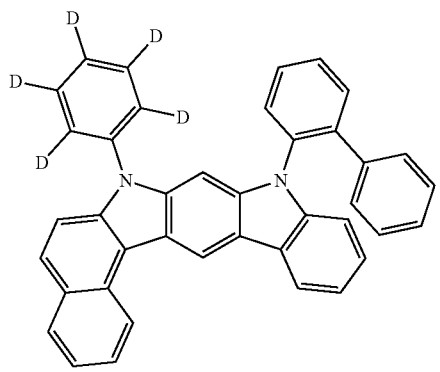
P-5
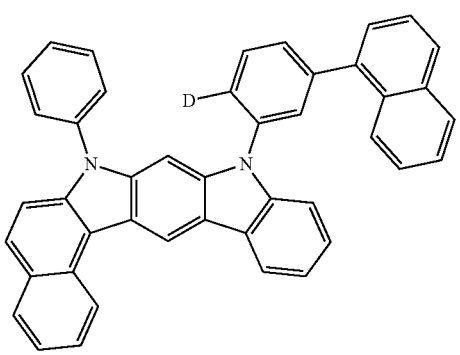
P-6
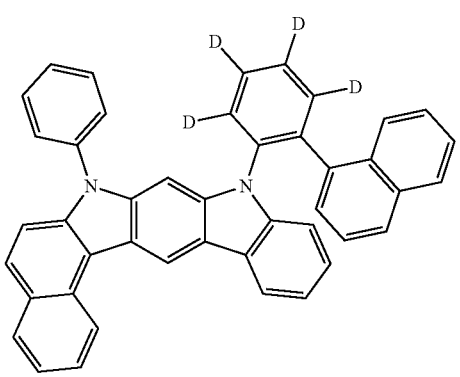
P-7
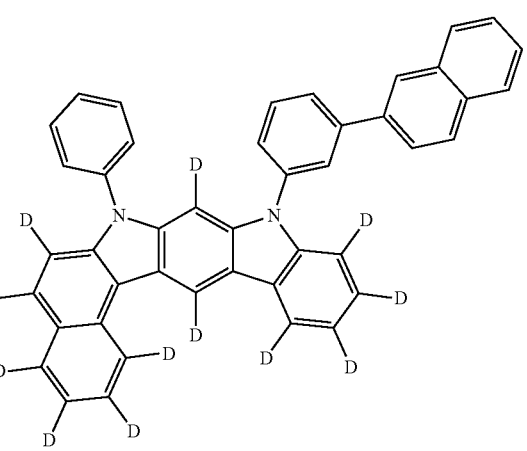

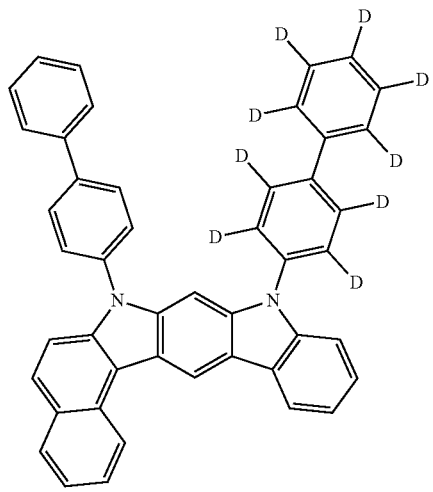
P-8
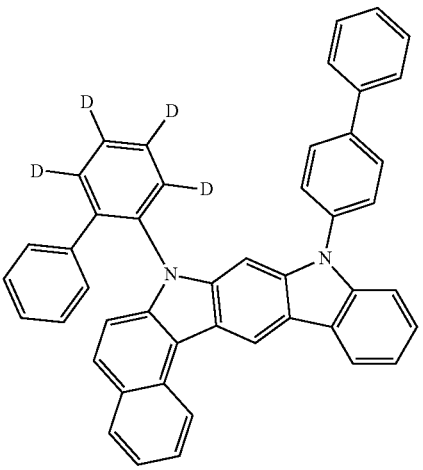
P-11
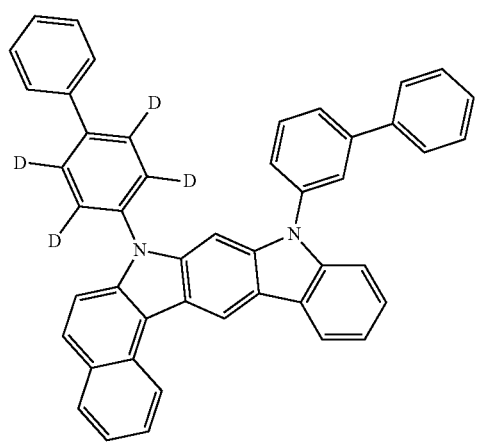
P-9
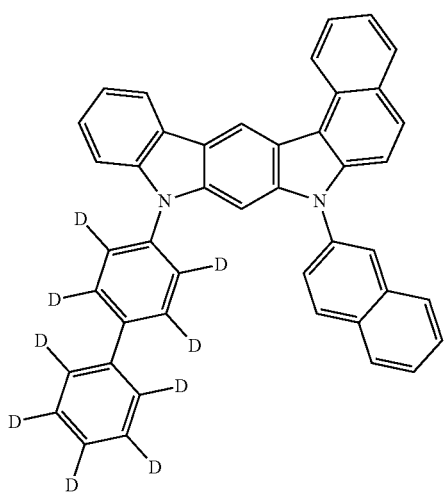
P-12
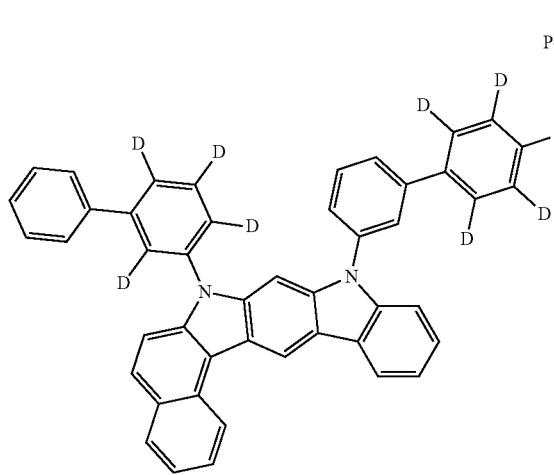
P-10
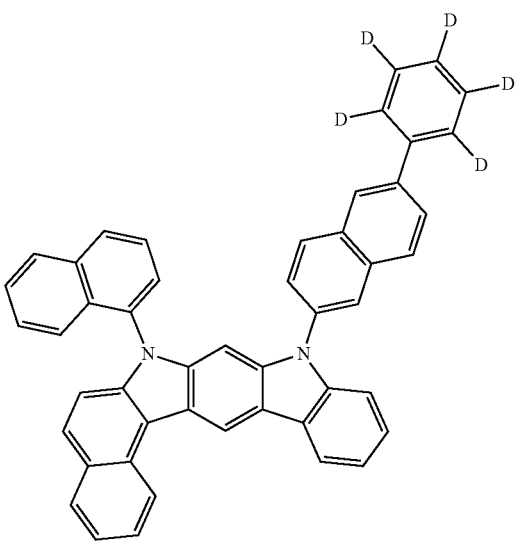
P-13

P-14
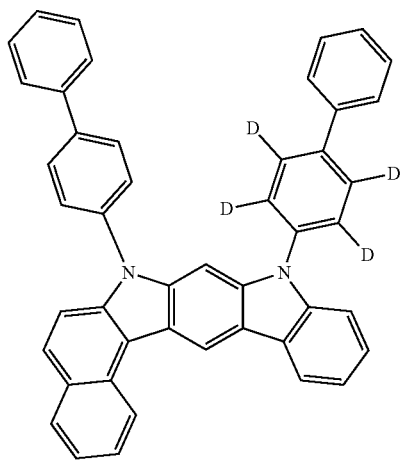
P-15
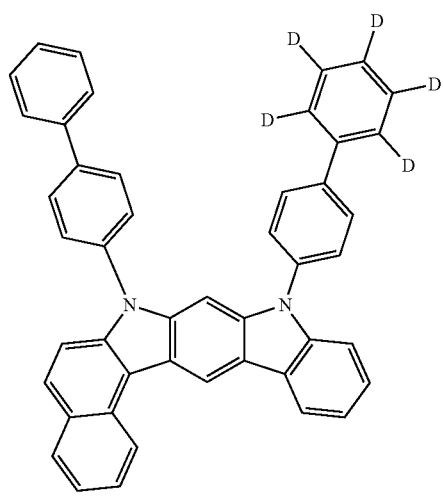
P-16
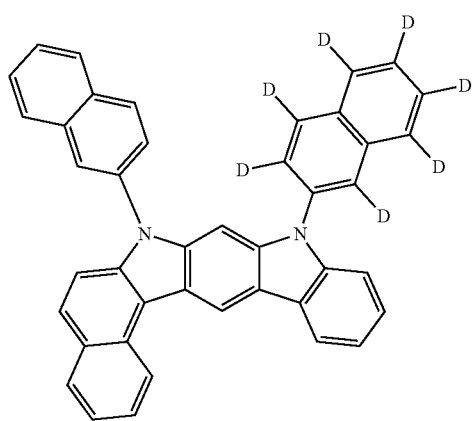
P-17
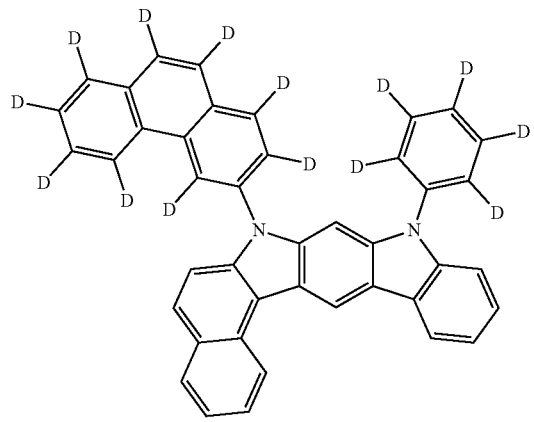
P-18
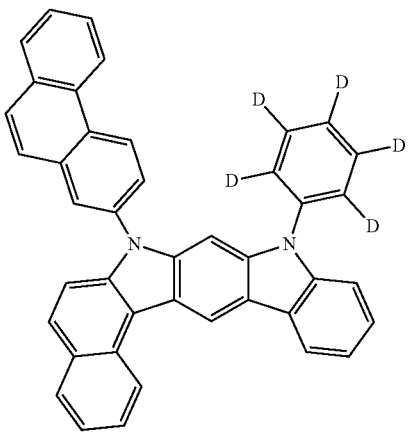
P-19
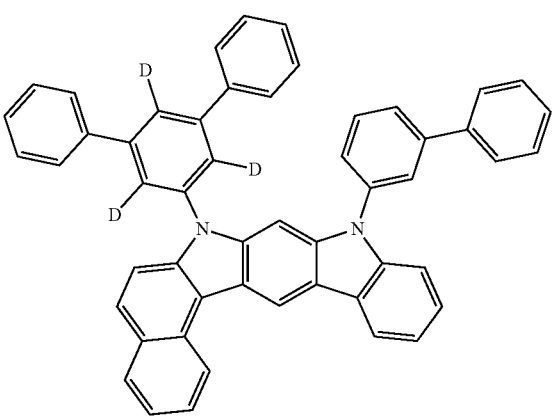

P-20
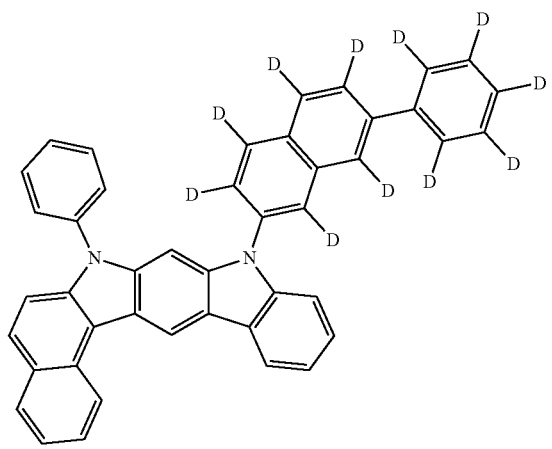
P-21
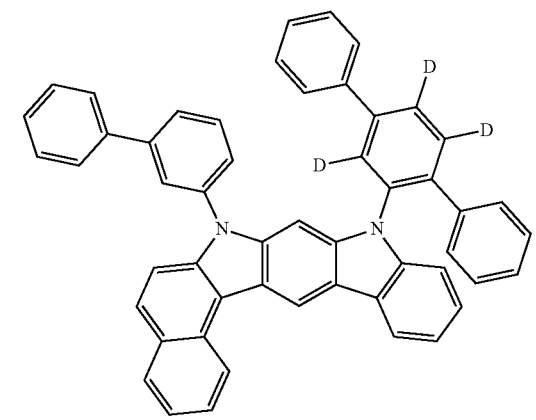
P-22
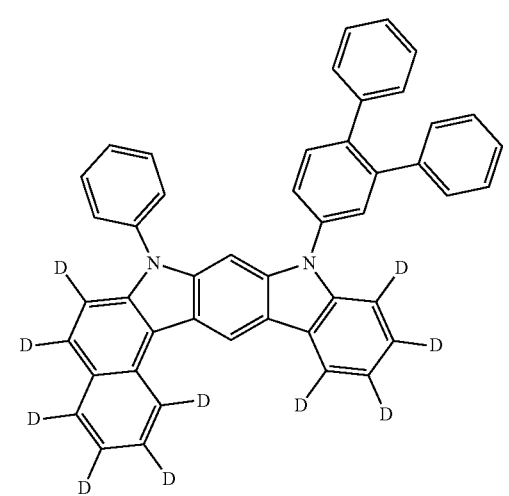
P-23
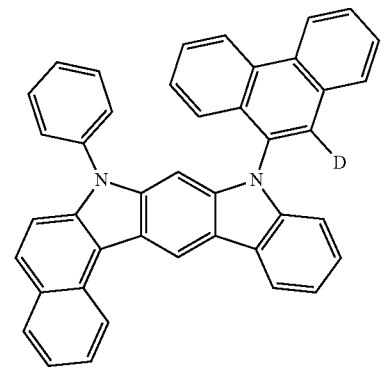
P-24
P-25
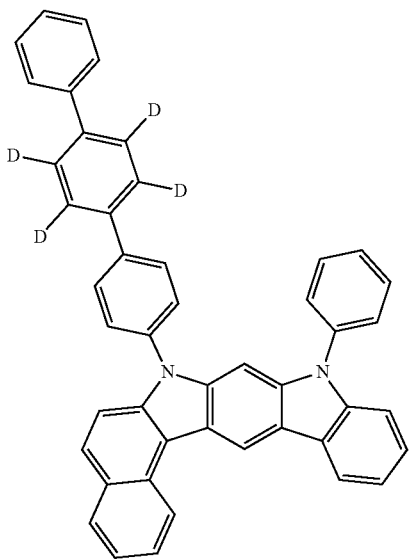

-continued
P-26
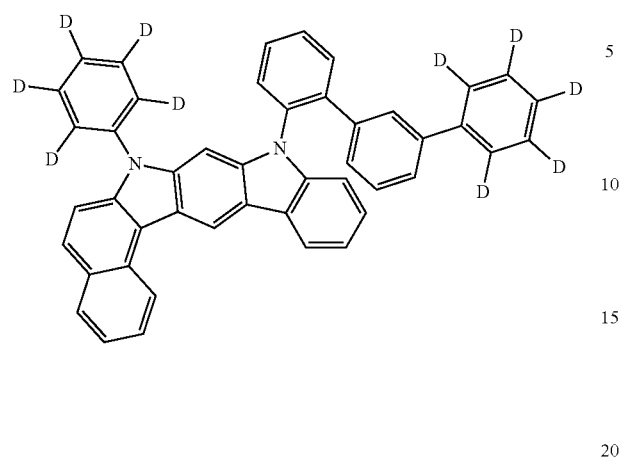
P-27
P-28
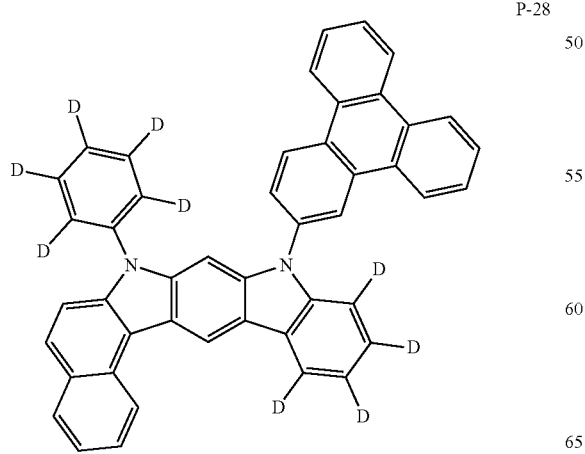
-continued
P-29
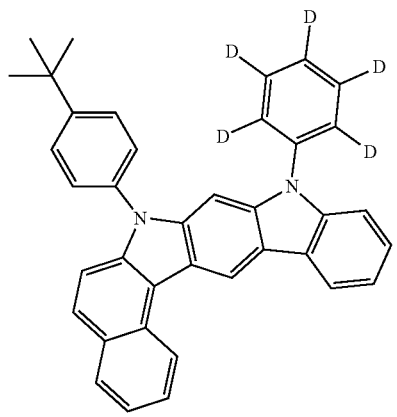
P-30
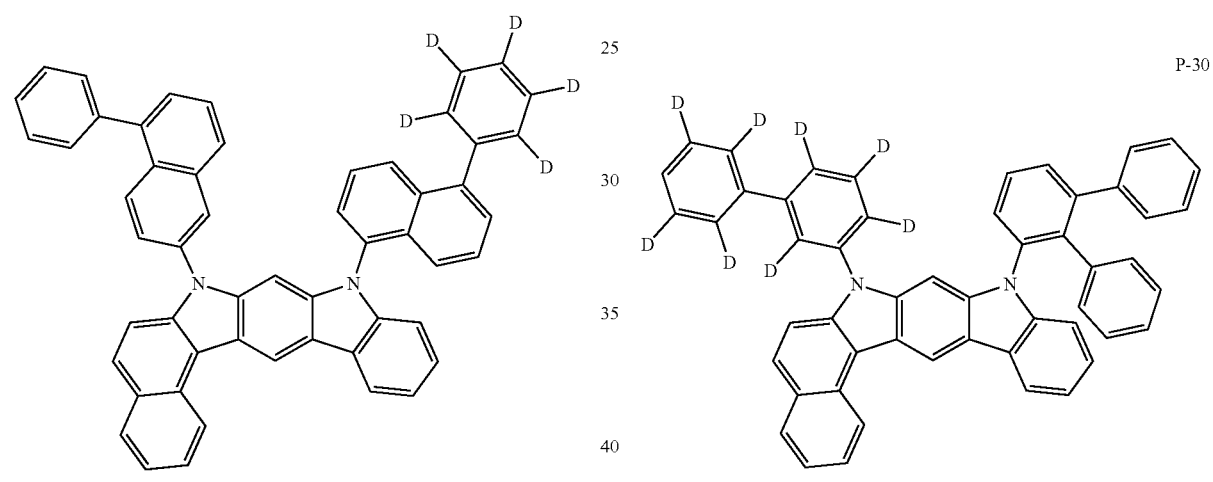
P-31
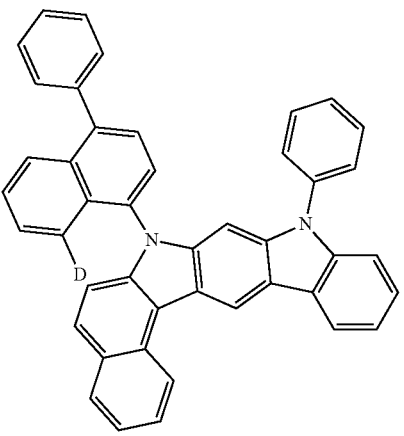

-continued
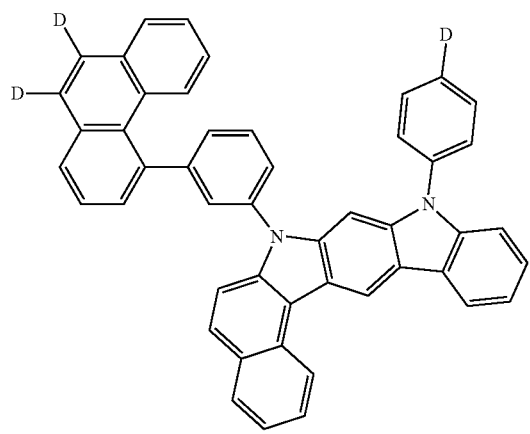
P-32
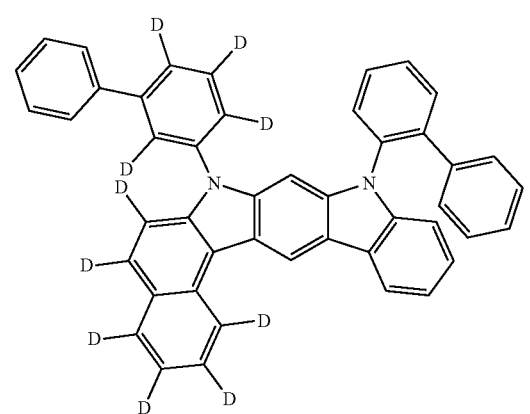
P-33
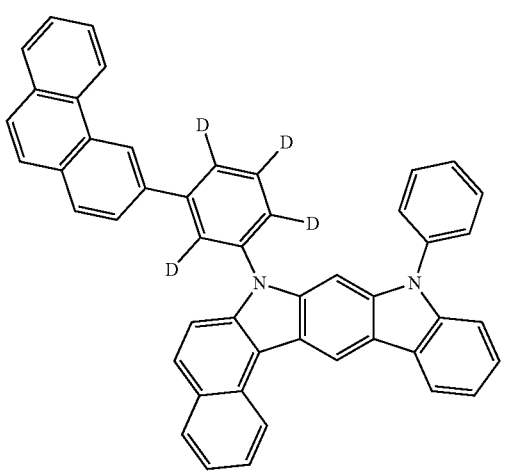
P-34
-continued
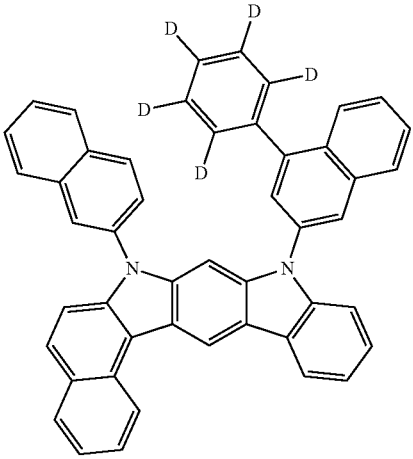
P-35
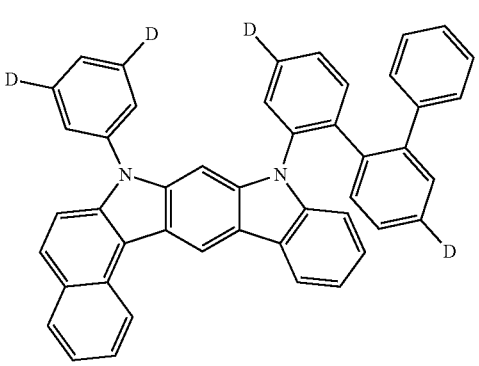
P-36
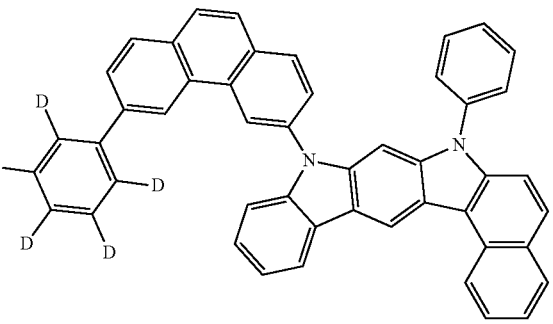
P-37
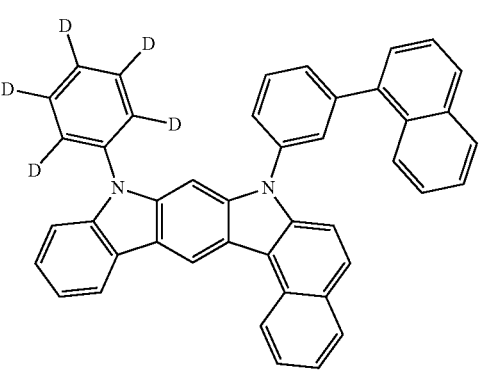
P-38

P-39
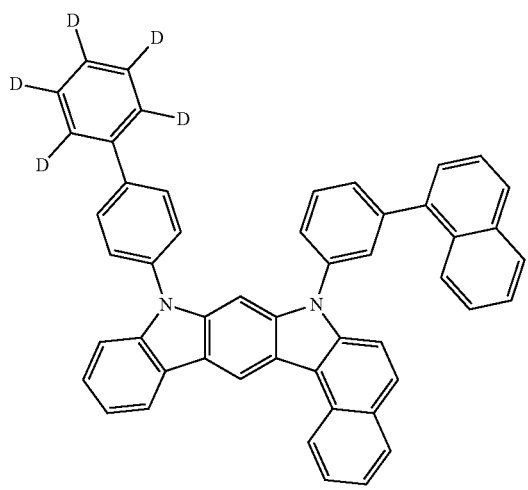
P-40
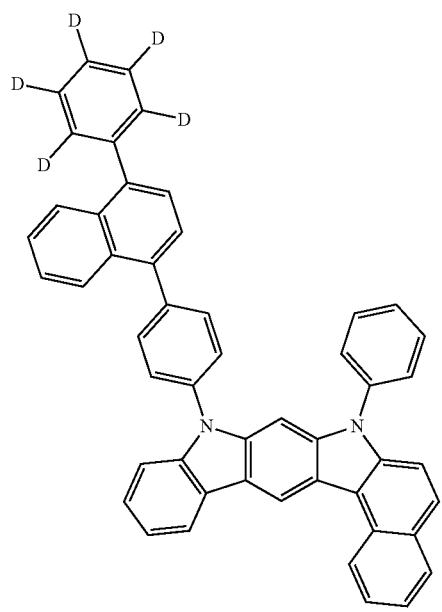
P-41
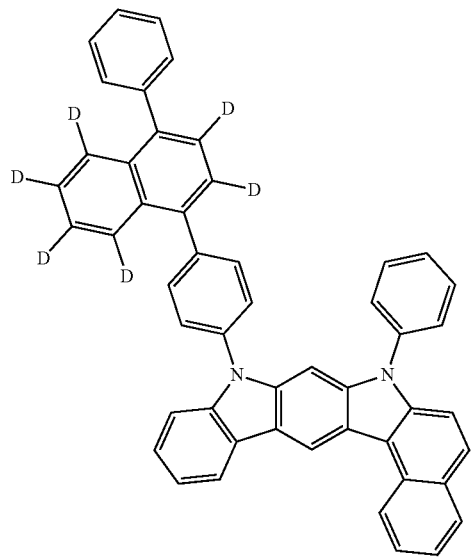
P-42
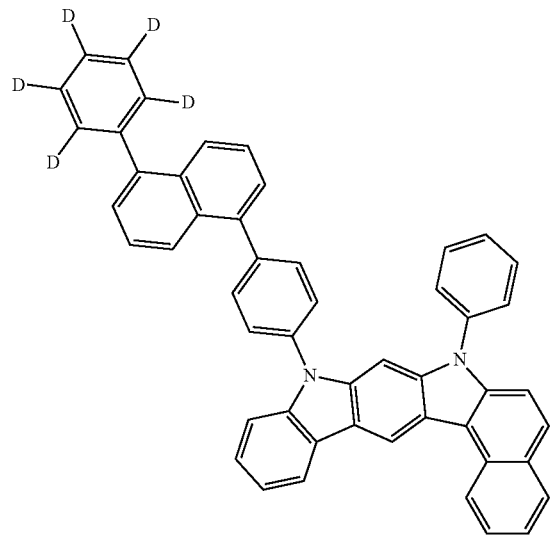
P-43
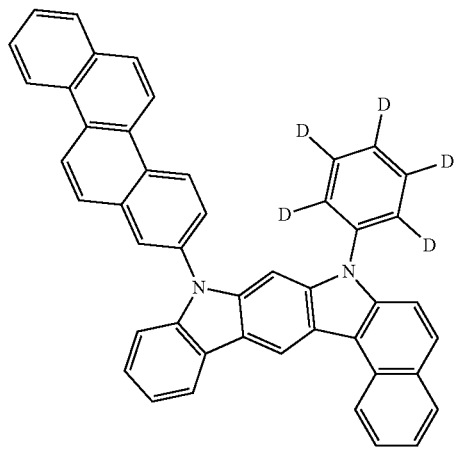
P-44
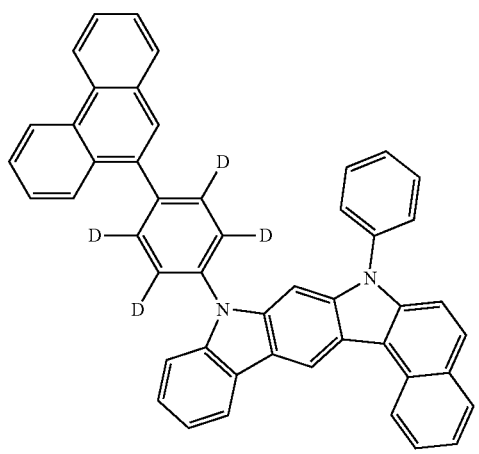

P-45
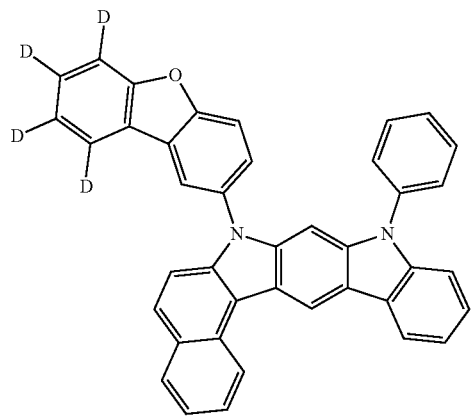
P-46
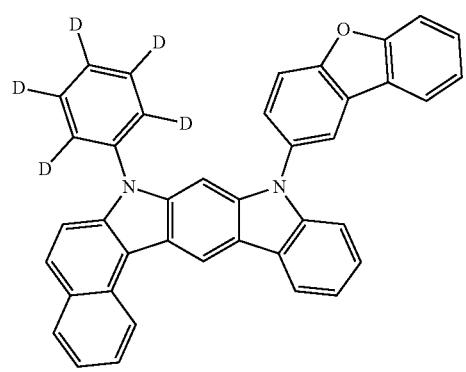
P-47
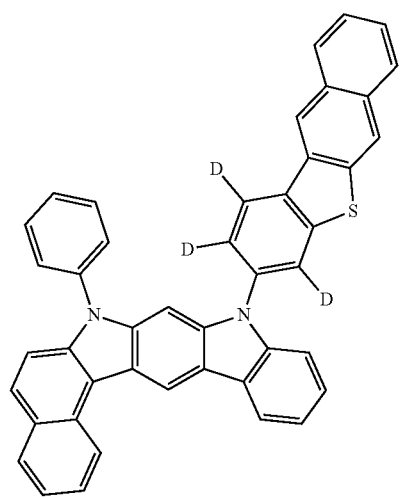
P-48
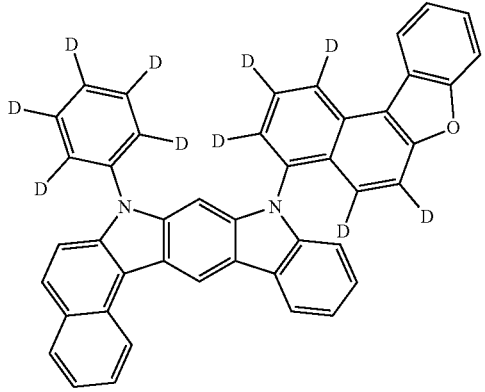
P-49
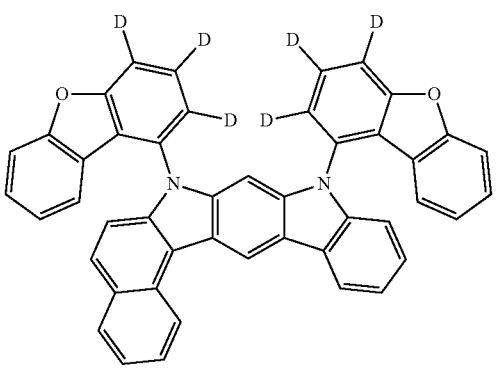
P-50
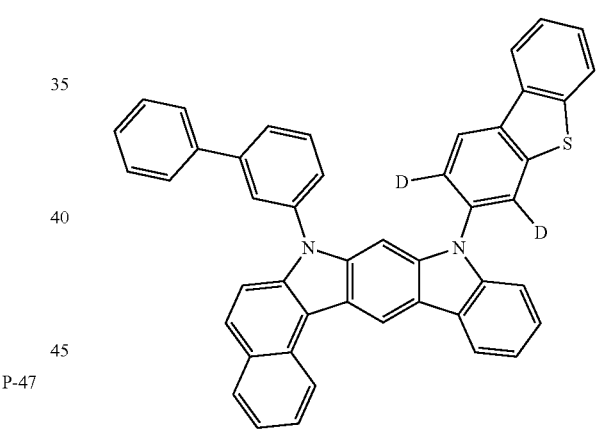
P-51
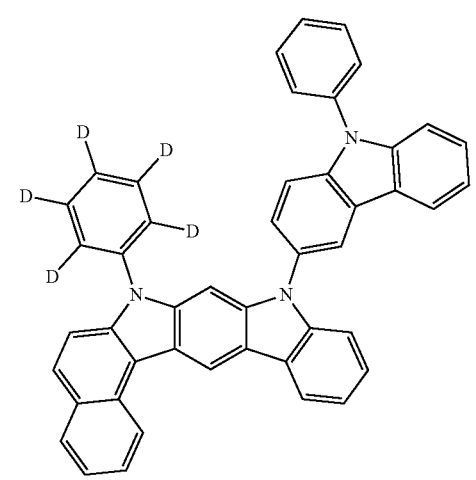

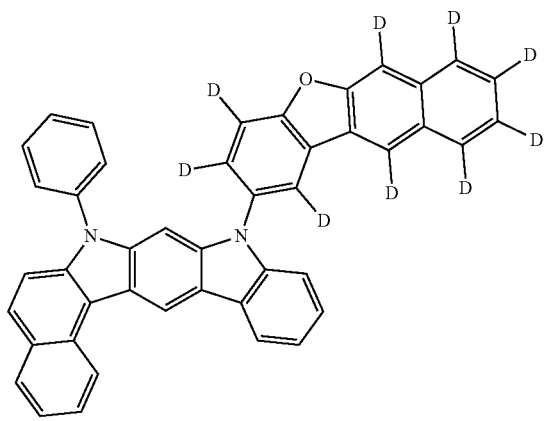
P-52
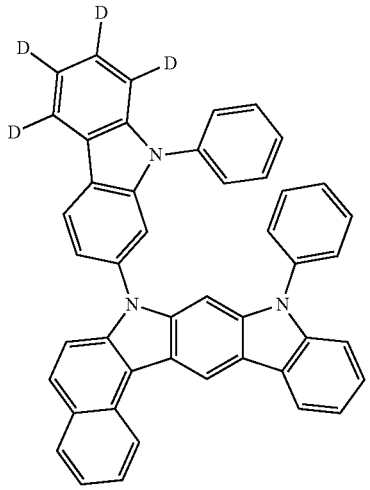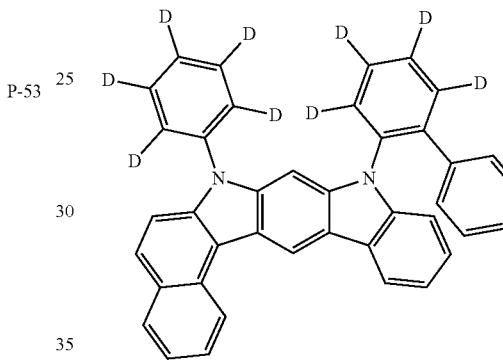
P-55
P-56
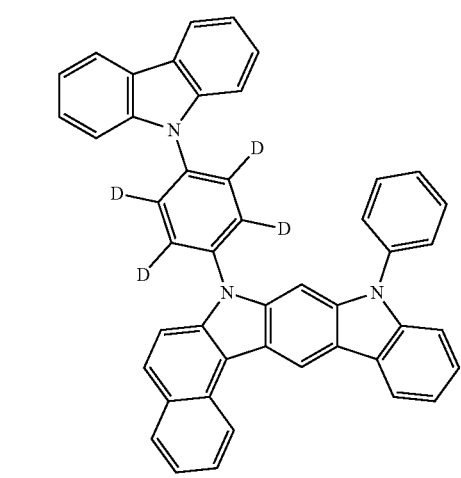
P-53
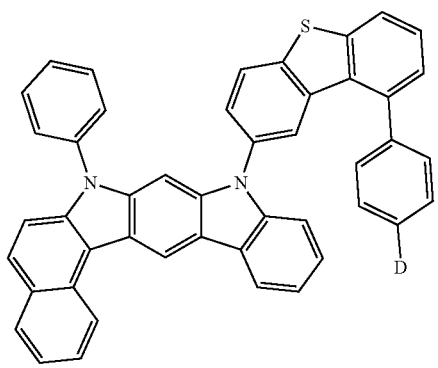
P-57
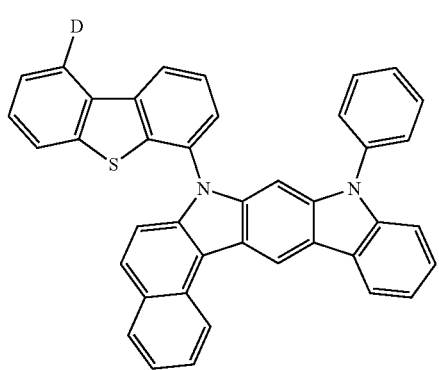
P-54
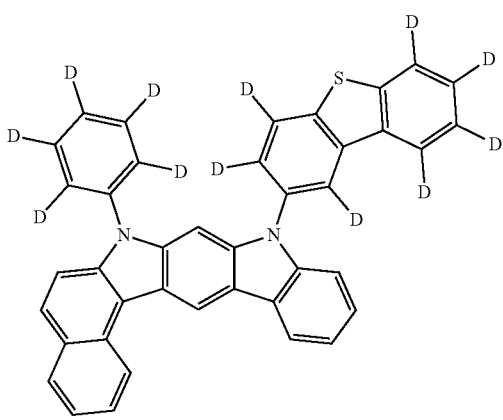
P-58

-continued
P-59
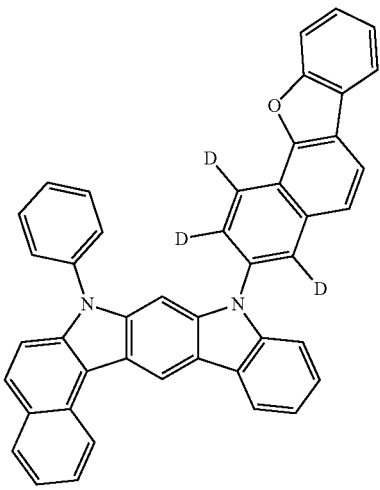
P-60
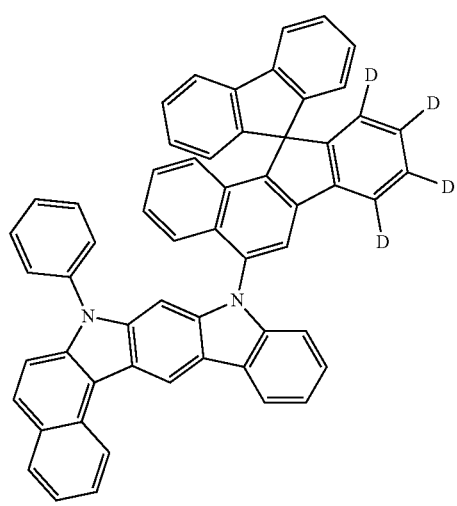
P-61
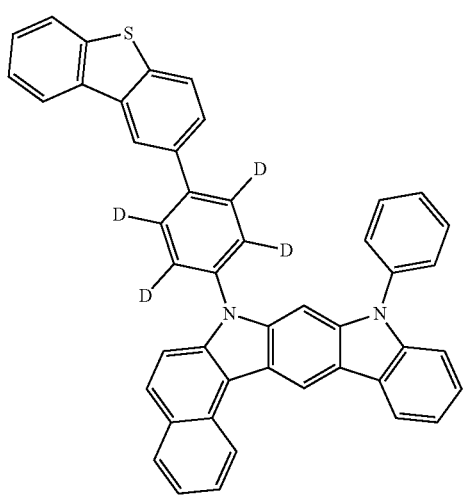
-continued
P-62
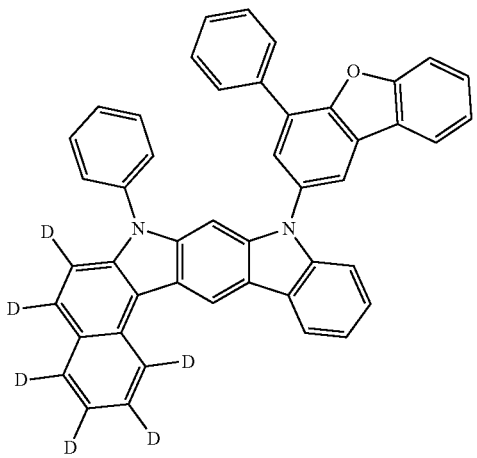
P-63
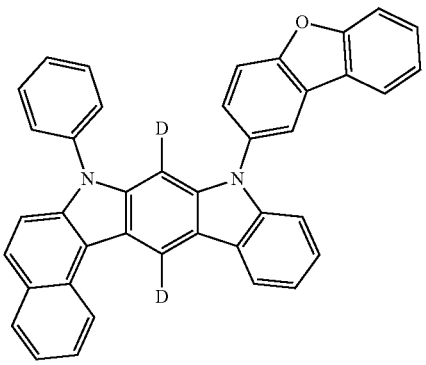
P-64
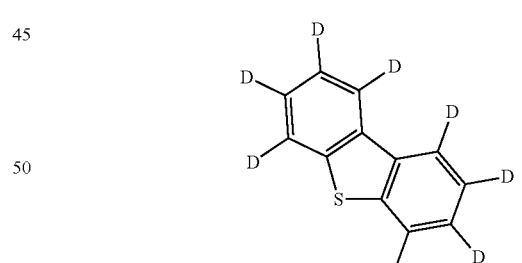
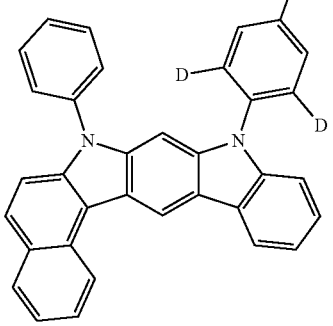

P-65
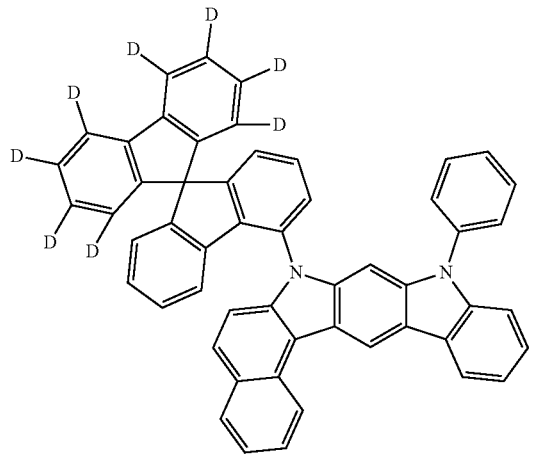
P-66
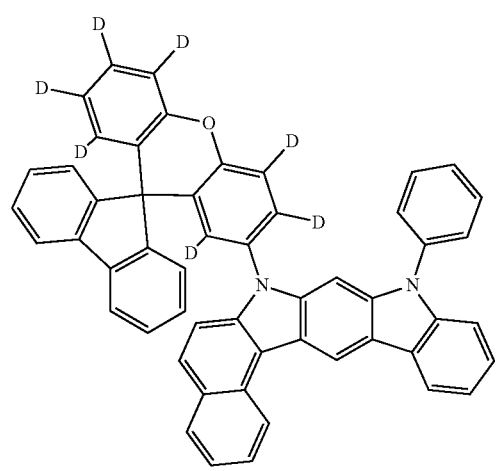
P-67
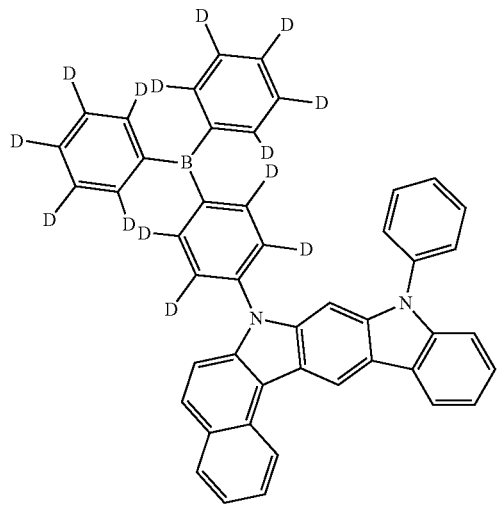
P-68
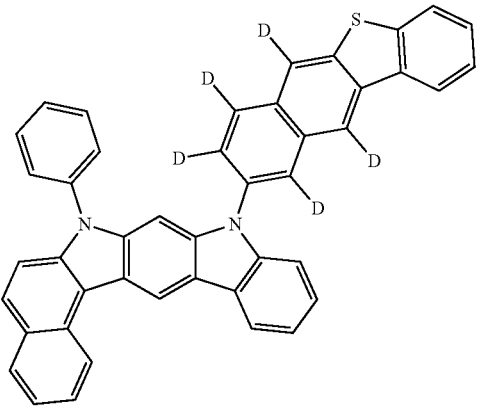
P-69
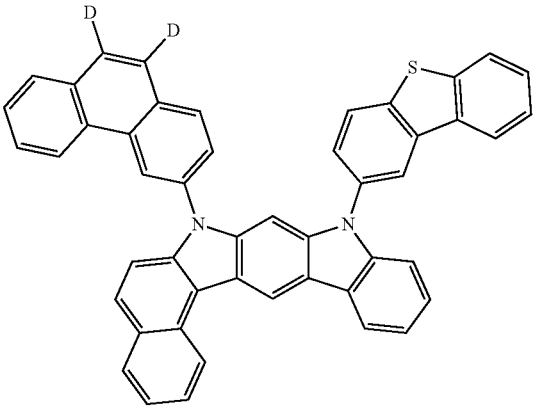
P-70
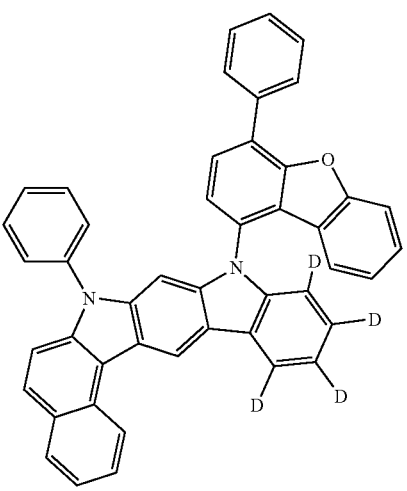

-continued
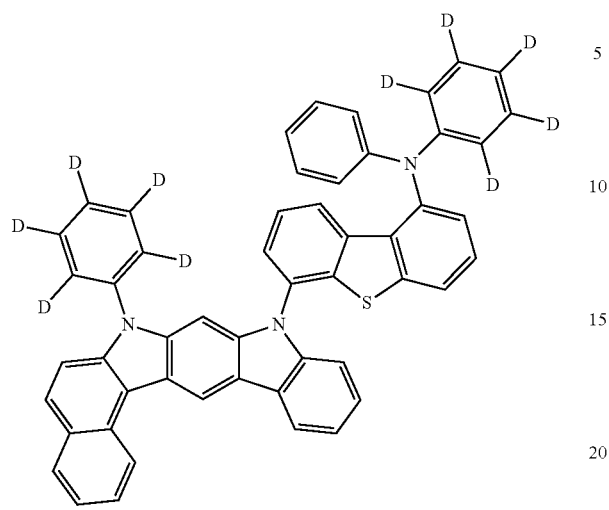
P-71
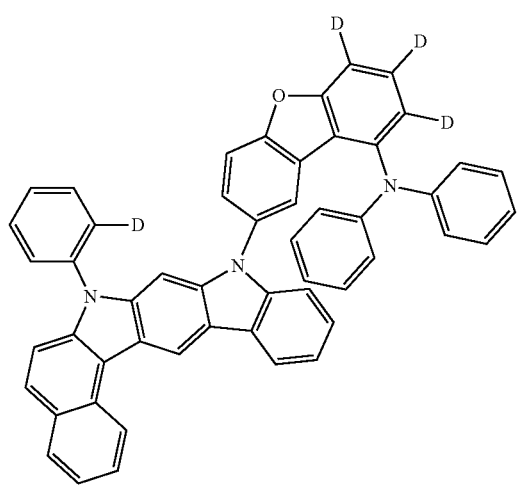
P-72
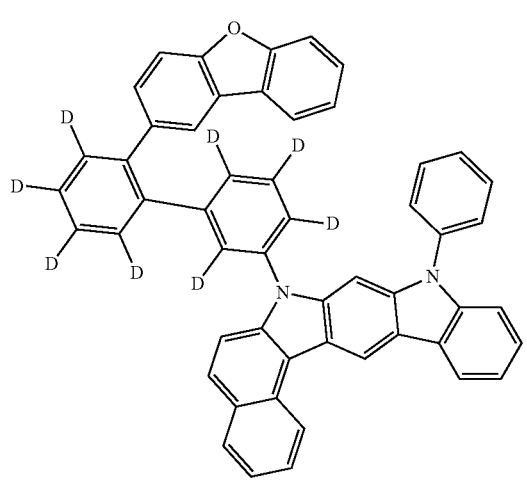
P-73
-continued
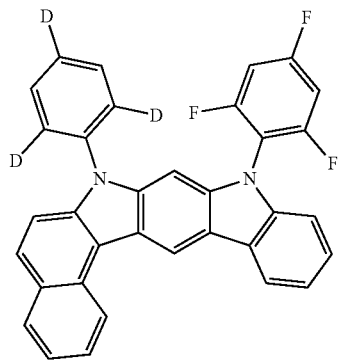
P-74
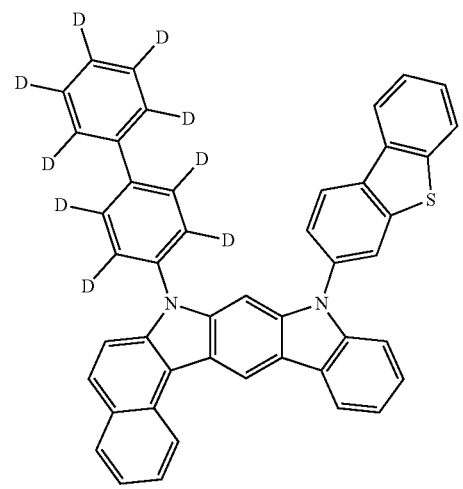
P-75
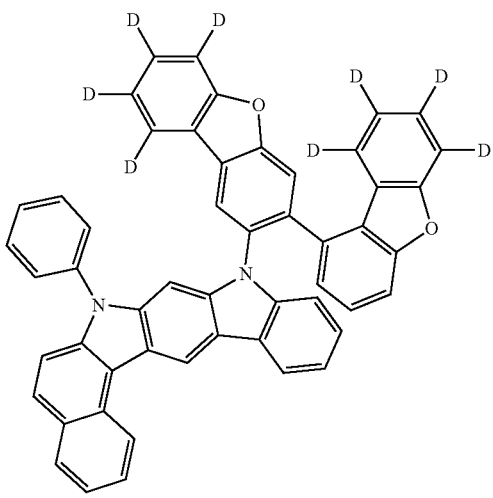
P-76

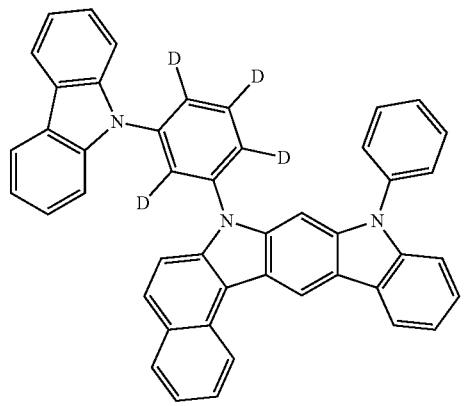
P-77
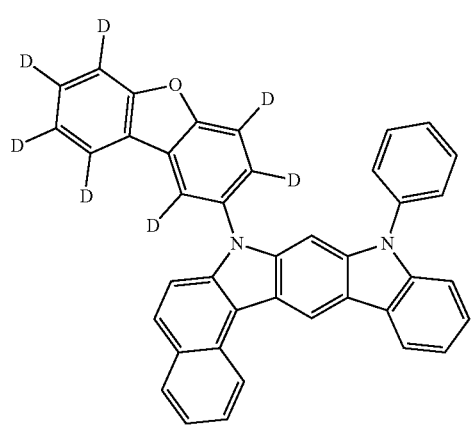
P-78
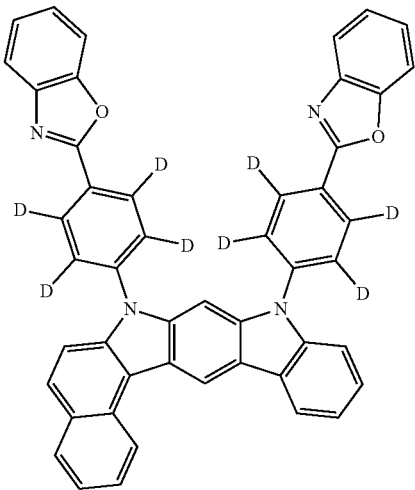
P-79
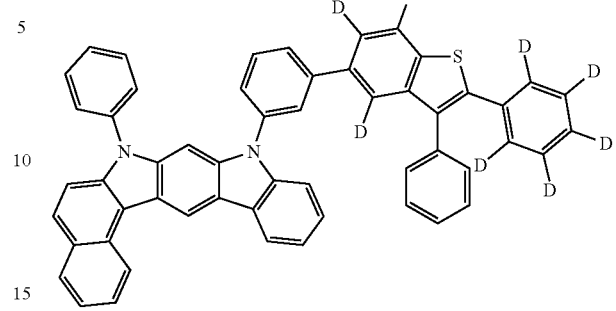
P-80
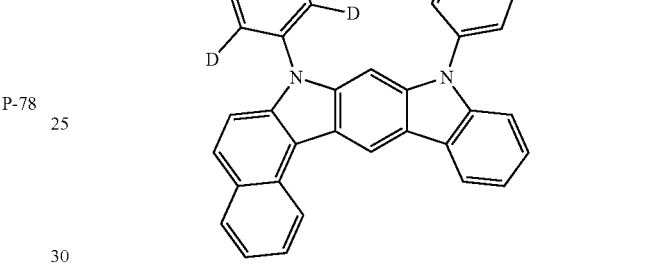
P-81
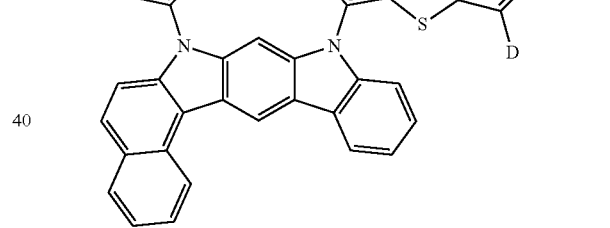
P-82
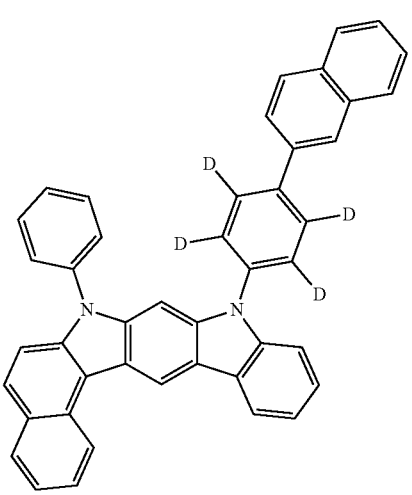
P-83

-continued
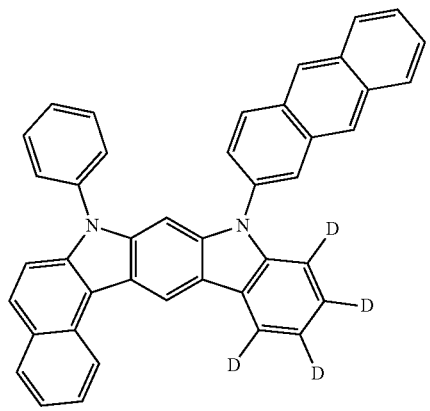
P-84
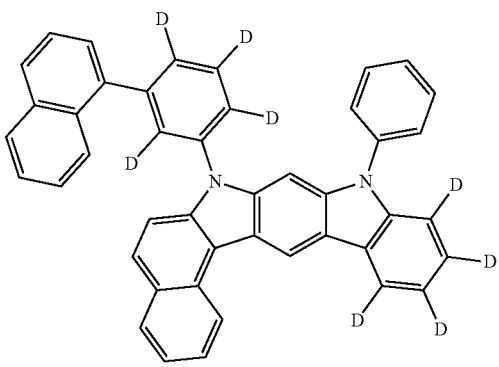
P-85
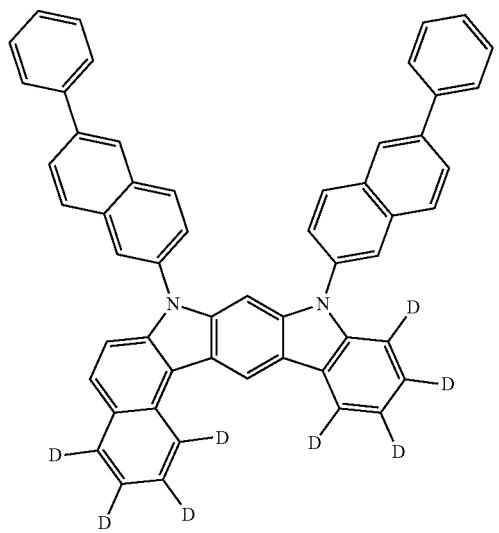
P-86
-continued
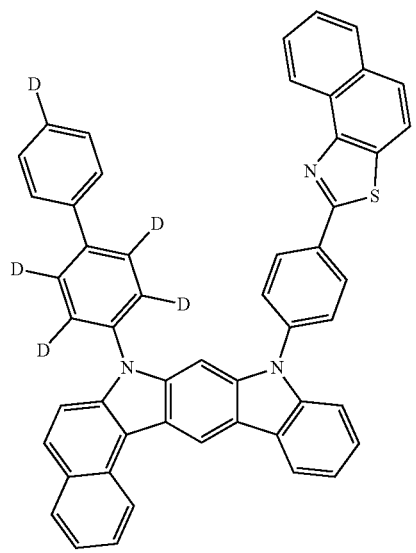
P-87
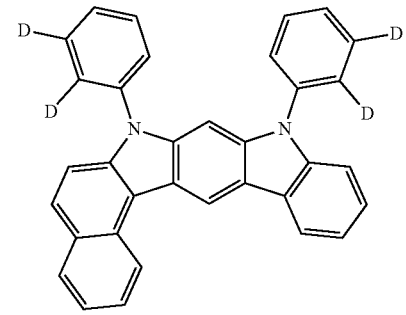
P-88
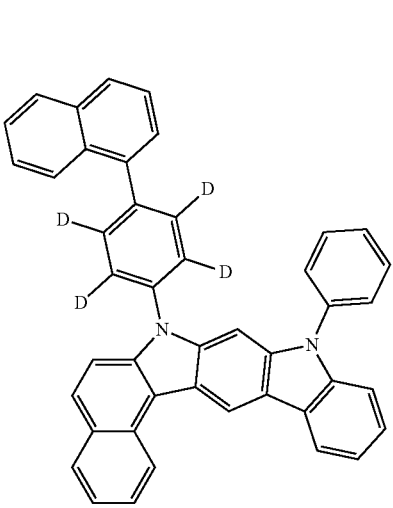
P-89

-continued

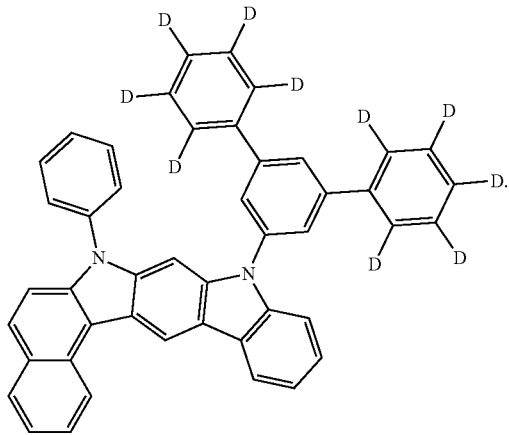

P-90

13. An organic electronic element comprising an anode, a cathode, and an organic material layer formed between the anode and the cathode, wherein the organic material layer comprises a single compound or 2 or more compounds represented by Formula (1) of claim 1.

14. The organic electronic element of claim 13, wherein the organic material layer comprises at least one of a hole injection layer, a hole transport layer, an emitting-auxiliary layer, an emitting layer, an electron transport auxiliary layer, an electron transport layer, and an electron injection layer.

15. The organic electronic element of claim 13, wherein the organic material layer is an emitting layer.

16. The organic electronic element of claim 13, further comprising a light efficiency enhancing layer formed on at least one surface opposite to the organic material layer among one surface of the anode and the cathode.

17. The organic electronic element of claim 13, wherein the organic material layer comprises 2 or more stacks including a hole transport layer, an emitting layer, and an electron transport layer sequentially formed on the anode.

18. The organic electronic element of claim 17, wherein the organic material layer further comprises a charge generating layer formed between the 2 or more stacks.

19. An electronic device comprising: a display device including the organic electronic element of claim 13; and a control unit for driving the display device.

20. The organic electronic device of claim 19, wherein the organic electronic element is any one of an organic electroluminescent device (OLED), an organic solar cell, an organic photoreceptor (OPC), an organic transistor (organic TFT), and an element for monochromic or white illumination.

* * * * *